US006013474A

United States Patent [19]
Ellis et al.

[11] Patent Number: 6,013,474
[45] Date of Patent: *Jan. 11, 2000

[54] CALCIUM CHANNEL COMPOSITIONS AND METHODS

[75] Inventors: Steven Bradley Ellis, San Diego; Mark E. Williams, Carlsbad; Michael Miller Harpold, San Diego, all of Calif.; Arnold Schwartz, Cincinnati, Ohio; Robert Brenner, Austin, Tex.

[73] Assignee: Sibia Neurosciences, Inc., La Jolla, Calif.

[ * ] Notice: This patent is subject to a terminal disclaimer.

[21] Appl. No.: 08/884,599

[22] Filed: Jun. 27, 1997

Related U.S. Application Data

[62] Continuation of application No. 08/314,083, Sep. 28, 1994, Pat. No. 5,686,241, which is a division of application No. 07/914,231, Jul. 13, 1992, Pat. No. 5,407,820, which is a continuation of application No. 07/603,751, filed as application No. PCT/US89/01408, Apr. 4, 1989, abandoned, which is a continuation-in-part of application No. 07/176,899, Apr. 4, 1988, abandoned.

[51] Int. Cl.$^7$ .................................................. C12N 15/12
[52] U.S. Cl. ..................... 435/69.1; 536/23.5; 536/23.1; 536/24.31; 435/325; 435/255.1; 435/320.1
[58] Field of Search ............................... 435/69.1, 320.1, 435/325, 255.1; 536/23.5, 23.1, 24.31; 530/350

[56] References Cited

U.S. PATENT DOCUMENTS

| | | | |
|---|---|---|---|
| 4,788,135 | 11/1988 | Davis et al. | 435/320.1 |
| 4,906,564 | 3/1990 | Lyon et al. | 435/7 |
| 4,912,202 | 3/1990 | Campbell et al. | 530/387 |
| 4,950,739 | 8/1990 | Cherksey et al. | 530/350 |
| 4,954,436 | 9/1990 | Froehner et al. | 530/350 |
| 5,051,403 | 9/1991 | Miljanich et al. | 514/12 |
| 5,189,020 | 2/1993 | Miljanich et al. | 514/12 |
| 5,264,371 | 11/1993 | Miljanich et al. | 436/503 |
| 5,386,025 | 1/1995 | Jay et al. | 536/23.5 |
| 5,401,629 | 3/1995 | Harpold et al. | 435/6 |
| 5,407,820 | 4/1995 | Ellis et al. | 435/240.2 |
| 5,424,218 | 6/1995 | Miljanich et al. | 436/503 |
| 5,429,921 | 7/1995 | Harpold . | |
| 5,436,128 | 7/1995 | Harpold et al. | 435/6 |
| 5,618,720 | 4/1997 | Ellis et al. | 435/325 |
| 5,643,750 | 7/1997 | Spreyer et al. | 435/69.1 |
| 5,686,241 | 11/1997 | Ellis et al. | 435/56 |
| 5,710,250 | 1/1998 | Ellis et al. | 530/350 |
| 5,792,846 | 8/1998 | Harpold et al. | 536/23.1 |
| 5,846,757 | 12/1998 | Harpold et al. | 435/29 |
| 5,851,824 | 12/1998 | Harpold et al. | 435/325 |
| 5,874,236 | 2/1999 | Harpold et al. | 435/29 |

FOREIGN PATENT DOCUMENTS

| | | |
|---|---|---|
| 2085502 | 2/1993 | Canada . |
| 0507170 | 3/1992 | European Pat. Off. . |
| 9113077 | 9/1991 | WIPO . |
| 9202639 | 2/1992 | WIPO . |
| 9213092 | 8/1992 | WIPO . |
| 9308469 | 4/1993 | WIPO . |
| 9314098 | 7/1993 | WIPO . |
| 9402511 | 2/1994 | WIPO . |
| 9504144 | 2/1995 | WIPO . |
| 9639512 | 12/1996 | WIPO . |

OTHER PUBLICATIONS

Claudio et al., Genetic reconstitution of functional acetylcholine receptor channels in mouse fibroblasts, *Science* 238: 1688–1694 (1987).

Claudio et al., Stable expression of transfected Torpedo acetylcholine receptor α subunits in mouse fibroblast L cells, *Proc. Natl. Acad. Sci. 84:* 5967–5971 (1987).

Cooper et al., Purification and characterization of the dihydropyridine–sensitive voltage–dependent calcium channel from cardiac tissue, *J. Biol. Chem.* 262(2): 509–512 (1987).

Curran et al., Barium Modulates c–fos Expression and post–translational modification, *Proc. Natl. Acad. Sci. USA* 83:8521–8524 (1986).

Curtis et al., Reconstitution of the voltage–sensitive calcium channel purified from skeletal muscle transverse tubules, *Biochemistry* 25:3077–3083 (1986).

Curtis et al., Purification of the calcium antagonist receptor of the voltage–sensitive calcium channel from skeletal muscle transverse tubules, *Biochemistry* 23(10): 2113–2118 (1984).

Dascal et al., Expression of modulation of voltage–gated calcium channels after RNA injection in Xenopus oocytes, *Science* 231: 1147–1150 (1986).

Elliot et al., Role of calcium channel subtypes in calcium transients in hippocampal CA3 neurons, *J. Neurosci.* 15(10):6433–6444 (1995).

Ellis et al., Replacement of insulin receptor tyrosine residues 1162 and 1163 compromises insulin–stimulated kinase activity and uptake of 2–deoxyglucose, *Cell* 45:721–732 (1986).

Ellis et al., Sequence and expression of mRNAs encoding the $\alpha_1$ and $\alpha_2$ subunits of DHP–sensitive calcium channel, *Science* 241:1661–1664 (1988).

Faramisco et al., Optimal spatial requirements for the location of basic residues in peptide substrates for the cyclic AMP–dependent protein kinase, *J. Biol. Chem.* 225(9):4240–4245 (1980).

Fisch et al., c–fos sequences necessary for basal expression and induction by epidermal growth factor, 12–O–tetradecanoyl phorbol–13–acetate, and the calcium ionophore, *Mol. Cell. Biol.* 7:3490–3502 (1987).

Gielow et al., Resolution and pharmacological analysis of the voltage–dependent calcium channels of Drosophila larval muscles, *J. Neurosci.* 15(9):6085–6093 (1995).

(List continued on next page.)

Primary Examiner—Elizabeth Kemmerer
Assistant Examiner—Eliane Lazar-Wesley
Attorney, Agent, or Firm—Stephanie L. Seidman; Heller Ehrman White & McAuliffe

[57] ABSTRACT

Calcium channel (alpha)$_1$-subunit and (alpha)$_2$-subunit-encoding DNA, and related compositions and methods, are provided.

25 Claims, 20 Drawing Sheets

OTHER PUBLICATIONS

Greenberg et al., Stimulation of neuronal acetylcholine receptors induces rapid gene transcription, *Science* 234:80–83 (1986).

Akong et al., High–throughput measurement of intracellular $Ca^{2+}$ by fluorescence imaging of a 96–well microtiter plate, *Soc. Neurosci. Abstr. 21* (1995).

Barhanin et al., The calcium channel antagonists receptor from rabbit skeletal muscle: reconstitution after purification and subunit characterization, *Eur. J. Biochem. 164*:525–531 (1987).

Bezprozvanny et al., Voltage–dependent blockade of diverse types of voltage–gated $Ca^{2+}$ channels expressed in Xenopus ooxytes by the $Ca^{2+}$ channel antagonist mibefradil (Ro40–5967), *Mol. Pharmacol. 48*:540–549 (1995).

Blackshear et al., Protein kinase C–dependent and –independent pathways of proto–oncogene induction in human astrocytoma cells, *J. Biol. Chem. 262(16)*:7774–7781 (1987).

Borsotto et al., The 1,4–dihydropyridine receptor associated with the skeletal muscle voltage–dependent $Ca^{2+}$ channel, *J. Biol. Chem. 260(26)*: 14255–14263 (1985).

Boulter et al., Functional expression of two neuronal nicotinic acetylcholine receptors from cDNA clones identifies a gene family, *Proc. Natl. Acad. Sci. USA 84*:7763–7767 (1987).

Brust et al., Human neuronal voltage–dependent calcium channels: studies on subunit structure and role in channel assembly, *Neuropharmacology 32(11)*:1089–1102 (1993).

Catterall et al., Molecular properties of dihydropyridine–sensitive calcium channels in skeletal muscle, *J. Biol. Chem. 263*:3535–3538 (1988).

Mes–Masson et al., Overlapping cDNA clones define the complete coding region for the P210$^{c-abl}$ gene product associated with chronic myelogenous leukemia cells containing the Philadelphia chromosome, *Proc. Natl. Acad. Sci. USA 83*: 9768–9772 (1986).

Sambrook et al., *Molecular Cloning, A Laboratory Manual*, 2nd ed., NY: Cold Spring Harbor Laboratory Press, 1989, pp. 9.47–9.57, 16.3.

Scharf, Cloning with PCR, in *PCR Protocols A Guide To Methods and Applications*, Innis, M.A., et al., eds., New York: Academic Press; Chapter 11, pp. 84–91 (1990).

Varaldi et al., Acceleration of activation and inactivation by the β subunit of the skeletal muscle calcium channel, *Nature 352*: 159–162 (1991).

Castellano et al., Cloning and expression of a neuronal calcium channle β subunit, *J. Biol. Chem. 268*: 12359–12366 (1993).

Castellano et al., Rattus novegicus cDNA sequence, complete 5' and 3' UTR's, GenBank database record, acc. No. LO2315 (1993).

Emori et al., Isolation and sequence analysis of cDNA clones for the small subunit of rabbit calcium–dependent protease, *J. Biol. Chem. 261*: 9472–9476 (1986).

Hackett et al., DNA sequence analysis reveals extensive homologies of regions preceding hsp70 and αβ heat shock genes in *Drosophila melanogaster*, *Proc. Natl. Acad. Sci. USA 78*: 6196–6200 (1981).

Hullin et al., Calcium channel β subunit heterogeneity: functional expression of cloned cDNA from heart, aorta and brain, *EMBO J. 11(3)*: 885–890 (1992).

Kim et al. "IgG from patients with Lambert–Eaton blocks voltage–dependent calcium channels." *Science*. 239:405–408 (1988).

Roberts, et al. "Paraneoplastic Myasthenic Syndrome IgG inhibits Ca flux in a small cell carcinoma." *Nature*. 317:737–739 (1985).

Young RA, and Davis RW. "Efficient isolation of genes using antibody probes." *Proc. Natl. Acad. Sci. U.S.A.* 80(5):1194–1198 (1983).

Nikaido et al., Molecular cloning of cDNA encoding human interleukin–2 receptor, *Nature 311*:631–636 (1984).

Noda et al., Existence of distinct sodium channel messenger RNAs in rat brain, *Nature 320*:188–192 (1986).

Noda et al., Expression of functional sodium channels from cloned cDNA, *Nature* 322:826–828 (1986).

Peralta et al., Distinct primary structures, ligand–binding properties and tissue–specific expression of four human muscarinic acetylcholine receptors, *EMBO J. 6(13)*:3923–3929 (1987).

Rock et al., Biophysical and pharmacological characterization of stably expressed class B and class E $Ca^{2+}$ channels in HEK 293 cells, *Soc. Neurosci. Abstr. 21*:508.1 (1995).

Sakurai et al., Immunochemical identification and differential phosphorylation of alternatively spliced forms of the $\alpha_{1A}$ subunit of brain calcium channels, *J. Biol. Chem. 270(36)*:21234–21242 (1995).

Schmid et al., Immunochemical analysis of subunit structure of 1,4–dihydropyridine receptors associated with voltage–dependent $Ca^{2+}$ channels in skeletal, cardiac, and smooth muscles, *Biochemistry 25*: 3492–3495 (1986).

Seager et al., *Ann. N.Y. Acad. Sci. 522*:43–46 (1988).

Sharp et al., Identification and characterization of the dihydropyridine–binding subunit of the skeletal muscle dihydropyridine receptor, *J. Biol. Chem. 62*:12309–12315 (1987).

Sieber et al., The 165–KDa peptide of the purified skeletal muscle dihydropyridine receptor contains the known regulatory sites of the calcium channel, *Eur. J. Biochem. 167*:117–122 (1987).

Simerson et al., Pharmacological characterization of recombinant cell lines stably expressing human voltage–gated calcium channel subunits $\alpha_{1A}$, $\alpha_{1B}$ and $\alpha_{1E}$, *Soc. Neurosci. Abstr. 21* (1995).

Smith et al., Calcium channel activity in a purified dihydropyridine–receptor preparation of skeletal muscle, *Biochemistry 26*:7182–7188 (1987).

Stefani et al., Action of GP 47779, the active metabolite of oxcarbazepine, on the corticostriatal system. II. Modulation of high–voltage–activated calcium currents, *Epilepsia 336(10)*:997–1002 (1995).

Striessnig et al., Photoaffinity labelling of the phenylalkylamine receptor of the skeletal muscle transverse–tubule calcium channel, *FEBS Lett. 212*:247–253 (1987).

Stumpo et al., Induction of c–fos sequences involved in induction by insulin and phorbol esters, *J. Biol. Chem. 263(4)*:1611–1614 (1988).

Takahashi et al., Subunit structure of dihydropyridine–sensitive calcium channels from skeletal muscle, *Proc. Natl. Acad. Sci. USA 84*:5478–5482 (1987).

Takahashi et al., Identification of an α subunit of dihydropyridine–sensitive brain calcium channels, *Science 236*:88–91 (1987).

Takahashi et al., Dihydropyridine–sensitive calcium channels in cardiac and skeletal muscle membranes: studies with antibodies against the alpha subunits, *Biochemistry 26*:5518–5526 (1987).

Takahashi et al., Dihydropyridine–sensitive calcium channels in cardiac and skeletal muscle membranes: studies with antibodies against the α–subunits, *Biochemistry* 26(17):1518–1526 (1987).

Tanabe et al., Primary Structure of the Receptor for Calcium Channel Blockers from Skeletal Muscle, *Nature* 328:313–318 (1987).

Utz et al., Inhibition of L–type calcium currents in guinea pig ventricular myocytes by the κ–opioid agonist U50488H does not involve binding to opiate receptors, *J. Pharmacol. Exptl. Therap.* 274(2):627–633 (1995).

Vaghy et al., Mechanism of action of calcium channel modulator drugs, *Ann. N.Y. Acad. Sci.* 522: 176–186 (1988).

Vaghy et al., Identification of a novel 1,4–dihydropyridine– and phenylalkylamine–binding polypeptide in calcium channel preparations, *J. Biol. Chem.* 262:14337–14342 (1987).

von Heijne, Signal sequences: the limits of variation, *J. Mol. Biol.* 184:99–105 (1985).

Westenbroek et al., Immunochemical identification and subcellular distribution of the $\alpha_{1A}$ subunits of brain calcium channels, *J. Neurosci.* 15(10):6403–6418 (1995).

Williams, Structure and functional expression of $\alpha_1$, $\alpha_2$ and β subunits of a novel human neuronal calcium channel subtype, *Neuron* 8:71–84 (1992).

Williams et al., Structure and functional expression of an ω–Conotoxin–Sensitive Human N–Type Calcium Channel, *Science* 257:389–395 (1992).

Williams et al., Structure and functional characterization of neuronal $\alpha_{1E}$ calcium channel subtypes, *J. Biol. Chem.* 269(35):22347–22357 (1994).

Williams et al., An essential structural domain that determines the biophysical properties of the human $\alpha_{1A}$ high–voltage activated calcium channel, *Soc. Neurosci. Abstr.* 21:508.3 (1995).

Wood, Gene cloning based on long oligonucleotide probes, *Methods in Enzymology* 152:443–447 (1987).

Yokoyama et al., Biochemical properties and subcellular distribution of the neuronal class E calcium channel $\alpha_1$ subunit, *J. Neurosci.* 15(10):6419–6432 (1995).

Hofmann et al., Regulation of the L–type calcium channel, *TIPS* 8:393–398 (1987).

Hubbard et al., Synthesis and processing of asparagine–linked oligosaccharides[1,2], *Ann. Rev. Biochem.* 50:555–583 (1981).

Imagawa et al., Phosphorylation of the 1,4–dihydropyridine receptor of the voltage–dependent $Ca^{2+}$ channel by an intrinsic protein kinase in isolated triads from rabbit skeletal muscle, *J. Biol. Science* 262(17):8333–8339 (1987).

Ishibari et al., Regional difference of high voltage–activated $Ca^{2+}$ channels in rat CNS neurones, *NeuroReport* 6:1621–1624 (1995).

Kozak, An analysis of 5'–noncoding sequences from 699 vertebrate messenger RNAs, *Nucleic Acids Research* 15(20):8125–8148 (1987).

Lang et al., The effect of myasthenic syndrome antibody on presynaptic channels in the mouse, *J. Physiol.* 390:257–270 (1987).

Leung et al., Structural characterization of the 1,4–dihydropyridine receptor of the voltage–dependent $Ca^{2+}$ channel from rabbit skeletal muscle, *J. Biol. Chem.* 262(17):7943–7946 (1987).

Leung et al., Monoclonal antibody characterization of the 1,4–dihydropyridine receptor of rabbit skeletal muscle, *Ann. N.Y. Acad. Sci.* 522: 43–46 (1988).

Leung et al., Biochemical and ultrastructural characterization of the 1,4–dihydropyridine receptor from rabbit skeletal muscle, *J. Biol. Chem.* 263(2):994–1101 (1988).

Meshi et al., Nucleotide sequence of the 30K protein cistron of cowpea strain of tobacco mosaic virus, *Nucleic Acids Research* 10:6111–6117 (1982).

Mierendorf et al., Gene isolation by screening λgt11 libraries with antibodies, *Methods in Enzymology* 152:458–469 (1986).

Miller, Multiple calcium channels and neuronal function, *Science* 234:46–52 (1987)Miller (1987).

Morton et al., Monoclonal antibody identifies a 200–kDA subunit of the dihydropyridine–sensitive calcium channel, *J. Biol. Chem.* 262:11904–11907 (1987).

Nakayama et al., Purification of a putative $Ca^{2+}$ channel protein from rabbit skeletal muscle, *J. Biol. Chem.* 262: 6572–6576 (1987).

FIGURE 1a

```
                                                       GCGGGGAA CACTGGGGAC-61
GCAGGGAAGA GAGGGCCGCG GGGTGGGGGA GCAGCAGGAA GCGCCGTGGC CAGGGAAGCC-1
```

| ATG | GAG | CCA | TCC | TCA | CCC | CAG | GAT | GAG | GGC | CTG | AGG | AAG | AAA | CAG | CCC | 48 |
| MET | GLU | PRO | SER | SER | PRO | GLN | ASP | GLU | GLY | LEU | ARG | LYS | LYS | GLN | PRO | |
| | | | | 5 | | | | | 10 | | | | | 15 | | |

| AAG | AAG | CCC | CTG | CCC | GAG | GTC | CTG | CCC | AGG | CCG | CCG | CGG | GCT | CTG | TTC | 96 |
| LYS | LYS | PRO | LEU | PRO | GLU | VAL | LEU | PRO | ARG | PRO | PRO | ARG | ALA | LEU | PHE | |
| | | | 20 | | | | | 25 | | | | | 30 | | | |

| TGC | CTG | ACC | CTG | CAG | AAC | CCG | CTG | AGG | AAG | GCG | TGC | ATC | AGC | ATC | GTG | 144 |
| CYS | LEU | THR | LEU | GLN | ASN | PRO | LEU | ARG | LYS | ALA | CYS | ILE | SER | ILE | VAL | |
| 35 | | | | 40 | | | | | 45 | | | | | | | |

| GAA | TGG | AAA | CCC | TTC | GAG | ACC | ATC | ATC | CTG | CTC | ACC | ATC | TTT | GCC | AAC | 192 |
| GLU | TRP | LYS | PRO | PHE | GLU | THR | ILE | ILE | LEU | LEU | THR | ILE | PHE | ALA | ASN | |
| | 50 | | | | 55 | | | | | 60 | | | | | | |

| TGT | GTG | GCC | CTG | GCC | GTG | TAC | CTG | CCC | ATG | CCC | GAG | GAT | GAC | AAC | AAC | 240 |
| CYS | VAL | ALA | LEU | ALA | VAL | TYR | LEU | PRO | MET | PRO | GLU | ASP | ASP | ASN | ASN | |
| 65 | | | | | 70 | | | | | 75 | | | | * | 80 | |

| TCC | CTG | AAC | CTG | GGC | CTG | GAG | AAG | CTG | GAG | TAC | TTC | TTC | CTC | ACC | GTC | 288 |
| SER | LEU | ASN | LEU | GLY | LEU | GLU | LYS | LEU | GLU | TYR | PHE | PHE | LEU | THR | VAL | |
| | | | | 85 | | | | | 90 | | | | | 95 | | |

| TTC | TCC | ATC | GAA | GCC | GCC | ATG | AAG | ATC | ATC | GCC | TAC | GGC | TTC | CTG | TTC | 336 |
| PHE | SER | ILE | GLU | ALA | ALA | MET | LYS | ILE | ILE | ALA | TYR | GLY | PHE | LEU | PHE | |
| | | | 100 | | | | | 105 | | | | | 110 | | | |

| CAC | CAG | GAC | GCC | TAC | CTG | CGC | AGC | GGC | TGG | AAC | GTG | CTG | GAC | TTC | ATC | 384 |
| HIS | GLN | ASP | ALA | TYR | LEU | ARG | SER | GLY | TRP | ASN | VAL | LEU | ASP | PHE | ILE | |
| | | 115 | | | | | 120 | | | | | 125 | | | | |

| ATC | GTC | TTC | CTG | GGG | GTC | TTC | ACG | GCG | ATT | CTG | GAA | CAG | GTC | AAC | GTC | 432 |
| ILE | VAL | PHE | LEU | GLY | VAL | PHE | THR | ALA | ILE | LEU | GLU | GLN | VAL | ASN | VAL | |
| | | 130 | | | | | 135 | | | | | 140 | | | | |

| ATC | CAG | AGC | AAC | ACG | GCC | CCG | ATG | AGC | AGC | AAA | GGA | GCC | GGC | CTG | GAC | 480 |
| ILE | GLN | SER | ASN | THR | ALA | PRO | MET | SER | SER | LYS | GLY | ALA | GLY | LEU | ASP | |
| 145 | | | | | 150 | | | | | 155 | | | | | 160 | |

| GTC | AAG | GCC | CTG | AGG | GCC | TTC | CGT | GTG | CTC | AGA | CCC | CTC | CGG | CTG | GTG | 528 |
| VAL | LYS | ALA | LEU | ARG | ALA | PHE | ARG | VAL | LEU | ARG | PRO | LEU | ARG | LEU | VAL | |
| | | | 165 | | | | | 170 | | | | | 175 | | | |

FIGURE 1b

| TCG | GGG | GTG | CCT | AGT | TTG | CAG | GTG | GTC | CTC | AAC | TCC | ATC | TTC | AAG | GCC | 576 |
| SER | GLY | VAL | PRO | SER | LEU | GLN | VAL | VAL | LEU | ASN | SER | ILE | PHE | LYS | ALA | |
| | | 180 | | | | 185 | | | | | | 190 | | | | |

| ATG | CTC | CCC | CTG | TTC | CAC | ATC | GCC | CTG | CTC | GTC | CTC | TTC | ATG | GTC | ATC | 624 |
| MET | LEU | PRO | LEU | PHE | HIS | ILE | ALA | LEU | LEU | VAL | LEU | PHE | MET | VAL | ILE | |
| | | 195 | | | | 200 | | | | | | 205 | | | | |

| ATC | TAC | GCC | ATC | ATC | GGG | CTG | GAG | CTC | TTC | AAG | GGC | AAG | ATG | CAC | AAG | 672 |
| ILE | TYR | ALA | ILE | ILE | GLY | LEU | GLU | LEU | PHE | LYS | GLY | LYS | MET | HIS | LYS | |
| | | 210 | | | | 215 | | | | 220 | | | | | | |

| ACC | TGC | TAC | TAC | ATC | GGG | ACA | GAC | ATC | GTG | GCC | ACA | GTG | GAG | AAT | GAG | 720 |
| THR | CYS | TYR | TYR | ILE | GLY | THR | ASP | ILE | VAL | ALA | THR | VAL | GLU | ASN | GLU | |
| 225 | | | | | 230 | | | | | 235 | | | | | 240 | |

| AAG | CCC | TCG | CCC | TGC | GCT | AGG | ACG | GGC | TCG | GGG | CGC | CCC | TGC | ACC | ATC | 768 |
| LYS | PRO | SER | PRO | CYS | ALA | ARG | THR | GLY | SER | GLY | ARG | PRO | CYS | THR | ILE | |
| | | | | 245 | | | | | 250 | | | | | 255 | | |

| AAC | GGC | AGC | GAG | TGC | CGG | GGC | GGC | TGG | CCG | GGG | CCC | AAC | CAC | GGC | ATC | 816 |
| ASN | GLY | SER | GLU | CYS | ARG | GLY | GLY | TRP | PRO | GLY | PRO | ASN | HIS | GLY | ILE | |
| * | | | 260 | | | | | 265 | | | | | 270 | | | |

| ACG | CAC | TTC | GAC | AAC | TTC | GGC | TTC | TCC | ATG | CTC | ACC | GTG | TAC | CAG | TGC | 864 |
| THR | HIS | PHE | ASP | ASN | PHE | GLY | PHE | SER | MET | LEU | THR | VAL | TYR | GLN | CYS | |
| | | 275 | | | | | 280 | | | | | 285 | | | | |

| ATC | ACC | ATG | GAG | GGC | TGG | ACA | GAT | GTC | CTC | TAC | TGG | GTC | AAC | GAT | GCC | 912 |
| ILE | THR | MET | GLU | GLY | TRP | THR | ASP | VAL | LEU | TYR | TRP | VAL | ASN | ASP | ALA | |
| | | 290 | | | | 295 | | | | | 300 | | | | | |

| ATC | GGG | AAC | GAG | TGG | CCC | TGG | ATC | TAC | TTT | GTC | ACT | CTC | ATC | CTG | CTG | 960 |
| ILE | GLY | ASN | GLU | TRP | PRO | TRP | ILE | TYR | PHE | VAL | THR | LEU | ILE | LEU | LEU | |
| 305 | | | | | 310 | | | | | 315 | | | | | 320 | |

| GGG | TCC | TTC | TTC | ATC | CTC | AAC | CTG | GTG | CTG | GGC | GTC | CTG | AGT | GGG | GAA | 1008 |
| GLY | SER | PHE | PHE | ILE | LEU | ASN | LEU | VAL | LEU | GLY | VAL | LEU | SER | GLY | GLU | |
| | | | | 325 | | | | | 330 | | | | | 335 | | |

| TTC | ACC | AAG | GAG | CGG | GAG | AAG | GCC | AAG | TCC | AGG | GGA | ACC | TTC | CAG | AAG | 1056 |
| PHE | THR | LYS | GLU | ARG | GLU | LYS | ALA | LYS | SER | ARG | GLY | THR | PHE | GLN | LYS | |
| | | | 340 | | | | | 345 | | | | | 350 | | | |

| CTG | CGG | GAG | AAG | CAG | CAG | CTG | GAG | GAG | GAC | CTT | CGG | GGC | TAC | ATG | AGC | 1104 |
| LEU | ARG | GLU | LYS | GLN | GLN | LEU | GLU | GLU | ASP | LEU | ARG | GLY | TYR | MET | SER | |
| | | | 355 | | | | | 360 | | | | | 365 | | | |

FIGURE 1c

```
TGG ATC ACG CAG GGC GAG GTC ATG GAC GTG GAG GAC CTG AGA GAA GGA  1152
TRP ILE THR GLN GLY GLU VAL MET ASP VAL GLU ASP LEU ARG GLU GLY
    370             375             380

AAG CTG TCC TTG GAA GAG GGA GGC TCC GAC ACG GAA AGC CTG TAC GAA  1200
LYS LEU SER LEU GLU GLU GLY GLY SER ASP THR GLU SER LEU TYR GLU
385             390             395                         400

ATC GAG GGC TTG AAC AAA ATC ATC CAG TTC ATC CGA CAC TGG AGG CAG  1248
ILE GLU GLY LEU ASN LYS ILE ILE GLN PHE ILE ARG HIS TRP ARG GLN
                405             410             415

TGG AAC CGT GTC TTT CGC TGG AAG TGC CAT GAC CTG GTG AAG TCG AGA  1296
TRP ASN ARG VAL PHE ARG TRP LYS CYS HIS ASP LEU VAL LYS SER ARG
            420             425             430
```

```
GTC TTC TAC TGG CTG GTC ATC CTG ATC GTG GCC CTC AAC ACC CTG TCC  1344
VAL PHE TYR TRP LEU VAL ILE LEU ILE VAL ALA LEU ASN THR LEU SER
        435             440             445
```

```
ATC GCC TCG|GAG CAC CAC AAC CAG CCG CTC TGG CTG ACC CAC TTG CAA  1392
ILE ALA SER|GLU HIS HIS ASN GLN PRO LEU TRP LEU THR HIS LEU GLN
    450             455             460

GAC ATC|GCC AAT CGA GTG CTG CTG TCA CTC TTC ACC ATC GAG ATG CTG  1440
ASP ILE|ALA ASN ARG VAL LEU LEU SER LEU PHE THR ILE GLU MET LEU
465             470             475             480

CTG AAG ATG TAC GGG CTG|GGC CTG CGC CAG TAC TTC ATG TCC|ATC TTC  1488
LEU LYS MET TYR GLY LEU|GLY LEU ARG GLN TYR PHE MET SER|ILE PHE
            485                 490                     495

AAC CGC TTC GAC TGC TTC GTG GTG TGC AGC GGC ATC CTG GAG CTG CTG  1536
ASN ARG PHE ASP CYS PHE VAL VAL CYS SER GLY ILE LEU GLU LEU LEU
            500             505             510

CTG|GTG GAG TCG GGC GCC ATG ACG CCG CTG GGC|ATC TCC GTG TTG CGC  1584
LEU|VAL GLU SER GLY ALA MET THR PRO LEU GLY|ILE SER VAL LEU ARG
        515             520                 525

TGC ATC CGC CTC CTG AGG CTC TTC AAG ATC ACC AAG TAC TGG|ACG TCG  1632
CYS ILE ARG LEU LEU ARG LEU PHE LYS ILE THR LYS TYR TRP|THR SER
        530             535             540
```

FIGURE 1d

```
CTC AGC AAC CTG GTG GCC TCC CTG CTC AAC TCC ATC CGC TCC ATC GCC 1680
LEU SER ASN LEU VAL ALA SER LEU LEU ASN SER ILE ARG SER ILE ALA
545                 550                 555                 560

TCG CTG CTG CTG CTG CTC TTC CTC TTC ATC ATC ATC TTC GCC CTG CTG 1728
SER LEU LEU LEU LEU LEU PHE LEU PHE ILE ILE ILE PHE ALA LEU LEU
                    565                 570                 575

GGC ATG CAG CTC TTC GGG GGG CGG TAC GAC TTC GAG GAC ACG GAA GTG 1766
GLY MET GLN LEU PHE GLY GLY ARG TYR ASP PHE GLU ASP THR GLU VAL
            580                 585                 590

CGA CGC AGC AAC TTC GAC AAC TTC CCC CAG GCC CTC ATC AGC GTC TTC 1824
ARG ARG SER ASN PHE ASP ASN PHE PRO GLN ALA LEU ILE SER VAL PHE
        595                 600                 605

CAG GTG CTG ACG GGT GAG GAC TGG AAC TCC GTG ATG TAC AAC GGG ATC 1872
GLN VAL LEU THR GLY GLU ASP TRP ASN SER VAL MET TYR ASN GLY ILE
    610                 615                 620

ATG GCC TAC GGA GGC CCG TCC TAC CCG GGC GTT CTC GTG TGC ATC TAT 1920
MET ALA TYR GLY GLY PRO SER TYR PRO GLY VAL LEU VAL CYS ILE TYR
625                 630                 635                 640

TTC ATC ATC CTT TTT GTC TGC GGC AAC TAT ATC CTG CTG AAT GTC TTC 1968
PHE ILE ILE LEU PHE VAL CYS GLY ASN TYR ILE LEU LEU ASN VAL PHE
                    645                 650                 655

CTG GCC ATC GCC GTG GAC AAC CTG GCC GAG GCC GAG AGC CTG ACT TCC 2016
LEU ALA ILE ALA VAL ASP ASN LEU ALA GLU ALA GLU SER LEU THR SER
            660                 665                 670

GCG CAA AAG GCC AAG GCC GAG GAG AGG AAA CGT AGG AAG ATG TCC AGG 2064
ALA GLN LYS ALA LYS ALA GLU GLU ARG LYS ARG ARG LYS MET SER ARG
        675                 680                 685   P

GGT CTC CCT GAC AAG ACG GAG GAG GAG AAG TCT GTG ATG GCC AAG AAG 2112
GLY LEU PRO ASP LYS THR GLU GLU GLU LYS SER VAL MET ALA LYS LYS
    690                 695                 700

CTG GAG CAG AAG CCC AAG GGG GAG GGC ATC CCC ACC ACT GCC AAG CTC 2160
LEU GLU GLN LYS PRO LYS GLY GLU GLY ILE PRO THR THR ALA LYS LEU
705                 710                 715                 720

AAG GTC GAT GAG TTC GAA TCT AAC GTC AAC GAG GTG AAG GAC CCC TAC 2208
LYS VAL ASP GLU PHE GLU SER ASN VAL ASN GLU VAL LYS ASP PRO TYR
                    725                 730                 735
```

FIGURE 1e

```
CCT TCA GCT GAC TTC CCA GGG GAT GAT GAG GAG GAC GAG CCT GAG ATC   2256
PRO SER ALA ASP PHE PRO GLY ASP ASP GLU GLU ASP GLU PRO GLU ILE
            740                 745                 750

CCA GTG AGC CCC CGA CCG CGC CCG CTG GCC GAG CTG CAG CTC AAA GAG   2304
PRO VAL SER PRO ARG PRO ARG PRO LEU ALA GLU LEU GLN LEU LYS GLU
            755                 760                 765

AAG GCA GTG CCC ATC CCG GAA GCC AGC TCC TTC TTC ATC TTC AGT CCC   2352
LYS ALA VAL PRO ILE PRO GLU ALA SER SER PHE PHE ILE PHE SER PRO
    770                 775                 780

ACC AAT AAG GTC CGT GTC CTG TGT CAC CGC ATC GTC AAC GCC ACC TGG   2400
THR ASN LYS VAL ARG VAL LEU CYS HIS ARG ILE VAL ASN ALA THR TRP
785                 790                 795   *             800

TTC ACC AAC TTC ATC CTG CTC TTC ATC CTG CTC AGC AGT GCT GCG CTG   2448
PHE THR ASN PHE ILE LEU LEU PHE ILE LEU LEU SER SER ALA ALA LEU
                805                 810                 815

GCC GCC GAG GAC CCC ATC CGG GCG GAG TCC GTG AGG AAT CAG ATC CTT   2496
ALA ALA GLU ASP PRO ILE ARG ALA GLU SER VAL ARG ASN GLN ILE LEU
        820                 825                 830

GGA TAT TTT GAT ATT GCC TTC ACC TCT GTC TTC ACT GTG GAG ATT GTC   2544
GLY TYR PHE ASP ILE ALA PHE THR SER VAL PHE THR VAL GLU ILE VAL
        835                 840                 845

CTC AAG ATG ACA ACC TAC GGC GCC TTC CTG CAC AAG GGC TCC TTC TGC   2592
LEU LYS MET THR THR TYR GLY ALA PHE LEU HIS LYS GLY SER PHE CYS
    850                 855                 860

CGC AAC TAC TTC AAC ATC CTG GAC CTG CTG GTG GTG GCC GTG TCT CTC   2640
ARG ASN TYR PHE ASN ILE LEU ASP LEU LEU VAL VAL ALA VAL SER LEU
865                 870                 875                 880

ATC TCC ATG GGT CTC GAG TCC AGC ACC ATC TCC GTG GTA AAG ATC CTG   2688
ILE SER MET GLY LEU GLU SER SER THR ILE SER VAL VAL LYS ILE LEU
                885                 890                 895

AGA GTG CTA AGG GTG CTC CGG CCC CTG CGA GCC ATC AAC AGA GCC AAA   2736
ARG VAL LEU ARG VAL LEU ARG PRO LEU ARG ALA ILE ASN ARG ALA LYS
            900                 905                 910
```

FIGURE 1f

```
GGG TTG AAG CAC GTG GTC CAG TGC GTG TTC GTG GCC ATC CGC ACC ATC 2784
GLY LEU LYS HIS VAL VAL GLN CYS VAL PHE VAL ALA ILE ARG THR ILE
        915                 920                 925

GGG AAC ATC GTC CTG GTC ACC ACG CTC CTG CAG TTC ATG TTC GCC TGC 2832
GLY ASN ILE VAL LEU VAL THR THR LEU LEU GLN PHE MET PHE ALA CYS
    930                 935                 940

ATC GGT GTC CAG CTC TTC AAG GGC AAG TTC TTC AGC TGC AAT GAC CTA 2880
ILE GLY VAL GLN LEU PHE LYS GLY LYS PHE PHE SER CYS ASN ASP LEU
945                 950                 955                 960

TCC AAG ATG ACA GAA GAG GAG TGC AGG GGC TAC TAC TAT GTA TAC AAG 2928
SER LYS MET THR GLU GLU GLU CYS ARG GLY TYR TYR TYR VAL TYR LYS
        965                 970                 975

GAC GGG GAC CCC ACG CAG ATG GAG CTG CGC CCC CGC CAG TGG ATA CAC 2976
ASP GLY ASP PRO THR GLN MET GLU LEU ARG PRO ARG GLN TRP ILE HIS
        980                 985                 990

AAT GAC TTC CAC TTT GAC AAC GTG CTG TCG GCC ATG ATG TCG CTC TTC 3024
ASN ASP PHE HIS PHE ASP ASN VAL LEU SER ALA MET MET SER LEU PHE
        995                 1000                1005

ACG GTG TCC ACC TTC GAG GGA TGG CCC CAG CTG CTG TAC AGG GCC ATA 3072
THR VAL SER THR PHE GLU GLY TRP PRO GLN LEU LEU TYR ARG ALA ILE
    1010                1015                1020

GAC TCC AAC GAG GAG GAC ATG GGC CCC GTT TAC AAC AAC CGA GTG GAG 3120
ASP SER ASN GLU GLU ASP MET GLY PRO VAL TYR ASN ASN ARG VAL GLU
1025                1030                1035                1040

ATG GCC ATC TTC TTC ATC ATC TAC ATC ATC CTC ATT GCC TTC TTC ATG 3168
MET ALA ILE PHE PHE ILE ILE TYR ILE ILE LEU ILE ALA PHE PHE MET
            1045                1050                1055

ATG AAC ATC TTT GTG GGC TTT GTC ATC GTC ACC TTC CAG GAG CAG GGG 3216
MET ASN ILE PHE VAL GLY PHE VAL ILE VAL THR PHE GLN GLU GLN GLY
            1060                1065                1070

GAG ACG GAG TAC AAG AAC TGC GAG CTG GAC AAG AAC CAG CGC CAG TGT 3264
GLU THR GLU TYR LYS ASN CYS GLU LEU ASP LYS ASN GLN ARG GLN CYS
        1075                1080                1085

GTG CAG TAT GCC CTG AAG GCC CGC CCA CTT CGG TGC TAC ATC CCC AAG 3312
VAL GLN TYR ALA LEU LYS ALA ARG PRO LEU ARG CYS TYR ILE PRO LYS
        1090                1095                1100
```

FIGURE 1g

```
AAC CCA TAC CAG TAC CAG GTG TGG TAC GTC GTC ACC TCC TCC TAC TTT  3360
ASN PRO TYR GLN TYR GLN VAL TRP TYR VAL VAL THR SER SER TYR PHE
1105                1110                1115                1120

GAA TAC CTG ATG TTC GCC CTC ATC ATG CTC AAC ACC ATC TGC CTG GGC  3408
GLU TYR LEU MET PHE ALA LEU ILE MET LEU ASN THR ILE CYS LEU GLY
                1125                1130                1135

ATG CAG CAC TAC CAC CAG TCG GAG GAG ATG AAC CAC ATC TCA GAC ATC  3456
MET GLN HIS TYR HIS GLN SER GLU GLU MET ASN HIS ILE SER ASP ILE
            1140                1145                1150

CTC AAT GTG GCC TTC ACC ATC ATC TTC ACG CTG GAG ATG ATT CTC AAG  3504
LEU ASN VAL ALA PHE THR ILE ILE PHE THR LEU GLU MET ILE LEU LYS
        1155                1160                1165

CTC TTG GCG TTC AAG GCC AGG GGC TAT TTC GGA GAC CCC TGG AAT GTG  3552
LEU LEU ALA PHE LYS ALA ARG GLY TYR PHE GLY ASP PRO TRP ASN VAL
        1170            1175                1180

TTC GAC TTC CTG ATC GTC ATC GGC AGC ATC ATT GAC GTC ATC CTC AGC  3600
PHE ASP PHE LEU ILE VAL ILE GLY SER ILE ILE ASP VAL ILE LEU SER
1185                1190                1195                1200

GAG ATC GAC ACT TTC CTG GCC TCC AGC GGG GGA CTG TAT TGC CTG GGT  3648
GLU ILE ASP THR PHE LEU ALA SER SER GLY GLY LEU TYR CYS LEU GLY
                1205                1210                1215

GGC GGC TGC GGG AAC GTT GAC CCA GAC GAG AGC GCC CGC ATC TCC AGT  3696
GLY GLY CYS GLY ASN VAL ASP PRO ASP GLU SER ALA ARG ILE SER SER
            1220                1225                1230

GCC TTC TTC CGC CTG TTC CGG GTT ATG AGG CTG ATC AAG CTG CTG AGT  3744
ALA PHE PHE ARG LEU PHE ARG VAL MET ARG LEU ILE LYS LEU LEU SER
        1235                1240                1245

CGG GCC GAG GGC GTG CGC ACG CTG CTG TGG ACG TTC ATC AAG TCC TTC  3792
ARG ALA GLU GLY VAL ARG THR LEU LEU TRP THR PHE ILE LYS SER PHE
        1250                1255                1260

CAG GCC CTG CCC TAC GTG GCC CTG CTC ATC GTC ATG CTG TTC TTC ATC  3840
GLN ALA LEU PRO TYR VAL ALA LEU LEU ILE VAL MET LEU PHE PHE ILE
1265                1270                1275                1280
```

FIGURE 1h

```
TAC GCC GTC ATC GGC ATG CAG ATG TTT GGA AAG ATC GCC CTG GTG GAC  3888
TYR ALA VAL ILE GLY MET GLN MET PHE GLY LYS ILE ALA LEU VAL ASP
            1285                1290                1295

GGG ACC CAG ATC AAC CGC AAC AAC AAC TTC CAG ACC TTC CCG CAG GCC  3936
GLY THR GLN ILE ASN ARG ASN ASN ASN PHE GLN THR PHE PRO GLN ALA
                1300                1305                1310

GTG CTG CTG CTC TTC AGG TGT GCG ACA GGG GAG GCG TGG CAA GAG ATC  3984
VAL LEU LEU LEU PHE ARG CYS ALA THR GLY GLU ALA TRP GLN GLU ILE
            1315                1320                1325

CTG CTG GCC TGC AGC TAC GGG AAG TTG TGC GAC CCA GAG TCA GAC TAC  4032
LEU LEU ALA CYS SER TYR GLY LYS LEU CYS ASP PRO GLU SER ASP TYR
        1330                1335                1340

GCC CCG GGC GAG GAG TAC ACG TGT GGC ACC AAC TTC GCC TAC TAC TAC  4080
ALA PRO GLY GLU GLU TYR THR CYS GLY THR ASN PHE ALA TYR TYR TYR
1345                1350                1355                1360

TTC ATC AGC TTC TAC ATG CTC TGC GCC TTC CTG ATC ATC AAC CTC TTC  4128
PHE ILE SER PHE TYR MET LEU CYS ALA PHE LEU ILE ILE ASN LEU PHE
            1365                1370                1375

GTG GCT GTC ATC ATG GAC AAC TTT GAC TAC CTG ACA CGC GAC TGG TCC  4176
VAL ALA VAL ILE MET ASP ASN PHE ASP TYR LEU THR ARG ASP TRP SER
            1380                1385                1390

ATC CTG GGC CCT CAC CAC CTG GAC GAG TTC AAG GCC ATC TGG GCA GAG  4224
ILE LEU GLY PRO HIS HIS LEU ASP GLU PHE LYS ALA ILE TRP ALA GLU
            1395                1400                1405

TAT GAC CCA GAG GCC AAG GGG CGA ATC AAG CAC CTG GAC GTG GTG ACC  4272
TYR ASP PRO GLU ALA LYS GLY ARG ILE LYS HIS LEU ASP VAL VAL THR
        1410                1415                1420

CTG CTG AGA AGG ATC CAG CCC CCT CTG GGC TTC GGG AAG TTC TGT CCA  4320
LEU LEU ARG ARG ILE GLN PRO PRO LEU GLY PHE GLY LYS PHE CYS PRO
1425                1430                1435                1440

CAC CGG GTG GCC TGT AAG CGC CTG GTG GGC ATG AAC ATG CCC CTG AAC  4368
HIS ARG VAL ALA CYS LYS ARG LEU VAL GLY MET ASN MET PRO LEU ASN
            1445                1450                1455

AGT GAC GGC ACG GTC ACC TTC AAT GCC ACG CTC TTT GCC CTG GTG CGC  4416
SER ASP GLY THR VAL THR PHE ASN ALA THR LEU PHE ALA LEU VAL ARG
            1460             *  1465                1470

ACG GCC CTC AAG ATC AAG ACA GAA GGT AAC TTC GAG CAG GCC AAC GAG  4464
THR ALA LEU LYS ILE LYS THR GLU GLY ASN PHE GLU GLN ALA ASN GLU
            1475                1480                1485
```

FIGURE 1i

```
GAG CTG AGG GCC ATC ATC AAG AAG ATC TGG AAG AGA ACC AGC ATG AAG   4512
GLU LEU ARG ALA ILE ILE LYS LYS ILE TRP LYS ARG THR SER MET LYS
        1490                1495                1500     P

CTA CTG GAC CAG GTC ATC CCT CCC ATA GGA GAT GAC GAG GTG ACC GTG   4560
LEU LEU ASP GLN VAL ILE PRO PRO ILE GLY ASP ASP GLU VAL THR VAL
1505                1510                1515                1520

GGG AAG TTC TAC GCC ACA TTC CTC ATC CAG GAG CAC TTC CGG AAG TTC   4608
GLY LYS PHE TYR ALA THR PHE LEU ILE GLN GLU HIS PHE ARG LYS PHE
                1525                1530                1535

ATG AAG CGC CAG GAG GAA TAT TAT GGG TAT CGG CCC AAG AAG GAC ACC   4656
MET LYS ARG GLN GLU GLU TYR TYR GLY TYR ARG PRO LYS LYS ASP THR
            1540                1545                1550

GTG CAG ATC CAG GCT GGG CTG CGG ACC ATA GAG GAG GAG GCG GCC CCT   4704
VAL GLN ILE GLN ALA GLY LEU ARG THR ILE GLU GLU GLU ALA ALA PRO
        1555                1560                1565

GAG ATC CGC CGC ACC ATC TCA GGA GAC CTG ACC GCC GAG GAG GAG CTG   4752
GLU ILE ARG ARG THR ILE SER GLY ASP LEU THR ALA GLU GLU GLU LEU
    1570                1575                1580
                         P

GAG AGA GCC ATG GTG GAG GCT GCG ATG GAG GAG AGG ATC TTC CGG AGG   4800
GLU ARG ALA MET VAL GLU ALA ALA MET GLU GLU ARG ILE PHE ARG ARG
1585                1590                1595                1600

ACC GGA GGC CTG TTT GGC CAG GTG GAC ACC TTC CTG GAA AGG ACC AAC   4848
THR GLY GLY LEU PHE GLY GLN VAL ASP THR PHE LEU GLU ARG THR ASN
                1605                1610                1615

TCC CTA CCC CCG GTG ATG GCC AAC CAA AGA CCG CTC CAG TTT GCT GAG   4896
SER LEU PRO PRO VAL MET ALA ASN GLN ARG PRO LEU GLN PHE ALA GLU
            1620                1625                1630

ATA GAA ATG GAA GAG CTT GAG TCG CCT GTC TTC TTG GAG GAC TTC CCT   4944
ILE GLU MET GLU GLU LEU GLU SER PRO VAL PHE LEU GLU ASP PHE PRO
        1635                1640                1645

CAA GAC GCA AGA ACC AAC CCT CTC GCT CGT GCC AAT ACC AAC AAC GCC   4992
GLN ASP ALA ARG THR ASN PRO LEU ALA ARG ALA ASN THR ASN ASN ALA
    1650                1655                1660

AAT GCC AAT GTT GCC TAT GGC AAC AGC AAC CAT AGC AAC AAC CAG ATG   5040
ASN ALA ASN VAL ALA TYR GLY ASN SER ASN HIS SER ASN ASN GLN MET
1665                1670         *  1675                1680

TTT TCC AGC GTC CAC TGT GAA AGG GAG TTC CCG GGA GAG GCG GAG ACA   5088
PHE SER SER VAL HIS CYS GLU ARG GLU PHE PRO GLY GLU ALA GLU THR
                1685                1690                1695
```

FIGURE 1j

```
CCG GCT GCC GGA CGA GGA GCC CTC AGC CAC TCC CAC AGG GCC CTG GGA  5136
PRO ALA ALA GLY ARG GLY ALA LEU SER HIS SER HIS ARG ALA LEU GLY
            1700                1705                1710

CCT CAC AGC AAG CCC TGT GCT GGA AAA CTG AAT GGG CAG CTG GTC CAG  5184
PRO HIS SER LYS PRO CYS ALA GLY LYS LEU ASN GLY GLN LEU VAL GLN
        1715                1720                1725

CCG GGA ATG CCC ATC AAC CAG GCA CCT CCT GCC CCC TGC CAG CAG CCT  5232
PRO GLY MET PRO ILE ASN GLN ALA PRO PRO ALA PRO CYS GLN GLN PRO
    1730                1735                1740

AGC ACA GAT CCC CCA GAG CGC GGG CAG AGG AGG ACC TCC CTG ACA GGG  5280
SER THR ASP PRO PRO GLU ARG GLY GLN ARG ARG THR SER LEU THR GLY
1745                1750                1755  P             1760

TCT CTG CAA GAC GAA GCA CCC CAG AGG AGG AGC TCC GAG GGG AGC ACC  5328
SER LEU GLN ASP GLU ALA PRO GLN ARG ARG SER SER GLU GLY SER THR
                1765                1770  P             1775

CCC AGG CGC CCG GCT CCT GCT ACA GCT CTG CTG ATC CAA GAG GCT CTG  5376
PRO ARG ARG PRO ALA PRO ALA THR ALA LEU LEU ILE GLN GLU ALA LEU
            1780                1785                1790

GTT CGA GGG GGC CTG GAC ACC TTG GCA GCT GAT GCT GGC TTC GTC ATG  5424
VAL ARG GLY GLY LEU ASP THR LEU ALA ALA ASP ALA GLY PHE VAL MET
        1795                1800                1805

GCA ACA AGC CAG GCC CTG GTA GAC GCC TGT CAG ATG GAA CCG GAG GAA  5472
ALA THR SER GLN ALA LEU VAL ASP ALA CYS GLN MET GLU PRO GLU GLU
    1810                1815                1820

GTA GAG GTC GCA GCC ACA GAG CTA CTG AAA GAG CGA GAG TCC GTC CAG  5520
VAL GLU VAL ALA ALA THR GLU LEU LEU LYS GLU ARG GLU SER VAL GLN
1825                1830                1835                1840

GGC ATG GCC AGT GTC CCG GGA AGC CTG AGC CGC AGG TCC TCC CTG GGC  5568
GLY MET ALA SER VAL PRO GLY SER LEU SER ARG ARG SER SER LEU GLY
            1845                1850          P     1855

AGC CTT GAC CAG GTC CAG GGC TCC CAG GAA ACC CTT ATT CCT CCC AGG  5616
SER LEU ASP GLN VAL GLN GLY SER GLN GLU THR LEU ILE PRO PRO ARG
        1860                1865                1870

CCG TGA TGGCTGTGCA GTGTCCACAT GACCAAGGCG AGGGGGACAG TGCGTGCAGA   5672
PRO

AGCTCAGCCC TGCATGGCAG CCTCCCTCTG TCTCAGCCCT CCTGCTGAGC           5722
TGGGGCGGTC TGGAACCGAC CAGGAAGCCA GGAGCCTCCC CTGGCCAGCA           5772
AGAGGCATGA TTCTAAAGCA TCCAGAAAGG CCTGGTCAGT GCCACTCCCC           5822
AGCAGGACAT TAAAGTCTCT AGGTCTGTGG CAAAAAAAAA AAAAAAAAA            5872
AAAAAAAAAA AAAAAAAAAA AAAAA                                      5897
```

FIGURE 2a

```
5'                                                          AGAAGGGA  -301
GGGCGAGCGT  GGTGTGTGCG  CGCTCGGGCG  CCGGCGGCAC  CGCCGAGGTC  TGTTGGCAAA  -241
AGTCGCCCTT  GATGGCGGCG  GAGGCGAGGC  AGCCGCGGCG  CCGAACAGCC  GACGCGCGCT  -181
AGCGGGGTCC  GCCCGCCCCT  TTCCCAGAGC  CCAGCGCCGC  CGTTCGCCGC  CGCCGCCGCC  -121
CGCCCGCGCG  CCGTTCGCCG  CCGCCGCCGC  CCGCGGGTGG  CAGCGCCGCT  CGGTCCCCGG  -61
CCCCGGGGCC  GGCTGGGGGG  CGGTCGGGGC  GTGTGAGGGG  CTTGCTCCCA  GCTCGCGAAG  -1
```

| | | | | | | | | | | | | | | | | |
|---|---|---|---|---|---|---|---|---|---|---|---|---|---|---|---|---|
| ATG | GCT | GCG | GGC | CGC | CCG | CTG | GCC | TGG | ACG | CTG | ACA | CTT | TGG | CAG | GCG | 48 |
| MET | ALA | ALA | GLY | ARG | PRO | LEU | ALA | TRP | THR | LEU | THR | LEU | TRP | GLN | ALA | |
| | -25 | | | | -20 | | | | -15 | | | | | | | |

| TGG | CTG | ATC | CTG | ATC | GGG | CCC | TCG | TCG | GAG | GAG | CCG | TTC | CCT | TCA | GCC | 96 |
|---|---|---|---|---|---|---|---|---|---|---|---|---|---|---|---|---|
| TRP | LEU | ILE | LEU | ILE | GLY | PRO | SER | SER | GLU | GLU | PRO | PHE | PRO | SER | ALA | |
| -10 | | | | -5 | | | | | -1 |+1 | | | | 5 | | | |

| GTC | ACT | ATC | AAG | TCA | TGG | GTG | GAT | AAG | ATG | CAA | GAA | GAC | CTG | GTC | ACA | 144 |
|---|---|---|---|---|---|---|---|---|---|---|---|---|---|---|---|---|
| VAL | THR | ILE | LYS | SER | TRP | VAL | ASP | LYS | MET | GLN | GLU | ASP | LEU | VAL | THR | |
| | | | 10 | | | | | 15 | | | | | 20 | | | |

| CTG | GCA | AAA | ACA | GCA | AGT | GGA | GTC | AAT | CAG | CTT | GTT | GAT | ATT | TAT | GAG | 192 |
|---|---|---|---|---|---|---|---|---|---|---|---|---|---|---|---|---|
| LEU | ALA | LYS | THR | ALA | SER | GLY | VAL | ASN | GLN | LEU | VAL | ASP | ILE | TYR | GLU | |
| | | 25 | | | | 30 | | | | | | 35 | | | | |

| AAA | TAT | CAA | GAT | TTG | TAT | ACT | GTG | GAA | CCA | AAT | AAT | GCA | CGT | CAG | CTG | 240 |
|---|---|---|---|---|---|---|---|---|---|---|---|---|---|---|---|---|
| LYS | TYR | GLN | ASP | LEU | TYR | THR | VAL | GLU | PRO | ASN | ASN | ALA | ARG | GLN | LEU | |
| 40 | | | | | 45 | | | | | | 50 | | | | | |

| GTG | GAA | ATT | GCA | GCC | AGA | GAC | ATT | GAG | AAG | CTT | CTC | AGC | AAC | AGA | TCT | 288 |
|---|---|---|---|---|---|---|---|---|---|---|---|---|---|---|---|---|
| VAL | GLU | ILE | ALA | ALA | ARG | ASP | ILE | GLU | LYS | LEU | LEU | SER | ASN | ARG | SER | |
| 55 | | | | | 60 | | | | | 65 | | | * | | 70 | |

| AAA | GCC | CTG | GTG | CGC | CTG | GCT | TTG | GAA | GCA | GAG | AAA | GTT | CAA | GCA | GCC | 336 |
|---|---|---|---|---|---|---|---|---|---|---|---|---|---|---|---|---|
| LYS | ALA | LEU | VAL | ARG | LEU | ALA | LEU | GLU | ALA | GLU | LYS | VAL | GLN | ALA | ALA | |
| | | | | 75 | | | | | 80 | | | | | 85 | | |

| CAC | CAA | TGG | AGG | GAA | GAT | TTT | GCA | AGC | AAT | GAA | GTT | GTC | TAC | TAT | AAC | 384 |
|---|---|---|---|---|---|---|---|---|---|---|---|---|---|---|---|---|
| HIS | GLN | TRP | ARG | GLU | ASP | PHE | ALA | SER | ASN | GLU | VAL | VAL | TYR | TYR | ASN | |
| | | | 90 | | | | | 95 | | | | | 100 | | | |

| GCG | AAG | GAT | GAT | CTT | GAT | CCT | GAA | AAA | AAT | GAC | AGT | GAA | CCA | GGC | AGC | 432 |
|---|---|---|---|---|---|---|---|---|---|---|---|---|---|---|---|---|
| ALA | LYS | ASP | ASP | LEU | ASP | PRO | GLU | LYS | ASN | ASP | SER | GLU | PRO | GLY | SER | |
| | | 105 | | | | | 110 | | * | | | 115 | | | | |

| CAG | AGG | ATC | AAA | CCT | GTT | TTC | ATT | GAC | GAT | GCT | AAC | TTT | AGA | AGA | CAA | 480 |
|---|---|---|---|---|---|---|---|---|---|---|---|---|---|---|---|---|
| GLN | ARG | ILE | LYS | PRO | VAL | PHE | ILE | ASP | ASP | ALA | ASN | PHE | ARG | ARG | GLN | |
| | 120 | | | | | 125 | | | | | 130 | | | | | |

| GTA | TCC | TAT | CAG | CAC | GCA | GCT | GTC | CAT | ATC | CCC | ACT | GAC | ATC | TAT | GAA | 528 |
|---|---|---|---|---|---|---|---|---|---|---|---|---|---|---|---|---|
| VAL | SER | TYR | GLN | HIS | ALA | ALA | VAL | HIS | ILE | PRO | THR | ASP | ILE | TYR | GLU | |
| 135 | | | | 140 | | | | | 145 | | | | | 150 | | |

FIGURE 2b

```
GGA TCG ACA ATC GTG TTA AAC GAA CTC AAC TGG ACA AGT GCC TTA GAT    576
GLY SER THR ILE VAL LEU ASN GLU LEU ASN TRP THR SER ALA LEU ASP
            155                 160                 165
                                 *

GAC GTT TTC AAA AAA AAT CGA GAG GAA GAC CCT TCA CTG TTG TGG CAG    624
ASP VAL PHE LYS LYS ASN ARG GLU GLU ASP PRO SER LEU LEU TRP GLN
            170                 175                 180

GTG TTT GGC AGT GCC ACT GGC CTG GCC CGG TAT TAC CCA GCT TCT CCA    672
VAL PHE GLY SER ALA THR GLY LEU ALA ARG TYR TYR PRO ALA SER PRO
            185                 190                 195

TGG GTT GAT AAT AGC CGA ACC CCA AAC AAG ATT GAT CTT TAT GAT GTA    720
TRP VAL ASP ASN SER ARG THR PRO ASN LYS ILE ASP LEU TYR ASP VAL
    200                 205                 210

CGC AGA AGA CCA TGG TAC ATC CAA GGT GCT GCA TCC CCT AAA GAT ATG    768
ARG ARG ARG PRO TRP TYR ILE GLN GLY ALA ALA SER PRO LYS ASP MET
215                 220                 225                 230

CTT ATT CTG GTG GAT GTG AGT GGA AGC GTT AGT GGA CTG ACA CTC AAA    816
LEU ILE LEU VAL ASP VAL SER GLY SER VAL SER GLY LEU THR LEU LYS
            235                 240                 245

CTC ATC CGG ACA TCC GTC TCC GAA ATG TTG GAA ACC CTC TCA GAT GAT    864
LEU ILE ARG THR SER VAL SER GLU MET LEU GLU THR LEU SER ASP ASP
            250                 255                 260

GAT TTT GTG AAC GTG GCT TCA TTT AAC AGC AAT GCT CAG GAT GTA AGC    912
ASP PHE VAL ASN VAL ALA SER PHE ASN SER ASN ALA GLN ASP VAL SER
            265                 270                 275

TGC TTT CAG CAC CTT GTC CAA GCA AAT GTA AGA AAT AAG AAA GTG TTG    960
CYS PHE GLN HIS LEU VAL GLN ALA ASN VAL ARG ASN LYS LYS VAL LEU
            280                 285                 290

AAA GAT GCA GTG AAT AAT ATC ACA GCA AAA GGA ATC ACA GAT TAT AAG   1008
LYS ASP ALA VAL ASN ASN ILE THR ALA LYS GLY ILE THR ASP TYR LYS
295                 300                 305                 310
                     *

AAG GGC TTT AGT TTT GCT TTT GAG CAG CTG CTT AAT TAT AAT GTA TCC   1056
LYS GLY PHE SER PHE ALA PHE GLU GLN LEU LEU ASN TYR ASN VAL SER
            315                 320              *  325

AGA GCC AAC TGC AAT AAG ATT ATC ATG TTG TTC ACG GAC GGA GGA GAA   1104
ARG ALA ASN CYS ASN LYS ILE ILE MET LEU PHE THR ASP GLY GLY GLU
            330                 335                 340
```

FIGURE 2c

| | | | | | | | | | | | | | | | | |
|---|---|---|---|---|---|---|---|---|---|---|---|---|---|---|---|---|
| GAG | AGA | GCC | CAG | GAG | ATA | TTT | GCC | AAA | TAC | AAT | AAA | GAC | AAG | AAA | GTA | 1152 |
| GLU | ARG | ALA | GLN | GLU | ILE | PHE | ALA | LYS | TYR | ASN | LYS | ASP | LYS | LYS | VAL | |
| | | 345 | | | | | 350 | | | | | 355 | | | | |
| CGT | GTA | TTC | ACA | TTC | TCA | GTT | GGC | CAA | CAT | AAT | TAC | GAC | AGA | GGA | CCT | 1200 |
| ARG | VAL | PHE | THR | PHE | SER | VAL | GLY | GLN | HIS | ASN | TYR | ASP | ARG | GLY | PRO | |
| | | 360 | | | | | 365 | | | | | 370 | | | | |
| ATT | CAG | TGG | ATG | GCT | TGC | GAA | AAT | AAA | GGT | TAT | TAT | TAT | GAA | ATT | CCA | 1248 |
| ILE | GLN | TRP | MET | ALA | CYS | GLU | ASN | LYS | GLY | TYR | TYR | TYR | GLU | ILE | PRO | |
| 375 | | | | | 380 | | | | | 385 | | | | | 390 | |
| TCC | ATT | GGA | GCC | ATA | AGA | ATT | AAT | ACT | CAG | GAA | TAC | CTA | GAT | GTT | CTG | 1296 |
| SER | ILE | GLY | ALA | ILE | ARG | ILE | ASN | THR | GLN | GLU | TYR | LEU | ASP | VAL | LEU | |
| | | | | 395 | | | | | 400 | | | | | 405 | | |
| GGA | AGA | CCG | ATG | GTT | TTA | GCA | GGA | GAC | AAA | GCT | AAG | CAA | GTC | CAA | TGG | 1344 |
| GLY | ARG | PRO | MET | VAL | LEU | ALA | GLY | ASP | LYS | ALA | LYS | GLN | VAL | GLN | TRP | |
| | | | 410 | | | | | 415 | | | | | 420 | | | |
| ACA | AAT | GTG | TAC | CTG | GAT | GCA | CTG | GAA | CTG | GGA | CTT | GTC | ATT | ACT | GGA | 1392 |
| THR | ASN | VAL | TYR | LEU | ASP | ALA | LEU | GLU | LEU | GLY | LEU | VAL | ILE | THR | GLY | |
| | | | 425 | | | | | 430 | | | | | 435 | | | |
| ACT | CTT | CCG | GTC | TTC | AAC | ATA | ACT | GGC | CAA | TTT | GAA | AAT | AAG | ACA | AAC | 1440 |
| THR | LEU | PRO | VAL | PHE | ASN | ILE | THR | GLY | GLN | PHE | GLU | ASN | LYS | THR | ASN | |
| | | 440 | | | * | 445 | | | | | 450 | * | | | | |
| TTA | AAG | AAC | CAG | CTG | ATT | CTT | GGA | GTG | ATG | GGA | GTT | GAT | GTG | TCT | TTG | 1488 |
| LEU | LYS | ASN | GLN | LEU | ILE | LEU | GLY | VAL | MET | GLY | VAL | ASP | VAL | SER | LEU | |
| 455 | | | | | 460 | | | | | 465 | | | | | 470 | |
| GAA | GAT | ATT | AAA | AGA | CTG | ACA | CCA | CGT | TTT | ACA | CTC | TGC | CCC | AAT | GGC | 1536 |
| GLU | ASP | ILE | LYS | ARG | LEU | THR | PRO | ARG | PHE | THR | LEU | CYS | PRO | ASN | GLY | |
| | | | | 475 | | | | | 480 | | | | | 485 | | |
| TAC | TAT | TTT | GCA | ATT | GAT | CCT | AAT | GGT | TAT | GTG | TTA | TTA | CAT | CCA | AAT | 1584 |
| TYR | TYR | PHE | ALA | ILE | ASP | PRO | ASN | GLY | TYR | VAL | LEU | LEU | HIS | PRO | ASN | |
| | | | 490 | | | | | 495 | | | | | 500 | | | |
| CTT | CAG | CCA | AAG | CCT | ATT | GGT | GTA | GGT | ATA | CCA | ACA | ATT | AAT | TTG | AGA | 1632 |
| LEU | GLN | PRO | LYS | PRO | ILE | GLY | VAL | GLY | ILE | PRO | THR | ILE | ASN | LEU | ARG | |
| | | 505 | | | | | 510 | | | | | 515 | | | | |
| AAA | AGG | AGA | CCC | AAT | GTT | CAG | AAC | CCC | AAA | TCT | CAG | GAG | CCA | GTG | ACA | 1680 |
| LYS | ARG | ARG | PRO | ASN | VAL | GLN | ASN | PRO | LYS | SER | GLN | GLU | PRO | VAL | THR | |
| | | 520 | | | | | 525 | | | | | 530 | | | | |
| TTG | GAT | TTC | CTC | GAT | GCA | GAG | TTG | GAG | AAT | GAC | ATT | AAA | GTG | GAG | ATT | 1728 |
| LEU | ASP | PHE | LEU | ASP | ALA | GLU | LEU | GLU | ASN | ASP | ILE | LYS | VAL | GLU | ILE | |
| 535 | | | | | 540 | | | | | 545 | | | | | 550 | |

FIGURE 2d

```
CGA AAT AAA ATG ATC GAT GGA GAA AGT GGA GAA AAA ACA TTC AGA ACT    1766
ARG ASN LYS MET ILE ASP GLY GLU SER GLY GLU LYS THR PHE ARG THR
            555             560                 565

CTG GTT AAA TCT CAA GAT GAG AGA TAT ATT GAC AAA GGA AAC AGG ACA    1824
LEU VAL LYS SER GLN ASP GLU ARG TYR ILE ASP LYS GLY ASN ARG THR
            570             575                 *
                                                580

TAC ACG TGG ACT CCT GTC AAC GGC ACA GAT TAT AGC AGT TTG GCC TTG    1872
TYR THR TRP THR PRO VAL ASN GLY THR ASP TYR SER SER LEU ALA LEU
            585          *  590                 595

GTA TTA CCA ACC TAC AGT TTT TAC TAT ATA AAA GCC AAA ATA GAA GAG    1920
VAL LEU PRO THR TYR SER PHE TYR TYR ILE LYS ALA LYS ILE GLU GLU
            600             605                 610

ACA ATA ACT CAG GCC AGA TAT TCA GAA ACA CTG AAA CCG GAT AAT TTT    1968
THR ILE THR GLN ALA ARG TYR SER GLU THR LEU LYS PRO ASP ASN PHE
615             620             625                 630

GAA GAA TCT GGC TAC ACA TTC CTA GCA CCA AGA GAT TAC TGC AGT GAC    2016
GLU GLU SER GLY TYR THR PHE LEU ALA PRO ARG ASP TYR CYS SER ASP
                635             640                 645

CTT AAA CCT TCA GAT AAT AAC ACT GAA TTT CTT TTA AAT TTC AAT GAG    2064
LEU LYS PRO SER ASP ASN ASN THR GLU PHE LEU LEU ASN PHE ASN GLU
            650  *              655                 660

TTT ATT GAT AGA AAA ACT CCA AAC AAC CCA TCC TGT AAT ACA GAC TTG    2112
PHE ILE ASP ARG LYS THR PRO ASN ASN PRO SER CYS ASN THR ASP LEU
            665             670  *              675

ATT AAT AGA GTC TTG CTG GAT GCA GGC TTT ACA AAT GAA CTT GTT CAA    2160
ILE ASN ARG VAL LEU LEU ASP ALA GLY PHE THR ASN GLU LEU VAL GLN
            680             685                 690

AAT TAC TGG AGT AAG CAG AAG AAT ATC AAG GGA GTG AAA GCA CGG TTT    2208
ASN TYR TRP SER LYS GLN LYS ASN ILE LYS GLY VAL LYS ALA ARG PHE
695             700             705                 710

GTT GTG ACT GAT GGT GGG ATT ACC AGA GTT TAT CCC AAA GAG GCT GGA    2256
VAL VAL THR ASP GLY GLY ILE THR ARG VAL TYR PRO LYS GLU ALA GLY
            715             720                 725

GAA AAT TGG CAG GAA AAC CCA GAG ACA TAT GAA GAC AGC TTC TAT AAA    2304
GLU ASN TRP GLN GLU ASN PRO GLU THR TYR GLU ASP SER PHE TYR LYS
            730             735                 740

AGG AGC CTC GAT AAT GAT AAC TAC GTT TTC ACT GCT CCC TAC TTT AAC    2352
ARG SER LEU ASP ASN ASP ASN TYR VAL PHE THR ALA PRO TYR PHE ASN
            745             750                 755          *
```

FIGURE 2e

```
AAA AGT GGA CCT GGG GCC TAT GAG TCA GGC ATT ATG GTA AGC AAA GCT      2400
LYS SER GLY PRO GLY ALA TYR GLU SER GLY ILE MET VAL SER LYS ALA
    760             765                 770

GTA GAA ATA TAT ATC CAA GGA AAA CTT CTT AAA CCT GCA GTT GTT GGA      2448
VAL GLU ILE TYR ILE GLN GLY LYS LEU LEU LYS PRO ALA VAL VAL GLY
775             780                 785                 790

ATT AAA ATT GAT GTA AAT TCT TGG ATA GAG AAT TTC ACC AAA ACT TCA      2496
ILE LYS ILE ASP VAL ASN SER TRP ILE GLU ASN PHE THR LYS THR SER
                795                 800  *              805

ATC AGG GAT CCG TGT GCT GGT CCA GTT TGT GAC TGC AAA CGA AAC AGT      2544
ILE ARG ASP PRO CYS ALA GLY PRO VAL CYS ASP CYS LYS ARG ASN SER
            810                 815                 820   P

GAT GTA ATG GAT TGT GTG ATT CTA GAT GAC GGT GGG TTT CTT TTG ATG      2592
ASP VAL MET ASP CYS VAL ILE LEU ASP ASP GLY GLY PHE LEU LEU MET
        825                 830                 835

GCC AAC CAT GAT GAT TAT ACC AAT CAG ATT GGA AGA TTC TTT GGA GAG      2640
ALA ASN HIS ASP ASP TYR THR ASN GLN ILE GLY ARG PHE PHE GLY GLU
    840                 845                 850

ATT GAT CCA AGC TTG ATG AGA CAC CTG GTC AAT ATA TCA GTT TAT GCC      2688
ILE ASP PRO SER LEU MET ARG HIS LEU VAL ASN ILE SER VAL TYR ALA
855             860                 865                 870
                                         *

TTT AAC AAA TCT TAT GAT TAT CAG TCG GTG TGT GAA CCT GGT GCT GCG      2736
PHE ASN LYS SER TYR ASP TYR GLN SER VAL CYS GLU PRO GLY ALA ALA
     *          875                 880                 885

CCA AAG CAG GGA GCA GGG CAC CGC TCG GCT TAT GTG CCA TCA ATA GCA      2784
PRO LYS GLN GLY ALA GLY HIS ARG SER ALA TYR VAL PRO SER ILE ALA
            890                 895                 900

GAC ATA CTG CAG ATT GGA TGG TGG GCC ACT GCT GCT GCC TGG TCT ATT      2832
ASP ILE LEU GLN ILE GLY TRP TRP ALA THR ALA ALA ALA TRP SER ILE
        905                 910                 915

CTT CAG CAG TTT CTG TTG AGT TTG ACT TTT CCA CGG CTC CTT GAG GCA      2880
LEU GLN GLN PHE LEU LEU SER LEU THR PHE PRO ARG LEU LEU GLU ALA
    920                 925                 930

GCT GAT ATG GAG GAT GAC GAC TTC ACT GCC TCC ATG TCA AAG CAG AGC      2928
ALA ASP MET GLU ASP ASP ASP PHE THR ALA SER MET SER LYS GLN SER
935             940                 945                 950
```

FIGURE 2f

```
TGC ATC ACT GAG CAA ACC CAG TAT TTC TTC GAT AAT GAC AGC AAA TCG   2976
CYS ILE THR GLU GLN THR GLN TYR PHE PHE ASP ASN ASP SER LYS SER
            955                 960   *           965

TTC AGT GGG GTA TTA GAC TGT GGG AAT TGT TCC AGA ATC TTT CAT GTA   3024
PHE SER GLY VAL LEU ASP CYS GLY ASN CYS SER ARG ILE PHE HIS VAL
            970             975                 980
                             *
GAA AAG CTC ATG AAC ACC AAT TTA ATA TTC ATA ATG GTA GAG AGC AAG   3072
GLU LYS LEU MET ASN THR ASN LEU ILE PHE ILE MET VAL GLU SER LYS
            985             990                 995

GGG ACA TGT CCC TGT GAC ACA CGG CTG CTC ATA CAA GCA GAG CAA ACT   3120
GLY THR CYS PRO CYS ASP THR ARG LEU LEU ILE GLN ALA GLU GLN THR
        1000            1005            1010

TCT GAT GGA CCA GAT CCT TGT GAT ATG GTT AAG CAA CCC AGA TAT CGA   3168
SER ASP GLY PRO ASP PRO CYS ASP MET VAL LYS GLN PRO ARG TYR ARG
1015             1020             1025                 1030

AAA GGG CCA GAT GTC TGC TTT GAC AAC AAT GTC CTG GAG GAT TAT ACT   3218
LYS GLY PRO ASP VAL CYS PHE ASP ASN ASN VAL LEU GLU ASP TYR THR
                1035             1040                1045

GAC TGC GGT GGG GTC TCT GGA TTA AAT|CCT TCC CTG TGG TCC ATC ATC   3264
ASP CYS GLY GLY VAL SER GLY LEU ASN|PRO SER LEU TRP SER ILE ILE
            1050             1055                1060
                              *
GGG ATA CAG TTT GTA CTG CTT TGG CTG GTT TCT GGC AGC|AGA CAC TGC   3312
GLY ILE GLN PHE VAL LEU LEU TRP LEU VAL SER GLY SER|ARG HIS CYS
            1065             1070            1075

CTG TTA TGA CCTTCTAAAA CCAAATCTCC ATAATTAAAC TCCAGACCCT           3361
LEU LEU
    1080

GCCACAACAT GATCCCTCCG TTATGTTAAA GTAGGGTCAA CTGTTAAATC            3411
AGAACATTAG CTGGGCCTCT GCCATGGCAG AGCCCTAAGG CGCAGACTCA            3461
TCAGGCACCC ACTGGCTGCA TGTCAGGGTG TCC...... 3'                     3494
```

FIGURE 3a

```
                                    .             .              .              .              .
        Human Neuronalα2
........................GGGCGGGGGAGGGGGATTGATCTTC    25
Rabbit Skeletal Muscleα2 ||||| | |||||| |      |
CCCGGGGCCGGCTGGGGGGCGGTCGGGGCGTGTGAGGGGCTTGCTCCCAG   299
           Start    .             .              .              .              .
GATCGCAAGATGGCTGCTGGCTGCCTGCTGGCCTTGACTCTGACACTTTT    75
||||||||||||| ||| ||| |||||||| ||| |||||||||||
CTCGCGAAGATGGCTGCGGGCCGCCCGCTGGCCTGGACGCTGACACTTTG   349

.             .              .              .              .
CCAATCTT......TGCTCATCGGCCCCTCGTCGGAGGAGCCGTTCCCTT   119
|| | |       | || |||||| |||||||||||||||||||||
Gcaggcgtggctgatcctgatcgggccctcgtcggaggagccgttccctt   399

.             .              .              .              .
CGGCCGTCACTATCAAATCATGGTGGATAAGATGCAAGAAGACCTTGTC    169
| ||||||||||||| |||||||||||||||||||||||||||| |||
cagccgtcactatcaagtcatgggtggataagatgcaagaagacctggtc   449

.             .              .              .              .
ACACTGGCAAAAACAGCAAGTGGAGTCAATCAGCTTGTTGATATTTATGA   219
|||||||||||||||||||||||||||||||||||||||||||||||||
acactggcaaaaacagcaagtggagtcaatcagcttgttgatatttatga   499

.             .              .              .              .
GAAATATCAAGATTTGTATACTGTGGAACCAAATAATGCACGCCAGCTGG   269
|||||||||||||||||||||||||||||||||||||||||| |||||||
gaaatatcaagatttgtatactgtggaaccaaataatgcacgtcagctgg   549

.             .              .              .              .
TAGAAATTGCAGCCAGGGATATTGAGAAACTTCTGAGCAACAGATCTAAA   319
| |||||||||||||| || ||||||||| ||||| |||||||||||||
tggaaattgcagccagagacattgagaagcttctcagcaACAGATCTAAA   599

.             .              .              .              .
GCCCTGGTGAGCCTGGCATTGGAAGCGGAGAAAGTTCAAGCAGCTCACCA   369
|||||||| ||||||| |||||||| |||||||||||||||||| |||||
GCCCTGGTGCGCCTGGCTTTGGAAGCAGAGAAAGTTCAAGCAGCCCACCA   649
```

FIGURE 3b

```
GTGGAGAGAAGATTTTGCAAGCAATGAAGTTGTCTACTACAATGCAAAGG  419
|||||  ||||||||||||||||||||||||||||||||| || || ||||
ATGGAGGGAAGATTTTGCAAGCAATGAAGTTGTCTACTATAACGCGAAGG  699

ATGATCTCGATCCTGAGAAAAATGACAGTGAGCCAGGCAGCCAGAGGATA  469
|||||||  |||||||| ||||||||||||| ||||||||||||||||||
ATGATCTTGATCCTGAAAAAAATGACAGTGAACCAGGCAGCCAGAGGATC  749

AAACCTGTTTTCATTGAAGATGCTAATTTTGGACGACAAATATCTTATCA  519
||||||||||||||||| ||||||| ||| || ||||| |||| |||||
AAACCTGTTTTCATTGACGATGCTAACTTTAGAAGACAAGTATCCTATCA  799

GCACGCAGCAGTCCATATTCCTACTGACATCTATGAGGGCTCAACAATTG  569
|||||||||| ||||||  || ||||||||||||||| || || |||||  |
GCACGCAGCTGTCCATATCCCCACTGACATCTATGAAGGATCGACAATCG  849

TGTTAAATGAACTCAACTGGACAAGTGCCTTAGATGAAGTTTTCAAAAAG  619
|||||||  |||||||||||||||||||||||||||| |||||||||||
TGTTAAACGAACTCAACTGGACAAGTGCCTTAGATGACGTTTTCAAAAAA  899

AATCGCGAGGAAGACCCTTCATTATTGTGGCAGGTTTTTGGCAGTGCCAC  669
|||||  |||||||||||||| |  |||||||||| |  ||||||||||||
AATCGAGAGGAAGACCCTTCACTGTTGTGGCAGGTGTTTGGCAGTGCCAC  949

TGGCCTAGCTCGATATTATCCAGCTTCACCATGGGTTGATAATGGTAGAA  719
|||||| || || |||| |||||||||||||||||||||||||| | |||
TGGCCTGGCCCGGTATTACCCAGCTTCTCCATGGGTTGATAATAGCCGAA  999

CTCCAAATATGATTGACCTTTATGATGTACGCAGAAGACCATGGTACATC  769
| ||||| | ||||||  |||||||||||||||||||||||||||||||
CCCCAAACAAGATTGATCTTTATGATGTACGCAGAAGACCATGGTACATC  1049

CAAGGAGCTGCATCTCCTAAAGACATGCTTATTCTGGTGGATGTGAGTGG  819
||||| ||||||||  ||||||| ||||||||||||||||||||||||||
CAAGGTGCTGCATCCCCTAAAGATATGCTTATTCTGGTGGATGTGAGTGG  1099
```

FIGURE 3c

```
AAGTGTTAGTGGATTGACACTTAAACTGATCCGAACATCTGTCTCCGAAA   869
||| |||||||||| ||||||| ||||| ||||| ||||| |||||||||||
AAGCGTTAGTGGACTGACACTCAAACTCATCCGGACATCCGTCTCCGAAA  1149

TGTTAGAAACCCTCTCAGATGATGATTTCGTGAATGTAGCTTCATTTAAC   919
|||| |||||||||||||||||||||||| ||||| || ||||||||||
TGTTGGAAACCCTCTCAGATGATGATTTTGTGAACGTGGCTTCATTTAAC  1199

AGCAATGCTCAGGATGTAAGCTGTTTTCAGCACCTTGTCCAAGCAAATGT   969
|||||||||||||||||||||| ||||||||||||||||||||||||||
AGCAATGCTCAGGATGTAAGCTGCTTTCAGCACCTTGTCCAAGCAAATGT  1249

AAGAAATAAAAAGTGTTGAAAGACGCGGTGAATAATATCACAGCCAAAG  1019
|||||||| ||||||||||||||| || ||||||||||||||||| ||||
AAGAAATAAGAAAGTGTTGAAAGATGCAGTGAATAATATCACAGCAAAAG  1299

GAATTACAGATTATAAGAAGGGCTTTAGTTTTGCTTTTGAACAGCTGCTT  1069
|||| ||||||||||||||||||||||||||||||||||| |||||||||
GAATCACAGATTATAAGAAGGGCTTTAGTTTTGCTTTTGAGCAGCTGCTT  1349

AATTATAATGTTTCCAGAGCAAACTGCAATAAGATTATTATGCTATTCAC  1119
||||||||||| |||||| |||||||||||||||||| | | |||||
AATTATAATGTATCCAGAGCCAACTGCAATAAGATTATCATGTTGTTCAC  1399

GGA...TGGAGAAGAGAGAGCCCAGGAGATATTTAACAAATACAATAAAG  1166
|||    |||||||||||||||||||||||||||| ||||||||||||||
GGACGGAGGAGAAGAGAGAGCCCAGGAGATATTTGCCAAATACAATAAAG  1449

ATAAAAAACTACCTGTATTCACCTTCTCAGTTGGTCAACACAATTATGAC  1216
| || ||| ||| ||||||||| ||||||||||| ||||| ||||| |||
ACAAGAAAGTACGTGTATTCACATTCTCAGTTGGCCAACATAATTACGAC  1499
```

FIGURE 3d

```
AGAGGACCTATTCAGTGGATGGCCTGTGAAAACAAAGGTTATTATTATGA    1266
|||||||||||||||||||||||||| || |||||| |||||||||||||||
AGAGGACCTATTCAGTGGATGGCTTGCGAAAATAAAGGTTATTATTATGA    1549

AATTCCTTCCATTGGTGCAATAAGAATCAATACTCAGGAATATTTGGATG    1316
||||||  ||||||||  || ||||||||| ||||||||||||  | ||||
AATTCCATCCATTGGAGCCATAAGAATTAATACTCAGGAATACCTAGATG    1599

TTTTGGGAAGACCAATGGTTTTAGCAGGAGACAAAGCTAAGCAAGTCCAA    1366
|| |||||||||||| ||||||||||||||||||||||||||||||||||
TTCTGGGAAGACCGATGGTTTTAGCAGGAGACAAAGCTAAGCAAGTCCAA    1649

TGGACAAATGTGTACCTGGATGCATTGGAACTGGGACTTGTCATTACTGG    1416
|||||||||||||||||||||||| |||||||||||||||||||||||||
TGGACAAATGTGTACCTGGATGCACTGGAACTGGGACTTGTCATTACTGG    1699

AACTCTTCCGGTCTTCAACATAACCGGCCAATTTGAAAATAAGACAAACT    1466
||||||||||||||||||||||| ||||||||||||||||||||||||||
AACTCTTCCGGTCTTCAACATAACTGGCCAATTTGAAAATAAGACAAACT    1749

TAAAGAACCAGCTGATTCTTGGTGTGATGGGAGTAGATGTGTCTTTGGAA    1516
|||||||||||||||||||||| |||||||||||| ||||||||||||||
TAAAGAACCAGCTGATTCTTGGAGTGATGGGAGTTGATGTGTCTTTGGAA    1799

GATATTAAAAGACTGACACCACGTTTTACACTGTGCCCCAATGG......    1560
|||||||||||||||||||||||||||||||| |||||||||||
GATATTAAAAGACTGACACCACGTTTTACACTCTGCCCCAATGGCTACTA    1849
```

CALCIUM CHANNEL COMPOSITIONS AND METHODS

This application continuation of U.S. application Ser. No. 08/314,083, filed Sep. 28, 1994, now U.S. Pat. No. 5,686,241, which is a divisional of U.S. application Ser. No. 07/914,231, filed Jul. 13, 1992 now U.S. Pat. No. 5,407,820, which is a continuation of U.S. application Ser. No. 07/603,751, filed Nov. 8, 1990, now abandoned, which is a continuation-in-part of U.S. application Ser. No. 07/176,899, filed Apr. 4, 1988, now abandoned. U.S. application Ser. No. 07/603,751 is International PCT Application PCT/US89/01408, filed Apr. 4, 1989.

TECHNICAL FIELD

The present invention relates to molecular biology and pharmacology.

More particularly, the invention relates to calcium channel compositions and methods of making and using same.

BACKGROUND OF THE INVENTION

Calcium channels are membrane-spanning, multisubunit proteins that allow controlled entry of $Ca^{+2}$ ions into cells from the extracellular fluid. All cells throughout the animal kingdom, and at least some bacterial, fungal and plant cells, possess one or more types of calcium channel.

The most common type of calcium channel is voltage-dependent. In a voltage-dependent channel, the "opening," to allow an influx of $Ca^{+2}$ ions into the cells to begin, requires a depolarization to a certain level of the potential difference between the inside of the cell bearing the channel and the extracellular medium bathing the cell and the rate of influx of $Ca^{+2}$ into the cell depends on this potential difference. All "excitable" cells in animals, such as neurons of the central nervous systems, peripheral nerve cells, and muscle cells, including those of skeletal muscles, cardiac muscles, and venous and arterial smooth muscles, have voltage-dependent calcium channels.

Calcium channels are physiologically important because the channels have a central role in regulating intracellular $Ca^{+2}$ levels and these levels are important for cell viability and function. Thus, intracellular $Ca^{+2}$ concentrations are implicated in a number of vital processes in animals, such as neurotransmitter release, muscle contraction, pacemaker activity, and secretion of hormones and other substances.

A number of compounds useful in treating various diseases in animals, including humans, are thought to exert their beneficial effects by modulating functions of voltage-dependent calcium channels. Many of these compounds bind to calcium channels and block, or reduce the rate of, influx of $Ca^{+2}$ into cells in response to depolarization of the inside and outside of the cells.

An understanding of the pharmacology of compounds that interact with calcium channels, and the ability to rationally design compounds that will interact with calcium channels to have desired therapeutic effects, have been hampered by a lack of understanding of the structure of channel subunits and the genes that code for them. Thus, it has not been possible to obtain the large amounts of highly purified channel subunits that are required to understand, at the molecular level, the nature of the subunits and their interactions with one another, with the cell membranes across which the channels allow $Ca^{+2}$ ions to pass, with $Ca^{+2}$ and other ions, and with low molecular weight compounds that affect channel function. For example, with the availability of large amounts of purified calcium channel subunits, functional channels could be prepared and used to screen the effects of compounds on channel function, thereby providing a basis for the design of therapeutic agents which affect the calcium channel, or various combinations of channel subunits could be crystallized and have their structures determined to high resolution employing X-ray or neutron diffraction techniques, providing yet another basis for rational design of therapeutic agents that affect channel function.

Certain diseases, such as Lambert-Eaton Syndrome, involve autoimmune interactions with calcium channels. The ready availability of calcium channel subunits would make possible immunoassays for the diagnosis of such diseases and an understanding of them at the molecular level that could lead to effective methods for treating them.

The lack of information on genes that code for calcium channel subunits has prevented the understanding of the molecular properties of the mature calcium channel subunits and their precursor proteins (i.e., the mature subunits with signal peptides appended to the amino-terminus) and the regulation of expression of calcium channel subunits. An understanding of these properties, and of how expression of calcium channel subunit genes is regulated, may provide the basis for designing therapeutic agents which have beneficial effects through affecting calcium channel function or concentration. Furthermore, the availability of sequences of genes coding for calcium channel subunits would make possible the diagnosis of defects, which might underlie a number of diseases, in genes coding for such subunits.

The availability of a DNA with the sequence of a segment, of at least about 12, and more preferably at least about 30, nucleotides of a cDNA encoding a subunit of a calcium channel from the cells of a tissue of an animal would make possible the isolation and cloning of cDNA's, and possibly genomic DNA'S, coding for the corresponding subunit of different calcium channels from the same or different tissues and animals of the same or different species. The availability of the sequences of numerous full-length cDNA's coding for corresponding subunits of calcium channels from a variety of tissues and animal species would contribute to elucidating structure-function relationships in the subunits and this knowledge, in turn, would be useful in the design of therapeutic agents whose activities are exerted through binding to calcium channels.

Voltage-dependent calcium channels are thought to consist of two large subunits, of between about 130 and about 200 kilodaltons ("kD") in molecular weight, and a number (generally thought to be one or three) of different smaller subunits, of less than about 60 kD in molecular weight. At least one of the larger subunits and possibly some of the smaller are glycosylated. Some of the subunits are capable of being phosphorylated. There is confusion in the art concerning the naming of the various subunits of voltage-dependent calcium channels.

The two large subunits of voltage-dependent calcium channels are designated herein the "$(alpha)_1$-subunit" and the "$(alpha)_2$-subunit".

The $(alpha)_1$-subunit is not detectably changed in molecular weight when treated with dithiothreitol ("DTT") or with enzymes which catalyze removal of N-linked sugar groups from glycosylated proteins. The $(alpha)_1$-subunit has a molecular weight of about 150 to about 170 kD when analyzed by sodium dodecylsulfate ("SDS")-polyacrylamide gel electrophresis ("PAGE") after isolation from mammalian muscle tissue and has specific binding sites for various 1,4-dihydropyridines ("DHPs") and phenylalkylamines.

The (alpha)$_2$-subunit is somewhat less well characterized than the (alpha)$_1$-subunit. The molecular weight of the (alpha)$_2$-subunit is at least about 130–150 kD, as determined by SDS-PAGE analysis in the presence of DTT after isolation from mammalian muscle tissue. However, in SDS-PAGE under non-reducing conditions (in the presence of N-ethylmaleimide), the (alpha)$_2$-subunit migrates with a band of about 160–190 kD. It is not known in the art whether the smaller fragment (of about 30 kD), which appears to be released upon reduction, is the product of a gene different from the gene which encodes the 130–150 kD fragment (and, consequently, the two fragments are different subunits of the calcium channel) or whether both fragments are products of the same gene (and, consequently, the (alpha)$_2$-subunit is about 160–190 kD and is split into (at least) two fragments upon reduction). There is evidence that the (alpha)$_2$-subunit, whatever its size, and the corresponding fragment produced under reducing conditions, whether part of the (alpha)$_2$-subunit or not, are glycosylated with at least N-linked sugars and do not have specified binding sites for 1,4-dihydropyridines and phenylalkylamines that are known to bind to the (alpha)$_1$-subunit.

Reference herein to the precursor of an (alpha)$_1$-subunit means the protein with the amino acid sequence corresponding to the sequence of the full-length mRNA which, upon translation, results, ultimately, in (alpha)$_1$-subunit resident as part of a calcium channel in a cell membrane. The precursor protein is converted by various processing steps into the (alpha)$_1$-subunit. The details of the processing between the precursor and the mature (alpha)$_1$-subunit are not clear, but the processing possibly involves phosphorylation and also cleavage of the primary translation product to yield the mature (alpha)$_1$-subunit of the calcium channel.

Similarly, reference herein to the precursor of an (alpha)$_2$-subunit means the protein with the amino acid sequence corresponding to the sequence of the full-length mRNA which, upon translation, results, ultimately, in (alpha)$_2$-subunit resident as part of a calcium channel in a cell membrane. The precursor protein is converted by various processing steps into the (alpha)$_2$-subunit. As with the (alpha)$_1$-subunit, the details of the processing between the precursor and the mature (alpha)$_2$-subunit are not clear, but the processing presumably involves at least removal of a leader sequence (i.e., a signal peptide), glycosylation, and, possibly, cleavage to yield what are now thought to be other subunits of the calcium channel.

The cDNA and corresponding amino acid sequence of the (alpha)$_1$-subunit precursor of a rabbit back skeletal muscle calcium channel has been reported. Tanabe et al., Nature 328, 313–318 (1987).

Calcium channel activity, measured electrophysiologically by voltage-clamp techniques, has been induced in *Xenopus laevis* oocytes when total mRNA isolated from mammalian brain and cardiac muscle is injected into the oocytes. Also, it has been reported that calcium channel-containing preparations, when reconstituted into lipid bilayers, confer voltage-dependent calcium channel activity on the bilayers.

However, there is no evidence that the (alpha)$_1$-subunit alone or the (alpha)$_2$-subunit alone provides a functional calcium channel in oocytes, lipid bilayers or any other situation. It has been recently reported by Hofmann, et al., Trends in Pharmacolog. Sci. 8, 393–398 (1987) that mRNA prepared using the cDNA of (alpha)$_1$-subunit obtained by Tanabe, et al. was unable to induce calcium channel activity in *Xenopus laevis* oocytes.

BRIEF DESCRIPTION OF THE FIGURES

FIG. 1 sets forth the nucleotide sequence of the cDNA encoding the (alpha)$_1$-subunit of the rabbit skeletal calcium channel and the amino acid sequence encoded by the 5,619 nucleotide open reading frame, which encodes a sequence of 1,873 amino acids. The 3' non-coding sequence of the cDNA is 234 nucleotides in length, excluding the poly (dA) tract, and contains a consensus polyadenylation signal ATTAAA (nucleotides 5832–5837) 17 nucleotides upstream from the poly (dA) tract.

FIG. 2 sets forth the 3,802 nucleotide and amino acid sequences of the rabbit skeletal calcium channel (alpha)$_2$-subunit. The figure includes the nucleotides of the cDNA that encodes the (alpha)$_2$-subunit precursor, including the 308 nucleotides of the 5' untranslated sequence, the 3,318 nucleotide open reading frame and 176 nucleotides of 3' untranslated sequence. The signal peptide of the (alpha)$_2$-subunit is shown as the first 26 negatively numbered amino acids.

FIG. 3 compares the sequences of the DNA encoding the human neuronal (alpha)$_2$-subunit with that encoding the rabbit skeletal (alpha)$_2$-subunit.

The boxes in the figures enclose transmembrane regions. The symbol, P, denotes a phosphorylation site and the symbol, *, indicates a N-glycosylation site.

DETAILED DESCRIPTION OF THE INVENTION

In short, we have discovered a cDNA which codes for the (alpha)$_1$-subunit of an animal calcium channel (see FIG. 1) and a cDNA which codes for the (alpha)$_2$-subunit of an animal calcium channel (see FIG. 2 and Example 4).

Thus in one of its aspects, the invention is a DNA which comprises a cDNA which codes for the (alpha)$_2$-subunit of an animal calcium channel, and the RNA, coding for such a subunit, made upon transcription of such a DNA according to the invention.

In another of its aspects, the invention is a substantially pure (alpha)$_2$-subunit of an animal calcium channel.

By a "substantially pure" subunit or protein is meant a subunit or protein that is sufficiently free of other polypeptide contaminants to be considered homogeneous by SDS-PAGE or to be unambiguously sequenced.

In another of its aspects, the invention entails an eukaryotic cell with an heterologous calcium channel, said cell made by a process comprising administering to said cell a first composition, which consists essentially of a first RNA which is translatable in said cell into the precursor of the (alpha)$_1$-subunit of a calcium channel of an animal of a first species, and a second composition which consists essentially of a second RNA which is translatable in said cell into the precursor of the (alpha)$_2$-subunit of a calcium channel of an animal of a second species, said first and second species being the same or different, provided that at least one of said precursor of said (alpha)$_1$-subunit and said precursor of said (alpha)$_2$-subunit is foreign to said cell. Preferred cells for this purpose are *Xenopus laevis* oocytes.

In another of its aspects, the invention entails a method for assaying a compound for calcium channel agonist or antagonist activity which comprises electrophysiologically measuring the calcium channel activity of a cell described in the immediately preceeding paragraph when such cell is exposed to a solution of the compound being tested for such activity. For similar methods applied with *Xenopus laevis* oocytes and acetylcholine receptors, see e.g., Mishina et al.

Nature 313, 364 (1985) and, with such oocytes and sodium channels, see Noda et al., Nature 322, 826–828 (1986).

In a further of its aspects, the invention is an eukaryotic cell containing a DNA which comprises a cDNA which can be expressed to make the (alpha)$_2$-subunit of a calcium channel. Such a cell according to the invention can also contain a DNA which comprises a cDNA which can be expressed to make the (alpha)$_1$-subunit of a calcium channel. Preferably, the (alpha)$_2$-subunit or the (alpha)$_1$-subunit made from such a cDNA in such a cell will be foreign to the cell, i.e., will have an amino acid sequence which differs from that of any calcium channel (alpha)$_1$-subunit or (alpha)$_2$-subunit which occurs in a cell of the same type which does not contain a DNA from which the (alpha)$_1$-subunit or the (alpha)$_2$-subunit encoded by such a cDNA is expressed. Preferred among such cells are those of mammalian origin, such as COS cells, NIH3T3 cells, mouse L cells or the like, or those of yeast such as *S. cerevisiae* or *P. pastoris*. Methods of making such cells of the invention, by transforming cells with suitable heterologous DNAS, to be maintained in the cell as episomes or (preferably) integrated into chromosomal DNA of the cell, and then culturing transformants or subculturing (or passaging, in the case of mammalian cells) from such a culture or a subculture thereof, are well known to those of ordinary skill.

Among such cells of the invention, the invention entails also an eukaryotic cell with an heterologous calcium channel, said calcium channel made by a process comprising expression of a first cDNA, which codes for the precursor of the (alpha)$_1$-subunit of a calcium channel of an animal of a first species, and a second cDNA, which codes for the precursor of the (alpha)$_2$-subunit of a calcium channel of a second species, said first and second species being the same or different. Usually at least one of said precursor of said (alpha)$_1$-subunit and said precursor of said (alpha)$_2$-subunit is foreign to said cell. Again, preferred among such cells are those of mammalian origin or those of yeast such as *S. cerevisiae cells* or *P. pastoris*. In a preferred embodiment, such a cell will also contain another heterologous gene, which comprises a transcriptional control element (e.g., a promoter or promoter/enhancer combination), which is active in said cell and the transcriptional activity of which responds to an ion or molecule capable of entering said cell through a functional calcium channel (e.g., $Ca^{++}$, $Ba^{++}$, $Ca^{++}$ ionophores), linked operatively for expression to a structural gene for an indicator protein, such a chloramphenicol acetyltransferase, luciferase or β-galactosidase.

These cells of the invention, which have functional, foreign calcium channels (i.e., functional calcium channels wherein at least one of the (alpha)$_1$-subunit and the (alpha)$_2$-subunit is foreign to the cell) will be useful for, among other purposes, assaying a compound for calcium channel agonist or antagonist activity. First, such a cell can be employed to measure the affinity of such a compound for the functional calcium channel. Secondly, such a cell can be employed to measure electrophysiologically the calcium channel activity in the presence of the compound being tested as well as a ion or molecule, such as $Ca^{++}$ or $Ba^{++}$, which is known to be capable of entering the cell through the functional channel. For similar studies which have been carried out with the acetylcholine receptor, see Claudio et al. Science 238 1688–1694 (1987). These methods for assaying a compound for calcium channel agonist or antagonist activity are also part of the present invention.

Such cells according to the invention, in the preferred embodiment, wherein the cell also contains an heterologous gene with a transcriptional control element, which is active in the cell and responsive to an ion or molecule capable of entering the cell through a functional calcium channel and is linked operatively for expression to a structural gene for an indicator protein, can also be employed, in another method according to the invention for assaying a compound for calcium channel agonist or antagonist activity. This method comprises exposing a culture of such cells to a solution of a compound being tested for such activity, together with an ion or molecule, which is capable of entering the cells through a functional calcium channel and affecting the activity of the transcriptional control element controlling transcription of the gene for the indicator protein, and comparing the level of expression, in the cells of the culture, of the gene for the indicator protein with the level of such expression in the cells of another, control culture of such cells.

A "control culture," as clearly understood by the skilled, will be a culture that is, and is treated, substantially the same as the culture exposed to the compound being assayed except that the control culture is not exposed to the compound being assayed. Levels of expression of the genes for the indicator proteins are ascertained readily by the skilled by known methods, which involve measurements of the concentration of indicator protein via assays for detectable compounds produced in reactions catalyzed by the indicator protein.

As indicated above, indicator proteins are enzymes which are active in the cells of the invention and catalyze production of readily detectable compounds (e.g., chromogens, fluorescent compounds).

In a still further aspect, the invention is a method for diagnosing Lambert-Eaton Syndrome in a person by immunoassay which method comprises combining serum from the person with (alpha)$_1$-subunit of a first animal species and (alpha)$_2$-subunit of a second animal species (the same as or different from the first species) and ascertaining whether antibodies in the serum react with one or both of the subunits to a greater extent than antibodies in control serum (e.g., from a person or group of persons known to be free of the Syndrome). Any immunoassay procedure known in the art for detecting antibodies in serum against a given antigen can be employed in the method. Preferably, in the method, both of the (alpha) subunits are from a mammalian calcium channel, most preferably human.

The invention entails also a labeled (e.g., $^{32}P$ or a biotinylated) RNA or single-stranded DNA of at least 12 (preferably at least 30) bases in length in a sequence which comprises a sequence of at least 12 (preferably at least 30) contiguous bases between bases-238 and 3495, inclusive, in FIG. 2 below, or such a labeled RNA or single-stranded DNA with a sequence taken from the cDNA, described in Example 4, which encodes an human neuronal (alpha)$_2$-subunit. The use of such DNAs and RNAs as probes, to identify and isolate cDNAs coding calcium channel (alpha)$_2$-subunits or to identify tissue in which (alpha)$_2$-subunit mRNA is made, is clear to the skilled. In this regard, see, e.g., Example 4.

The primary strategy for cloning cDNAs encoding the (alpha)$_1$ and the (alpha)$_2$ polypeptide subunits of the DHP-sensitive calcium channels from rabbit skeletal muscle was to screen rabbit back skeletal muscle lambda gt11 cDNA expression libraries with antibody probes specific to each of the proteins. See generally Ausubel et al. Current Protocols in Molecular Biology, Wiley-interscience, New York (1987); Davis et al. Basic Methods in Molecular Biology, Elsevier Science Publishing Co., New York (1986). Monoclonal antibodies capable of immunoprecipitating the $M_r$ 155K–170K DHP receptor (alpha)$_1$ protein from rabbit skeletal muscle triads have been described previously by Leung, et al. J. Biol. Chem. 262, 7943–7946 (1987). Polyclonal antisera specific for the (alpha)$_2$ polypeptide subunit was prepared in guinea pigs using SDS polyacrylamide gel purified (alpha)$_2$ protein as described by Nakayama, et al. J. Biol. Chem. 262, 6572–6576 (1987). One of the (alpha)$_1$-specific monoclonal antibodies, designated as IIF7 by Leung, et al. supra, and the (alpha)$_2$-specific polyclonal antisera were used for screening of $1.0 \times 10^6$ recombinant phages of an oligo-dT primed lambda gt11 cDNA library. Probes based on the Tanabe et al. (alpha)$_1$-subunit cDNA sequence (Nature 328,313–318 (1987)) could also be used to identify clones with fragments of the (alpha)$_1$-subunit cDNA.

Once a positive clone was found using an antibody-screening method, the clone was used to screen further for overlapping clones. A sequential series of overlapping clones was thus generated. These clones were sequenced and fragments were subcloned into either pIBI 24/25 (IBI, New Haven, Conn.) or M13 mp18/19. In cloning the (alpha)$_1$-subunit, the DNA sequence was compared to the primary sequence of the DHP receptor (alpha)$_1$-subunit reported by Tanabe et al. Nucleotide differences resulting in amino acid differences were confirmed by sequencing in both directions.

As pertains to the (alpha)$_1$-subunit, initially, two cDNA clones which reacted positively with the IIF7 monoclonal antibody were isolated and found to be related by cross-hybridization.

DNA sequencing of one of these clones revealed the presence of a cDNA insert of 453 base pairs (bp). Significantly, this insert coded for a 151 amino acid open reading frame with 28% homology to a region for the Electrophorus electroplax sodium channel sequence. The cDNA insert derived from this clone was used to rescreen the lambda gt11 cDNA library and a rabbit back skeletal muscle Okayama-Berg cDNA library (MacLennan, et al., Nature 316, 696–700 (1985)) to isolate overlapping cDNA clones. The cDNA clones were analyzed using the dideoxy chain-termination method of Sanger to determine the entire coding sequence of the (alpha)$_1$ subunit of the calcium channel and a restriction map was made for comparison and orientation of DNA sequences.

An oligo-dT-primed expression cDNA library was constructed in lambda gt11, using young adult rabbit back skeletal muscle poly (A+) RNA (kindly provided by J. Robbins, University of Cincinnati) isolated in guanidine isothiocyanate (see Gubler, et al., Gene 25, 263–269 (1983); Lapeyre, et al., Gene 37, 215–220 (1985); Huynh et. al, DNA Cloning: A Practical Approach, Vol. I 49–78 (IRL, Oxford, 1985)). Double-strand cDNA was synthesized and EcoRI adapaters were added. After the addition of the adapters, the double-strand cDNA was size-selected on a Sepharose CL-4B or Bio-Gel A-50 m column. Fragments >1500 bp were ligated into EcoRI digested, dephosphorylated lambda gt11. The library was packaged in vitro with Gigapack-plus, (Stratagene, San Diego, Calif.) and an efficiency of >95% recombinants was determined by plating in the presence of X-gal and IPTG. Two clones of a total $1 \times 10^6$ recombinants were identified by screening the expression library with monoclonal Ab IIF7 reactive with the $M_r$ 170,000 (alpha)$_1$ subunit of the rabbit skeletal muscle calcium channel. Positive plaques were visualized by binding HRP-goat anti-mouse IgG followed by color development with 4-chloro-1-naphthol. Each clone contained a ~500 bp insert and was related by cross-hybridization. one clone was DNA sequenced to identify an open reading frame (nts 2847–3300) and was used to identify a 6.5 Kb transcript by Northern analysis The 453 bp insert noted above was used to rescreen the lambda gt11 library and 8 of $1 \times 10^6$ clones were positive. One clone (1700 bp) extended the farthest 5' to nt 2237; its 522 bp PstI fragment, nts 2294–2816, was used to screen $1 \times 10^6$ transformants of a rabbit back skeletal muscle cDNA library constructed according to the method of Okayama and Berg (see MacLennan, et. al., Nature 316, 696–700 (1985)). Three positive clones were isolated, of which the largest (5.0 Kb) extended 5' to nt ~750. The Okayama-Berg cDNA library was rescreened with a 5' 250 bp (PstI)-EcoRI fragment (the PstI site is donated by the Okayama-Berg vector) (nts ~750–1006). The longest clone isolated, of 5 positives, was 5.3 Kb, extending 5' to nt ~450. To clone the 5' end of (alpha)$_1$, a random primed rabbit back skeletal muscle lambda gt11 cDNA library was synthesized as described above with the following modifications: (1) pd(N)$_6$ hexamers (Pharmacia, Inc. Piscathaway, N.J.) were used to random prime the first strand cDNA reaction, (2) Adapters containing NcoI, KpnI, and EcoRI sites:

```
5'-CCATGGTACCTTCGTTGACG-3'

3'-GGTACCATGGAAGCAACTGCTTAA-5'
``` were ligated to the double-strand cDNA as described above, and (3) the double-strand cDNA was size-selected on a 1 ml Bio-Gel A50 m column. Fragments >600 bp were ligated into lambda gt11. $1 \times 10^6$ recombinants of this library were screened in duplicate with the 1,648 bp EcoRI/XhoI fragment corresponding to nt 1006–2653 and an oligonucleotide probe spanning the initiating methionine: 5'-GGGAAGCCATGGAGCCATCCTCACCCCAGG-3'. Forty clones were positive with both probes, of which one (1.55 Kb) extended 78 nts 5' of the start codon and ~450 bp 3' of the EcoRI site.

FIG. 1 (below) shows the 5,975 nucleotide sequence of the cDNA encoding the (alpha)$_1$-subunit. There is a 5,619 nucleotide sequence reading frame which encodes a sequence of 1,873 amino acids (FIG. 1). The sequence context of the designated initiation codon is consistent with the proposed consensus sequence of Kozak, Nucleic Acids Res. 15, 8125–8132 (1987). The 3' non-coding sequence of the cDNA is 234 nucleotides in length, excluding the poly (dA) tract, and contains a consensus polyadenylation signal ATTAAA (nucleotides 5832–5837) 17 nucleotides upstream from the poly (dA) tract. This cDNA sequence is consistent with an ~6,500 nucleotide DHP receptor (alpha)$_1$ mRNA. Furthermore, the DNA sequence is 99.4% identical to the cDNA sequence encoding the DHP receptor reported by Tanabe, et. al., supra. Nucleotide differences were identified at 33 positions, of which three, nucleotides 5423, 5444 and 5504 also result in amino acid changes.

As pertains to the (alpha)$_2$-subunit, in an initial screen with the guinea pig (alpha)$_2$-specific polyclonal antisera, three cDNA clones were isolated and shown to be related to each other but not any (alpha)$_1$ cDNA sequences by cross-hybridization. Two of these cDNA clones were used to rescreen the lambda gt11 cDNA library to isolate overlapping cDNA clones. The cDNA clones were analyzed to establish the coding DNA sequence of the (alpha)$_2$ subunit of the calcium channel and a restriction map was made. Approximately 7,850 nucleotides of (alpha)$_2$ cDNA was cloned, which is consistent with an ~8,000 nucleotide (alpha)$_2$ mRNA.

An oligo-dT-primed expression cDNA library was constructed in lambda gt11, using young adult rabbit back skeletal muscle poly (A+) RNA as described for the (alpha) 1-subunit. Double-stranded cDNA fragments >1500 bp were ligated into lambda gt11 and a primary plating of $1 \times 10^6$ recombinants was screened with guinea pig anti-160 Kd (alpha)$_2$ polyclonal anti-sera. Three positive plaques were visualized by binding HRP-Protein A, followed by color development with 4-chloro-1-naphthol. Two clones, (2.5 Kb and 3.6 Kb) overlapped to encode 4.75 Kb of an ~8 Kb transcript identified by Northern analysis. (alpha)$_2$ cDNA clones extending in the 5' and 3' direction (oriented by DNA sequencing and identification of a long open reading frame) were isolated by rescreening the same lambda gt11 cDNA library with the (EcoRI)-HindIII fragment of one clone (nts 43–272, 5' proximal; EcoRI site from adapter) or the EcoRI—(EcoRI) fragment of a second clone (~1.0 Kb in the 3' untranslated region). A total of 14 clones were isolated, seven from each end, of which an overlapping pair of clones (one extending ~2,750 nts 3' and the other extending 350 nts 5') encoded ~7850 nts of the (alpha)$_2$ transcript; 308 nts of 5' untranslated sequence, 3318 nts of coding sequence, and ~4224 nts of 3' untranslated sequence. Only 176 nts of 3' untranslated sequence was confirmed in both directions and is reported.

FIG. 2 represents the 3,802 nucleotides of the cDNA sequence encoding the (alpha)$_2$-subunit and its precursor, including 308 nucleotides of 5' untranslated sequence, a 3,318 nucleotide open reading frame, and 176 nucleotides of 3' untranslated sequence.

FIG. 2 also shows the signal peptide of the (alpha)$_2$-subunit, shown as the first 26 negatively numbered amino acids. An arrow identifies the cleavage site between the signal peptide and the mature (alpha)$_2$-subunit. The N-terminal amino acid sequence previously determined is shown in bold sequence (Thr(+8), Trp(+12), and Asp(+14) were not previously determined.) The nucleotide sequence shown was determined from two clones which overlapped to span the coding sequence of the (alpha)$_2$-subunit. Five nucleotide differences among individual clones were observed resulting in four amino acid changes. Differences occurred in the sequence at positions 169, 347, 348, 984, and a deletion of nts 1858–1860. The amino acids were finally determined to be as follows: Asn at residue 31, Lys at residue 90, and a deletion of Ser at residue 594. An in-frame upstream stop codon is underlined as well as the start and stop codons of an upstream short open reading frame. Three putative transmembrane regions are enclosed in boxes. Potential N-glycosylation and phosphorylation sites are indicated as described for FIG. 1.

The open reading frame encodes a sequence of 1,106 amino acids (FIG. 2). The previously determined NH$_2$-terminal amino acid sequence of the (alpha)$_2$ protein is encoded by nucleotides 79–129 in the same open reading frame (amino acid residues 1–17, FIG. 2). The nucleotide sequence adjacent to the designated initiating codon agrees with the proposed consensus sequence. An in-frame termination codon is present upstream beginning at nucleotide –27. In addition, an out-of-frame potential initiation codon is located beginning at nucleotide –229 and is followed by a nonsense codon at nucleotides –179 to –181. The 5' untranslated sequence of the (alpha)$_2$ cDNA, 308 nucleotides cloned and sequenced thus far, is unusually long. This region is extremely G+C rich, approximately 80% G+C, which is similar to other relatively long 5' non-coding sequences which have been reported.

FIG. 1 shows the 1,873 amino acid sequence deduced from the cDNA of the (alpha)$_1$ subunit of the rabbit skeletal muscle calcium channel. Based on the identification of a clone using the (alpha)$_1$-specific IIF7 monoclonal antibody, we have determined that the protein sequence encoded by the 453 bp cDNA insert (amino acid residues 950–1,100) contains the epitope recognized by this monoclonal antibody. The complete sequence yields a calculated $M_r$ of 212,143 for the (alpha)$_1$ protein, in contrast to the observed Mr 155K–170K, previously reported by others using SDS polyacrylamide gel electrophoresis. The amino acid sequence determined and reported here is 99.8% identical to that recently described by Tanabe et al., supra, showing three amino acid differences at residues 1,808 (Thr to Met), 1,815 (Ala to Val), and 1,835 (Ala to Glu). The calcium channel (alpha)$_1$-subunit protein contains five potential N-glycosylation sites at Asn residues 79, 257, 797, 1,464, and 1,674 and seven potential cAMP-dependent phosphorylation sites at Ser residues 687, 1,502, 1,575, 1,757, 1,772, and 1,854, and Thr 1,552. Analogous to the (alpha)-subunit of the sodium channel, the (alpha)$_1$-subunit of the skeletal muscle calcium channel contains four internal repeated sequence regions. An analysis of the hydropathy profile of the (alpha)$_1$-protein sequence reveals that each repeat contains five hydrophobic segments and one segment with strong positive charge. Since the (alpha)$_1$-protein sequence lacks an hydrophobic amino-terminal sequence characteristic of a signal peptide, it has been proposed that the segments of the four internally repeated regions represent twenty-four transmembrane segments and that the amino- and carboxy-termini extend intracellularly. That model is consistent with two of the potential glycosylation sites (Asn residues 79 and 257) being localized extracellularly and all of the potential phosphorylation cites being localized intracellularly. This generally agrees with previous biochemical studies suggesting that the (alpha)$_1$-subunit (which has been identified as the putative 1,4-dihydropyridine receptor) is not glycosylated but is phosphorylated.

FIG. 2 shows the 1,106 amino acid sequence deduced from the cDNA of the (alpha)$_2$-subunit of the rabbit skeletal muscle calcium channel. The sequence yields a calculated $M_r$ of 125,018 for this protein, in contrast to the observed $M_r$ 165K–175K (under non-reducing conditions; $M_r$ 135K–150K under reducing conditions) determined previously by SDS polyacrylamide gel electrophoresis. The (alpha)$_2$ amino acid sequence deduced here from the cDNA confirms the sequence of 17 amino acids reported earlier as supposedly that of the amino terminal 17 amino acids of the (alpha)$_2$-subunit. The (alpha)$_2$-subunit precursor has a 26 amino acid (residues –1 to –26) signal peptide. While this proposed signal peptide is hydrophobic and of an appropriate length characteristic of signal sequences, it is somewhat unusual in that the peptide has Glu at position-1 and the Gln at position-12 defines a rather short central hydrophic region. The (alpha)$_2$ protein contains 18 potential N-glycosylation sites (Asn residues 68, 112, 160, 300, 324, 444, 451, 580, 589, 652, 671, 758, 801, 865, 872, 962, 975, and 1,005) and two potential cAMP-dependent phosphorylation sites at Thr 477 and Ser 822 (FIG. 2).

An analysis of the (alpha)$_2$ protein sequence for regional hydropathy reveals that, in distinct contrast to similar analysis of the (alpha)$_1$ protein, this protein is substantially hydrophilic, although it does contain a number of hydrophobic regions. Further characterization of the hydrophobic regions of polarity index and hydrophobic moment analyses indicates that three segments may represent transmembrane domains of the (alpha)$_2$ protein. The topography of the (alpha)$_2$ protein is not, however, easily predicted from the deduced primary amino acid sequence. This problem is further compounded by the determination that the (alpha)$_2$ protein lacks significant homology with any protein in the Dayhoff protein sequence database or with other known ion channel and receptor proteins. If the proposed (alpha)$_2$ signal sequence is, in fact, cleaved between the Glu-residue at position –1 and the Glu residue at position, then the amino terminus of the mature protein would be extracellular. Furthermore, assuming that the three hydrophobic segments function as transmembrane domains, and that there are only three such domains, the carboxyl-terminus of the $(alpha)_2$ protein would be intracellular. Such a transmembrane topography would be consistent with 8 out of the 18 potential N-glycosylation sites being localized extracellularly and the single potential phosphorylation site being localized intracellularly. Previous biochemical studies indicate that the $(alpha)_2$-subunit of the skeletal muscle calcium channel is not phosphorylated but is extensively glycosylated.

Rabbit and human genomic DNAs were digested with various restriction enzymes and Southern blots of these DNAs were hybridized with radiolabeled cDNA clones specific for the $(alpha)_1$-subunit or the $(alpha)_2$-subunit. Under conditions of high stringency, very few hybridizing bands were observed in rabbit genomic DNA with either the $(alpha)_1$- or $(alpha)_2$-specific probes. This result is consistent with a low-copy number, perhaps only a single-copy, of each of the $(alpha)_1$- and $(alpha)_2$-subunit genes in the rabbit genome. Southern blot of the same DNA preparations were also probed under conditions of low stringency with the same $(alpha)_1$- and $(alpha)_2$-specific probes. While additional hybridizing bands were observed in rabbit genomic DNA under low stringency conditions with both the (alpha)$_1$- and $(alpha)_2$-specific probes, substantially greater hybridization was observed with the $(alpha)_1$-specific cDNA probes. These results suggest that the $(alpha)_1$- and (alpha)$_2$-subunits of the skeletal muscle DHP-sensitive calcium channel may share significant homology with genes encoding other voltage-dependent DHP-sensitive calcium channels, voltage-dependent calcium channels which are not DHP-sensitive (e.g., T- and N-types), and possibly ligand-gated calcium channels (e.g., glutamate receptor). Interestingly, hybridization bands were observed in human genomic DNA with the $(alpha)_1$-specific cDNA probes under both high and low stringency conditions, whereas significant hybridization of $(alpha)_2$-specific cDNA probes were observed only under low stringency conditions. Thus, while there are human genes homologous to the rabbit $(alpha)_1$- and $(alpha)_2$-subunit genes, greater evolutionary sequence divergence may have occurred in the $(alpha)_2$ gene relative to the $(alpha)_1$ gene.

A further aspect of the invention provides for a diagnostic assay for Lambert Eaton Syndrome (LES). LES is an autoimmune disease characterized by an insufficient release of acetylcholine from motor nerve terminals which normally are responsive to nerve impulses. A recent publication (Kim and Neher, Science 239, 405–408 (1988)) demonstrates that IgG from LES patients block individual voltage-dependent calcium channels and thus prevent function. A diagnostic assay for LES based on immunological reactivity of LES IgG with calcium channel $(alpha)_2$-subunit alone or in combination with $(alpha)_1$-subunit is thus provided for. For example, such an assay may be based on immunoprecipitation of LES IgG by the calcium channels subunits of the invention.

EXAMPLE 1

Isolation of RNA for cDNA Library

On the day before RNA is isolated, prepare the following. As a precaution, all glassware should be baked and all stock solutions in the list immediately below should be sterilized by autoclaving.

200 ml of 0.1 NaOAc, pH 5.2, 1 mM EDTA 50 ml of 0.2 M $Na_2$ EDTA, pH 8.0.

50 ml of 1 M Tris, pH 7.5

50 ml of 3.2 Tris, pH 7.2

50 ml of 0.01 M Tris (pH 8.0), 1 mM EDTA 50 ml PK buffer (0.1 M Tris, pH 7.2, 50 mM NaCl, 10 mM EDTA)

50 ml of 10% SDS, 4 l of ultrapure $H_2O$

On the morning of the RNA isolation, combine:

100 ml $H_2O$ 100 g guanidine isothiocyanate (IBI)

10.6 ml 1 M Tris, pH 7.5

10.6 ml 0.2 M EDTA

Stir, but do not heat above 65° C. to dissolve guanidine isothiocyanate.

Dissect young adult rabbit back skeletal muscle on a clean glass plate and add about 10 g of muscle tissue (cut in ~4 mm pieces) to 50 ml of the guanidine isothiocyanate solution in e.g., a 100 ml Wheaton bottle.

Homogenize using "tissuemizer" from Tekman (large blade) for 10–20 sec., or until small pieces are no longer visible.

Place in 60° $H_2O$ bath, add 30 ml of redistilled phenol which has been made 0.1% in 8-OH quinoline, 0.2% β-ME. Solution should be clear and homogenous after this addition.

Add 30 ml of a 1:1 solution of chloroform:acetate buffer.

Shake vigorously at 60° for 10 minutes; the solutions should appear opaque; if not, add sufficient chloroform:acetate until it turns milky.

Cool on ice, spin to separate phases (7000×g, 10–20 minutes)

Take off and pass it vigorously through a 22 gauge needle.

Treat with phenol:chloroform (1:1) saturated with acetate buffer. Extract aqueous layer with 3×volume of chloroform. Add 2 vol of –20° EtOH, and ppt for 1–2 hours, but no longer.

Collect precipitate; dry briefly (<5 minutes) under vacuum. Resuspend in 7 ml of PK buffer made 0.2% with respect to SDS. If precipitate develops, heat at 65° until solution clears. Add 1.5 mg of proteinase K.

Incubate 20 minutes at 37° (if you have dried for too long, RNA will be very difficult to get into solution and vigorous pipetting will be necessary throughout the incubation).

Extract reaction with 1:1 phenol:chloroform (made 0.1% in 8-OH quinoline, 0.2% β-ME, saturate with 100 mM Tris, pH 8.5 or PK buffer pH 7.7), 2× with chloroform, ppt by addition of 1/10 volume of 3.2 M Tris, pH 7.5 and 2 vol. of EtOH. Poly $A^+$ RNA may then be isolated from the RNA mixture by well-known hybridization methods utilizing matrix-immobilized oligo (dT).

EXAMPLE 2 cDNA Cloning Procedure

1. First Strand Synthesis a. The following reagents and compositions are combined together and incubated on ice for 5 minutes:

| Reagent | Volume | Final Concentration |
| --- | --- | --- |
| ~5 µg poly A + RNA, plus water | to 10.5 µl | |
| 5X reverse transcriptase buffer | 10 µl | 1X |
| 0.5M DTT | 1 µl | 10 mM |
| RNasin (24 U/µl) | 2 µl | ~1U/µl |
| 5X dNTPs | 10 µl | 1X |
| oligo dT (250 µg/ml) | 5 µl | 25 µg/µl | b. Next, the following three reagents are added to (a) and the mixture is incubated at 37° C. for 60 minutes:

| | | |
|---|---|---|
| actinomycin D (600 µg/ml) | 4 µl | ~50 µg/ml |
| $^{32}$P-gammadCTP (3200 Ci/mmol) | 2.5 µl | — |
| MMLV-reverse transcriptase (BRL-200 U/µl) | 5 µl | 200 U/µg RNA |
| | 50 µl | (total a + b) | c. The following reagents are added to (b) and the mixture is incubated at 37° C. for 30 minutes:

| | |
|---|---|
| RNasin (24 U/µl) | 1 µl |
| MMLV-reverse transcriptase (BRL-200 U/µl) | 3 µl | d. Take aliquots for analysis:
1 µl at time 0 for TCA
1 µl at 90 minutes for TCA
0.5 µl at 90 minutes for gel e. The reaction is stopped after 30 minutes by adding 2 µl of 0.5M EDTA and performing one phenol/chloroform extraction, followed by one chloroform extraction. Then 10 µl of 10 M NH$_4$OAc plus two volumes of ethanol are added to precipitate the first strand.

f. To analyze the synthesis, 0.5 µl of the reaction are run on a 1.5% agarose mini-gel, the gel is photographed, dried, and placed under film (generally an overnight exposure with an intensifying screen is adequate).

g. Calculate the mass of cDNA from the percent incorporation of label above background. 1 µg ss cDNA=1.4% incorporation.

2. Second Strand Synthesis a. The cDNA-RNA is spun down by centrifugation in a benchtop microfuge for 15 minutes. The pellet is washed in 95% ethanol and dried.

b. The following mixture is assembled and incubated at 12° C. for 60 minutes.

| | Volume | Final Concentration |
|---|---|---|
| cDNA RNA, plus water | to 68 µl | |
| 5X 2nd strand buffer | 20 µl | 1X |
| 10 mM β-NAD | 1.5 µl | 0.15 mM |
| 4 mM dNTPs | 5 µl | 200 µM/ml |
| DNA polymerase I (10 U/µl) | 2.5 µl | 250 U/ml |
| E.coli DNA ligase (2 U/µl) | 2 µl | 40 U/ml |
| RNase H (2.3 U/µl) | 1 µl | 23 U/ml |
| | 100 µl | | c. To this mix is added the following, and incubation continues at 22° C. for 60 minutes:

| | |
|---|---|
| DNA polymerase I (10 U/µl) | 1.5 µl |
| E. coli DNA ligase (2 U/µl) | 1.5 µl | d. The reaction is stopped after 60 minutes by adding 4 µl of 0.5M EDTA and performing one phenol/chloroform extraction and one chloroform extraction.

e. The aqueous phase is run over a G-50 column in a short Pasteur pipet and 100 µl fractions are collected. The 500 µls containing the cDNA is collected and pooled, and butanol extracted down to a volume of ~50 µl. The cDNA is precipitated by adding 10 µl of 10 M NH$_4$OAc plus two volumes of ethanol.

3. T4 Polymerase Reaction a. The cDNA is spun down in a microfuge for 15 minutes. A 95% ethanol wash is performed and the cDNA pellet is dried. The dry pellet is counted in a scintillation counter. Assume 100% efficiency of the 2nd strand reaction, and calculate mass of double-stranded cDNA from the first strand calculation.

b. To the cDNA is added the following, and the mixture is incubated at 37° C. for 20 minutes.

| | |
|---|---|
| cDNA | + |
| 10X T4 buffer | 5 µl |
| H$_2$O | 40.75 µl |
| 4 mM dNTPs | 1.25 µl |
| 0.1 mM DTT | 2.5 µl |
| T4 polymerase (10 U/µl) | 0.5 µl |
| | 50 µl | c. Aliquots are taken:
0.5 µl for gel at time 0
0.5 µl for gel at 20 minutes d. The reaction is stopped after 20 minutes by adding 2 µl of 0.5 M EDTA, followed by a phenol/chloroform extraction and a chloroform extraction.

e. The aqueous phase is run over a G-50 column in a short Pasteur pipet and 100 µl fractions are collected. The 500 µls containing the cDNA is collected and pooled, and butanol extracted down to a volume of ~50 µl. The cDNA is precipitated by adding 10 µl of 10 M NH$_4$OAc plus two volumes of ethanol.

f. The 0.5 µl samples taken at time 0 and 20 minutes are run on a 1.5% agarose mini-gel, which is subsequently photographed, dried, and placed under film.

4. Addition of EcoRI Adapters (for insertion into lambda gt11)

a. Oligos are synthesized having the following sequences:

```
20 mer:   5'-CCATGGTACCTTCGTTGACG-3'

24 mer:   3'-GGTACCATGGAAGCAACTGCTTAA-5'
``` b. The 20 mer is phosphorylated by combining the following reagents and incubated at 37° C. for 15 minutes.:

| | |
|---|---|
| 225 pmoles 20 mer | + |
| water | 6.8 µl |
| 10X kinase buffer | 1.2 µl |
| $^{32}$P-gammaATP (7000 Ci/mmole) | 1.0 µl |
| kinase (2 U/µl) | 1.0 µl |
| | 10 µl | c. The following two reagents are added to above mixture and it is incubated at 37° C. for 30 minutes:

| | |
|---|---|
| 10 mM ATP | 1 µl |
| kinase (2 U/ml) | 1 µl |
| | 12 µl (total b + c) | d. The enzyme is then inactivated by boiling for 10 minutes.

e. The 24 mer is hybridized to the phosphorylated 20 mer by addition of 225 pmoles of the 24 mer (plus water to bring volume to 15 µl), and incubation at 65° C. for 5 minutes. The reaction is then allowed to slow cool to room temperature.

The adapters are now present at a concentration of 15 pmoles/µl, and are ready for cDNA-vector ligation.

f. Combine the following:

| | |
|---|---|
| cDNA | + |
| hybridized adapters (15 pmol/µl) | 50-fold molar excess over cDNA |
| water | 16 µl |
| 10X ligase buffer | 2 µl |
| ligase (10 U/µl) | 2 µl |
| | 20 µl |

5. Phosphorylation of cDNA a. The ligase is inactivated by heating the mixture to 72° C. for 15 minutes.

b. The following reagents are added to the cDNA ligation reaction and it is heated at 37° C. for 30 minutes:

| | |
|---|---|
| cDNA ligation reaction | 20 µl |
| water | 24 µl |
| 10X kinase buffer | 3 µl |
| 10 mM ATP | 1 µl |
| kinase (2 U/µl) | 2 µl |
| | 50 µl | c. The reaction is stopped by the addition of 2 µl 0.5M EDTA, followed by one phenol/chloroform extraction and one chloroform extraction.

6. Purification and Size-Selection of cDNA a. The cDNA is run over a BIO-GEL A-50 column that has been washed with ≧5 ml of TE buffer. The column has 0.8 ml bed resin in a 0.2 cm (inner diameter)×30 cm siliconized glass tube with a glass wool plug in a yellow pipet tip at the bottom.

b. The cDNA is dried down in a speed vac to ~20 µl. 2.5 µl of gel loading dye is added and the cDNA is run over the column. The counts begin coming off after running 200–250 µl TE buffer through the column. 5 minute fractions (~30 µl) are collected and counted in a scintillation counter. Free adapters may begin to elute off 350–400 µl after the cDNA starts to elute.

c. 0.5 µl of several of the collected fractions are run on a 1.5% agarose minigel. The gel is photographed, dried down, and placed under film.

7. Ligation of cDNA to lambda gt11 vector a. The fractions containing cDNA are pooled, butanol extracted down to 20–30 µl, and 5 µl of 10M NH₄OAc plus two volumes of ethanol is added to precipitate the cDNA. It is spun in a microfuge for 15 minutes, and then subjected to a 95% ethanol wash and dry.

b. The pellet is counted, and the mass of cDNA is calculated relative to the mass after the second strand synthesis.

c. The cDNA is resuspended in TE (~0.10 pmol/µl).

d. The ligation reaction contains the following, which is incubated at 14–16° C. overnight:
(use 1 µg of lambda gt11 vector =0.035 pmol vector)

| | |
|---|---|
| lambda gt11 (1 µg/µl) | 1 µl |
| cDNA insert | (2–4 fold molar excess of cDNA over vector) |
| water | to 3 µl |
| 5X ligase buffer | 1 µl |
| ligase (10 U/µl) | 1 µl |
| | 5 µl |

8. Packaging

The vector is packaged using the Gigapack in vitro packaging kit supplied by Strategene, and following the instructions contained therein.

| REAGENTS | |
|---|---|
| 5X RT buffer | |
| 250 mM Tris, pH 7.4 | 250 µl of 1M |
| 375 mM KCl | 375 µl of 1M |
| 15 mM MgCl₂ | 75 µl of 0.2M |
| H₂O | 300 µl |
| | 1000 µl |
| 5X dNTPs | |
| 5 mM dATP | 14.1 µl |
| 3 mM dCTP | 9.1 µl |
| 5 mM dGTP | 13.6 µl |
| 5 mM dTTP | 13.3 µl |
| | 50 µl |
| 5X 2nd Strand Buffer | |
| 100 mM Tris, pH 7.5 | 100 µl of 1M |
| 500 mM KCl | 500 µl of 1M |
| 50 mM (NH₄)₂SO₄ | 50 µl of 1M |
| 25 mM MgCl₂ | 125 µl of 0.2M |
| 250 µg/ml BSA | 5 µl of 50 mg/ml |
| water | 220 µl |
| | 1000 µl |
| 10X T4 buffer | |
| 670 mM Tris, pH 8.0 | 670 µl of 1M |
| 167 mM (NH₄)₂SO₄ | 167 µl of 1M |
| 67 mM MgCl₂ | 67 µl of 1M |
| H₂O | 96 µl |
| | 1000 µl |

EXAMPLE 3

Screening cDNA Library with Antibody

Plate lambda gt11 library on Y1090 in LB agar and 50 µg/ml ampicillin. Grow overnight in 15 ml of LB, 0.2% maltose and 50 µg/ml ampicillin. Pellet the cells and resuspend in 3 ml of 10 mM MgSO₄. Plate four plates at 250,000 plaques/plate using 25 µl of phage (10,000/µl) and 300 µl of said 3 ml solution of cells in 10 ml soft agar containing 50 µg/ml ampicillin.

Grow at 42° C. for 2.5 hours and overlay IPTG-treated filters which were soaked in 10 mM IPTG (Boehringer Mannheim Biochemicals, Indianapolis, Ind.). Dry filters until just moist, lay them in the plates and incubate overnight at 37° C.

Orient the plates and spot 0.5 µl of purified DHP receptor on one plate as a positive control. Wash the filters for 10 min at room temperature TBS (50 mM TRIS, 150 mM NaCl, pH 8.0). Wash filters in TBS, 20% FCS (filtered) for 30 min at room temp.

Incubate the filters for 2 hours in TBS, 20% FCS, anti-DHS-receptor antibody (monoclonal or polyclonal). Wash for 10 min in TBS. Transfer filters to new plates and wash for 1 min in TBS, 0.1% NP40. Wash for 10 min in TBS and transfer to new plates.

Incubate for at least 1 hour with TBS, 20% FCS containing an appropriate second antiboby (e.g. HRP-Protein A; or HRP-goat anti-mouse IgG).

Wash filters as described above for the first antibody.

Develop the positive clones using about 40 ml/plate of 4-chloro-1-naphthol reagent which is made by dissolving 60 mg of said developer in 20 ml of ice cold MeOH and mixing 4-chloro-1-naphthol (Aldrich Chemical Company, Milwaukee, Wis.) into 100 ml of TBS containing 60 µl of 30% $H_2O_2$.

EXAMPLE 4

An Human Neuronal Calcium Channel (Alpha)$_2$-Subunit-Encoding cDNA

Because of the indications, mentioned supra, that human calcium channel (alpha)$_2$-subunit genes had diverged somewhat from rabbit calcium channel (alpha)$_2$-subunit genes, human (alpha)$_2$-subunit-encoding fragments were isolated to use as probes to screen human brain cDNA libraries under high stringency conditions.

Thus, an EcoRI-digested human genomic Southern blot was probed under both low and high stringency conditions with a fragment of rabbit (alpha)$_2$-subunit-encoding cDNA (the fragment from nucleotide 43 to nucleotide 272 indicated in FIG. 2). Under low stringency conditions, two genomic fragments were identified, of 3.0 kbp and 3.5 kbp in size. Under high stringency conditions, only the 3.5 kbp fragment maintained a stable hybrid. These two fragments were cloned into lambda-gt11. The 3.5 kbp fragment includes a small PstI-XbaI fragment, of about 300 bp, which includes an 82 bp exon with 96.4% homology to nucleotides 102 to 183 of the sequence in FIG. 2. This exon is preceded by the dinucleotide AG (splice donor) and followed by the dinucleotide GT (splice acceptor), as understood in the art. The 3.0 kbp fragment includes an XbaI-BglII fragment, of about 585 bp, which includes 104 bp of an exon (which includes the BglII site at its downstream end) which, in the 104 bp, has 93.3% homology to nucleotides 184 to 287 of the sequence in FIG. 2. Both the 300 bp, PstI-XbaI fragment and the 585 bp, XbaI-BglII fragments were used to probe duplicate lifts of a human basal ganglia cDNA library in lambda-gt11 (the library having been obtained from the American Type Culture Collection, Rockville, Md., USA, and containing about $10^6$ independent recombinants with an average insert size of 800–1000 bp). Three positive clones were identified which hybridized to both probes under high stringency conditions, one with an insert size of about 1150 bp, another with an insert size of about 790 bp, and the third with an insert size of about 670 bp. The 1150 bp insert in the one clone extended into the coding region from about nucleotide 200 in the coding region and was found to have a sequence more than 90% homologous to that of the corresponding segment of the cDNA whose sequence is presented in FIG. 2. Using the lambda genome with the 1150 bp insert as probe, an human brain stem cDNA library (also purchased from the American Type Culture Collection, and having about $4\times10^6$ independent recombinants with an average insert size of 800–1000 bp) was probed under high stringency conditions. In this probing, four positive clones were identified, with inserts of about 950 bp, 1120 bp, 3000 bp and 2500 bp. Most of the 1120 bp insert overlapped the 1150 bp insert of the DNA used as probe but extended somewhat upstream from the upstream end of the 1150 bp insert. The 2500 bp insert extended downstream from about 650 bp from the 5'-end of the 1120 bp insert. The DNA with the 2500 bp insert was used to again probe the brain stem library, and a clone with a 2750 bp insert was found. The 2750 bp insert was found by restriction analysis and sequencing to extend in the 3'-direction beyond the translational stop signal of a reading frame that was found to begin in the 1120 bp insert described above. The 2750 bp insert and 1120 bp insert have a PvuII site in common and have been ligated using the PvuII site to provide a cDNA that encodes a human neuronal calcium channel (alpha)$_2$-subunit The 5'–1560 bp of this cDNA have been sequenced and, as illustrated in FIG. 3, found to be 91.2% homologous with the corresponding 1575 bp segment indicated in FIG. 2.

The human (alpha)$_2$-subunit-encoding cDNA will be subcloned into the mammalian expression vector pSV2DHFR, which is available in the art, for expression in mammalian tissue culture cells.

We obtained the human neuroblastoma cell line IMR32 from the American Type Culture Collection (accession no. CCL127). A northern blot analysis was carried out on poly A$^+$ RNA from this cell line using the full-length human (alpha)$_2$-subunit-encoding cDNA. Under low stringency washing, a single 8.2 kb fragment was found. The rabbit skeletal muscle (alpha)$_2$-encoding messenger RNA also had a size similar to 8.2 kb. While the invention has been described herein with some specificity, the ordinarily skilled in the art will recognize numerous variations and modifications, in what is described, that are within the spirit of the invention. Such variations and modifications are within the scope of the invention as described in the claims herein.

Various features of the invention are also described in the following claims.

What is claimed is:

1. An isolated DNA molecule, comprising a sequence of nucleotides that encodes the (alpha)$_2$-subunit of a mammalian calcium channel, wherein:

the sequence of nucleotides hybridizes under conditions of high stringency with nucleic acid that includes all or a portion of the sequence of nucleotides set forth in FIG. 2; and the portion includes at least nucleotides 43–272 set forth in FIGS. 2a–2f.

2. The DNA molecule of claim 1, wherein the sequence of nucleotides encodes the $(alpha)_2$-subunit of a skeletal muscle, cardiac, or neuronal calcium channel.

3. The DNA molecule of claim 1, wherein the sequence of nucleotides hybridizes under conditions of high stringency with DNA that is fully complementary to an mRNA transcript that is native to a mammalian cell.

4. Isolated RNA that is encoded by the DNA molecule of claim 1.

5. An isolated eukaryotic cell, comprising the DNA molecule of claim 1, wherein the cell is a mammalian cell.

6. An isolated eukaryotic cell, comprising the RNA complementary to the DNA of claim 1, wherein the cell is an amphibian oöcyte.

7. An isolated DNA molecule that is degenerate with the DNA molecule of claim 1.

8. Isolated mRNA encoded by the DNA of claim 1.

9. A eukaryotic cell, comprising a heterologous calcium channel, wherein said cell is produced by a process comprising administering to said cell a composition that contains mRNA that encodes an $(alpha)_2$-subunit of a calcium channel of a mammal, wherein:

the mRNA is complementary to DNA of claim 1;

the heterologous calcium channel includes the $(alpha)_2$ subunit; and the only heterologous ion channels that are expressed by the oöcyte are calcium channels.

10. The cell of claim 9, which is an amphibian oöcyte, and wherein the composition is administered by microinjection.

11. The cell of claim 10 which is an oocyte of *Xenopus laevis*.

12. The cell of claim 9, wherein said $(alpha)_2$-subunit is a skeletal muscle, cardiac or neuronal calcium channel $(alpha)_2$-subunit.

13. The cell of claim 9, wherein the mammal is selected from the group consisting of rabbit and guinea pig.

14. The cell of claim 13, wherein the $(alpha)_2$-subunit is a skeletal muscle calcium channel $(alpha)_2$-subunit.

15. The cell of claim 9, wherein the mammal is a rabbit.

16. A cultured eukaryotic cell, comprising a heterologous calcium channel, wherein said calcium channel is produced by a process comprising expressing in said cell a DNA molecule of claim 1, whereby the cell expresses a calcium channel that comprises the $(alpha)_2$-subunit encoded by the DNA.

17. The cell of claim 16, wherein said cell is selected from the group consisting of a yeast and mammalian cells.

18. The cell of claim 16, wherein said $(alpha)_2$-subunit is a skeletal muscle, cardiac or neuronal calcium channel $(alpha)_2$-subunit.

19. The cell of claim 18, wherein the mammal is selected from the group consisting of rabbit and guinea pig.

20. The cell of claim 19, wherein the $(alpha)_2$-subunit is a skeletal muscle calcium channel subunit.

21. The cell of claim 20, wherein the mammal is a rabbit.

22. A labeled single-stranded DNA molecule of at least 30 bases in length, comprising at least 30 contiguous bases of the protein-encoding segment of the human neuronal (alpha) $_2$-subunit-encoding nucleic acid set forth in SEQ ID No. 2 or 3 or the complement thereof.

23. An isolated DNA molecule, comprising at least 30 contiguous base pairs of the sequence set forth in SEQ ID No. 2 between nucleotides 71–3802.

24. An isolated DNA molecule, comprising at least 30 contiguous base pairs of the sequence set forth in SEQ ID No. 3.

25. An isolated DNA molecule, comprising the sequence of nucleotides set forth as 43–272 in FIG. 2.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 5975 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence (B) LOCATION: 79...5700
(D) OTHER INFORMATION:

(xi) SEQUENCE DESCRIPTION: SEQ ID NO:1:

```
GCGGGGAACA CTGGGGACGC AGGGAAGAGA GGGCCGCGGG GTGGGGGAGC AGCAGGAAGC    60

GCCGTGGCCA GGGAAGCC ATG GAG CCA TCC TCA CCC CAG GAT GAG GGC CTG    111
                    Met Glu Pro Ser Ser Pro Gln Asp Glu Gly Leu
                     1               5                  10

AGG AAG AAA CAG CCC AAG AAG CCC CTG CCC GAG GTC CTG CCC AGG CCG    159
Arg Lys Lys Gln Pro Lys Lys Pro Leu Pro Glu Val Leu Pro Arg Pro
            15                  20                  25

CCG CGG GCT CTG TTC TGC CTG ACC CTG CAG AAC CCG CTG AGG AAG GCG    207
Pro Arg Ala Leu Phe Cys Leu Thr Leu Gln Asn Pro Leu Arg Lys Ala
        30                  35                  40

TGC ATC AGC ATC GTG GAA TGG AAA CCC TTC GAG ACC ATC ATC CTG CTC    255
Cys Ile Ser Ile Val Glu Trp Lys Pro Phe Glu Thr Ile Ile Leu Leu
    45                  50                  55

ACC ATC TTT GCC AAC TGT GTG GCC CTG GCC GTG TAC CTG CCC ATG CCC    303
Thr Ile Phe Ala Asn Cys Val Ala Leu Ala Val Tyr Leu Pro Met Pro
 60              65                  70                  75

GAG GAT GAC AAC AAC TCC CTG AAC CTG GGC CTG GAG AAG CTG GAG TAC    351
Glu Asp Asp Asn Asn Ser Leu Asn Leu Gly Leu Glu Lys Leu Glu Tyr
                80                  85                  90

TTC TTC CTC ACC GTC TTC TCC ATC GAA GCC GCC ATG AAG ATC ATC GCC    399
Phe Phe Leu Thr Val Phe Ser Ile Glu Ala Ala Met Lys Ile Ile Ala
            95                  100                 105

TAC GGC TTC CTG TTC CAC CAG GAC GCC TAC CTG CGC AGC GGC TGG AAC    447
Tyr Gly Phe Leu Phe His Gln Asp Ala Tyr Leu Arg Ser Gly Trp Asn
        110                 115                 120

GTG CTG GAC TTC ATC ATC GTC TTC CTG GGG GTC TTC ACG GCG ATT CTG    495
Val Leu Asp Phe Ile Ile Val Phe Leu Gly Val Phe Thr Ala Ile Leu
    125                 130                 135

GAA CAG GTC AAC GTC ATC CAG AGC AAC ACG GCC CCG ATG AGC AGC AAA    543
Glu Gln Val Asn Val Ile Gln Ser Asn Thr Ala Pro Met Ser Ser Lys
140                 145                 150                 155

GGA GCC GGC CTG GAC GTC AAG GCC CTG AGG GCC TTC CGT GTG CTC AGA    591
Gly Ala Gly Leu Asp Val Lys Ala Leu Arg Ala Phe Arg Val Leu Arg
                160                 165                 170

CCC CTC CGG CTG GTG TCG GGG GTG CCT AGT TTG CAG GTG GTC CTC AAC    639
Pro Leu Arg Leu Val Ser Gly Val Pro Ser Leu Gln Val Val Leu Asn
            175                 180                 185

TCC ATC TTC AAG GCC ATG CTC CCC CTG TTC CAC ATC GCC CTG CTC GTC    687
Ser Ile Phe Lys Ala Met Leu Pro Leu Phe His Ile Ala Leu Leu Val
        190                 195                 200

CTC TTC ATG GTC ATC ATC TAC GCC ATC ATC GGG CTG GAG CTC TTC AAG    735
Leu Phe Met Val Ile Ile Tyr Ala Ile Ile Gly Leu Glu Leu Phe Lys
    205                 210                 215

GGC AAG ATG CAC AAG ACC TGC TAC TAC ATC GGG ACA GAC ATC GTG GCC    783
Gly Lys Met His Lys Thr Cys Tyr Tyr Ile Gly Thr Asp Ile Val Ala
220                 225                 230                 235

ACA GTG GAG AAT GAG AAG CCC TCG CCC TGC GCT AGG ACG GGC TCG GGG    831
Thr Val Glu Asn Glu Lys Pro Ser Pro Cys Ala Arg Thr Gly Ser Gly
                240                 245                 250

CGC CCC TGC ACC ATC AAC GGC AGC GAG TGC CGG GGC GGC TGG CCG GGG    879
Arg Pro Cys Thr Ile Asn Gly Ser Glu Cys Arg Gly Gly Trp Pro Gly
            255                 260                 265

CCC AAC CAC GGC ATC ACG CAC TTC GAC AAC TTC GGC TTC TCC ATG CTC    927
Pro Asn His Gly Ile Thr His Phe Asp Asn Phe Gly Phe Ser Met Leu
        270                 275                 280

ACC GTG TAC CAG TGC ATC ACC ATG GAG GGC TGG ACA GAT GTC CTC TAC    975
```

-continued

|  |  |  |
|---|---|---|
| Thr Val Tyr Gln Cys Ile Thr Met Glu Gly Trp Thr Asp Val Leu Tyr<br>285                290                          295 | | |
| TGG GTC AAC GAT GCC ATC GGG AAC GAG TGG CCC TGG ATC TAC TTT GTC<br>Trp Val Asn Asp Ala Ile Gly Asn Glu Trp Pro Trp Ile Tyr Phe Val<br>300                305                  310               315 | 1023 | |
| ACT CTC ATC CTG CTG GGG TCC TTC TTC ATC CTC AAC CTG GTG CTG GGC<br>Thr Leu Ile Leu Leu Gly Ser Phe Phe Ile Leu Asn Leu Val Leu Gly<br>                320                    325                   330 | 1071 | |
| GTC CTG AGT GGG GAA TTC ACC AAG GAG CGG GAG AAG GCC AAG TCC AGG<br>Val Leu Ser Gly Glu Phe Thr Lys Glu Arg Glu Lys Ala Lys Ser Arg<br>         335                    340                  345 | 1119 | |
| GGA ACC TTC CAG AAG CTG CGG GAG AAG CAG CAG CTG GAG GAG GAC CTT<br>Gly Thr Phe Gln Lys Leu Arg Glu Lys Gln Gln Leu Glu Glu Asp Leu<br>              350                    355               360 | 1167 | |
| CGG GGC TAC ATG AGC TGG ATC ACG CAG GGC GAG GTC ATG GAC GTG GAG<br>Arg Gly Tyr Met Ser Trp Ile Thr Gln Gly Glu Val Met Asp Val Glu<br>365                      370                    375 | 1215 | |
| GAC CTG AGA GAA GGA AAG CTG TCC TTG GAA GAG GGA GGC TCC GAC ACG<br>Asp Leu Arg Glu Gly Lys Leu Ser Leu Glu Glu Gly Gly Ser Asp Thr<br>380                385                    390               395 | 1263 | |
| GAA AGC CTG TAC GAA ATC GAG GGC TTG AAC AAA ATC ATC CAG TTC ATC<br>Glu Ser Leu Tyr Glu Ile Glu Gly Leu Asn Lys Ile Ile Gln Phe Ile<br>                400                    405                   410 | 1311 | |
| CGA CAC TGG AGG CAG TGG AAC CGT GTC TTT CGC TGG AAG TGC CAT GAC<br>Arg His Trp Arg Gln Trp Asn Arg Val Phe Arg Trp Lys Cys His Asp<br>                    415                    420                   425 | 1359 | |
| CTG GTG AAG TCG AGA GTC TTC TAC TGG CTG GTC ATC CTG ATC GTG GCC<br>Leu Val Lys Ser Arg Val Phe Tyr Trp Leu Val Ile Leu Ile Val Ala<br>                      430                    435               440 | 1407 | |
| CTC AAC ACC CTG TCC ATC GCC TCG GAG CAC CAC AAC CAG CCG CTC TGG<br>Leu Asn Thr Leu Ser Ile Ala Ser Glu His His Asn Gln Pro Leu Trp<br>             445                    450                   455 | 1455 | |
| CTG ACC CAC TTG CAA GAC ATC GCC AAT CGA GTG CTG CTG TCA CTC TTC<br>Leu Thr His Leu Gln Asp Ile Ala Asn Arg Val Leu Leu Ser Leu Phe<br>460                    465                   470               475 | 1503 | |
| ACC ATC GAG ATG CTG CTG AAG ATG TAC GGG CTG GGC CTG CGC CAG TAC<br>Thr Ile Glu Met Leu Leu Lys Met Tyr Gly Leu Gly Leu Arg Gln Tyr<br>                480                    485               490 | 1551 | |
| TTC ATG TCC ATC TTC AAC CGC TTC GAC TGC TTC GTG GTG TGC AGC GGC<br>Phe Met Ser Ile Phe Asn Arg Phe Asp Cys Phe Val Val Cys Ser Gly<br>                    495                    500               505 | 1599 | |
| ATC CTG GAG CTG CTG CTG GTG GAG TCG GGC GCC ATG ACG CCG CTG GGC<br>Ile Leu Glu Leu Leu Leu Val Glu Ser Gly Ala Met Thr Pro Leu Gly<br>             510                    515                   520 | 1647 | |
| ATC TCC GTG TTG CGC TGC ATC CGC CTC CTG AGG CTC TTC AAG ATC ACC<br>Ile Ser Val Leu Arg Cys Ile Arg Leu Leu Arg Leu Phe Lys Ile Thr<br>525                    530                    535 | 1695 | |
| AAG TAC TGG ACG TCG CTC AGC AAC CTG GTG GCC TCC CTG CTC AAC TCC<br>Lys Tyr Trp Thr Ser Leu Ser Asn Leu Val Ala Ser Leu Leu Asn Ser<br>540                    545                    550               555 | 1743 | |
| ATC CGC TCC ATC GCC TCG CTG CTG CTG CTC TTC CTC TTC ATC ATC<br>Ile Arg Ser Ile Ala Ser Leu Leu Leu Leu Phe Leu Phe Ile Ile<br>                    560                    565               570 | 1791 | |
| ATC TTC GCC CTG CTG GGC ATG CAG CTC TTC GGG GGG CGG TAC GAC TTC<br>Ile Phe Ala Leu Leu Gly Met Gln Leu Phe Gly Gly Arg Tyr Asp Phe<br>                    575                    580               585 | 1839 | |
| GAG GAC ACG GAA GTG CGA CGC AGC AAC TTC GAC AAC TTC CCC CAG GCC<br>Glu Asp Thr Glu Val Arg Arg Ser Asn Phe Asp Asn Phe Pro Gln Ala<br>             590                    595                   600 | 1887 | |
| CTC ATC AGC GTC TTC CAG GTG CTG ACG GGT GAG GAC TGG AAC TCC GTG | 1935 | |

-continued

| | | | | | | | | | | | | | | | | |
|---|---|---|---|---|---|---|---|---|---|---|---|---|---|---|---|---|
| Leu | Ile | Ser | Val | Phe | Gln | Val | Leu | Thr | Gly | Glu | Asp | Trp | Asn | Ser | Val | |
| | 605 | | | | 610 | | | | | 615 | | | | | | |

| ATG | TAC | AAC | GGG | ATC | ATG | GCC | TAC | GGA | GGC | CCG | TCC | TAC | CCG | GGC | GTT | 1983 |
|---|---|---|---|---|---|---|---|---|---|---|---|---|---|---|---|---|
| Met | Tyr | Asn | Gly | Ile | Met | Ala | Tyr | Gly | Gly | Pro | Ser | Tyr | Pro | Gly | Val | |
| 620 | | | | | 625 | | | | | 630 | | | | | 635 | |

| CTC | GTG | TGC | ATC | TAT | TTC | ATC | ATC | CTT | TTT | GTC | TGC | GGC | AAC | TAT | ATC | 2031 |
|---|---|---|---|---|---|---|---|---|---|---|---|---|---|---|---|---|
| Leu | Val | Cys | Ile | Tyr | Phe | Ile | Ile | Leu | Phe | Val | Cys | Gly | Asn | Tyr | Ile | |
| | | | | 640 | | | | | 645 | | | | | 650 | | |

| CTG | CTG | AAT | GTC | TTC | CTG | GCC | ATC | GCC | GTG | GAC | AAC | CTG | GCC | GAG | GCC | 2079 |
|---|---|---|---|---|---|---|---|---|---|---|---|---|---|---|---|---|
| Leu | Leu | Asn | Val | Phe | Leu | Ala | Ile | Ala | Val | Asp | Asn | Leu | Ala | Glu | Ala | |
| | | | | 655 | | | | | 660 | | | | | 665 | | |

| GAG | AGC | CTG | ACT | TCC | GCG | CAA | AAG | GCC | AAG | GCC | GAG | GAG | AGG | AAA | CGT | 2127 |
|---|---|---|---|---|---|---|---|---|---|---|---|---|---|---|---|---|
| Glu | Ser | Leu | Thr | Ser | Ala | Gln | Lys | Ala | Lys | Ala | Glu | Glu | Arg | Lys | Arg | |
| | | 670 | | | | | 675 | | | | | 680 | | | | |

| AGG | AAG | ATG | TCC | AGG | GGT | CTC | CCT | GAC | AAG | ACG | GAG | GAG | GAG | AAG | TCT | 2175 |
|---|---|---|---|---|---|---|---|---|---|---|---|---|---|---|---|---|
| Arg | Lys | Met | Ser | Arg | Gly | Leu | Pro | Asp | Lys | Thr | Glu | Glu | Glu | Lys | Ser | |
| | 685 | | | | | 690 | | | | | 695 | | | | | |

| GTG | ATG | GCC | AAG | AAG | CTG | GAG | CAG | AAG | CCC | AAG | GGG | GAG | GGC | ATC | CCC | 2223 |
|---|---|---|---|---|---|---|---|---|---|---|---|---|---|---|---|---|
| Val | Met | Ala | Lys | Lys | Leu | Glu | Gln | Lys | Pro | Lys | Gly | Glu | Gly | Ile | Pro | |
| 700 | | | | | 705 | | | | | 710 | | | | | 715 | |

| ACC | ACT | GCC | AAG | CTC | AAG | GTC | GAT | GAG | TTC | GAA | TCT | AAC | GTC | AAC | GAG | 2271 |
|---|---|---|---|---|---|---|---|---|---|---|---|---|---|---|---|---|
| Thr | Thr | Ala | Lys | Leu | Lys | Val | Asp | Glu | Phe | Glu | Ser | Asn | Val | Asn | Glu | |
| | | | | 720 | | | | | 725 | | | | | 730 | | |

| GTG | AAG | GAC | CCC | TAC | CCT | TCA | GCT | GAC | TTC | CCA | GGG | GAT | GAT | GAG | GAG | 2319 |
|---|---|---|---|---|---|---|---|---|---|---|---|---|---|---|---|---|
| Val | Lys | Asp | Pro | Tyr | Pro | Ser | Ala | Asp | Phe | Pro | Gly | Asp | Asp | Glu | Glu | |
| | | | 735 | | | | | 740 | | | | | 745 | | | |

| GAC | GAG | CCT | GAG | ATC | CCA | GTG | AGC | CCC | CGA | CCG | CGC | CCG | CTG | GCC | GAG | 2367 |
|---|---|---|---|---|---|---|---|---|---|---|---|---|---|---|---|---|
| Asp | Glu | Pro | Glu | Ile | Pro | Val | Ser | Pro | Arg | Pro | Arg | Pro | Leu | Ala | Glu | |
| | | 750 | | | | | 755 | | | | | 760 | | | | |

| CTG | CAG | CTC | AAA | GAG | AAG | GCA | GTG | CCC | ATC | CCG | GAA | GCC | AGC | TCC | TTC | 2415 |
|---|---|---|---|---|---|---|---|---|---|---|---|---|---|---|---|---|
| Leu | Gln | Leu | Lys | Glu | Lys | Ala | Val | Pro | Ile | Pro | Glu | Ala | Ser | Ser | Phe | |
| 765 | | | | | 770 | | | | | 775 | | | | | | |

| TTC | ATC | TTC | AGT | CCC | ACC | AAT | AAG | GTC | CGT | GTC | CTG | TGT | CAC | CGC | ATC | 2463 |
|---|---|---|---|---|---|---|---|---|---|---|---|---|---|---|---|---|
| Phe | Ile | Phe | Ser | Pro | Thr | Asn | Lys | Val | Arg | Val | Leu | Cys | His | Arg | Ile | |
| 780 | | | | | 785 | | | | | 790 | | | | | 795 | |

| GTC | AAC | GCC | ACC | TGG | TTC | ACC | AAC | TTC | ATC | CTG | CTC | TTC | ATC | CTG | CTC | 2511 |
|---|---|---|---|---|---|---|---|---|---|---|---|---|---|---|---|---|
| Val | Asn | Ala | Thr | Trp | Phe | Thr | Asn | Phe | Ile | Leu | Leu | Phe | Ile | Leu | Leu | |
| | | | | 800 | | | | | 805 | | | | | 810 | | |

| AGC | AGT | GCT | GCG | CTG | GCC | GCC | GAG | GAC | CCC | ATC | CGG | GCG | GAG | TCC | GTG | 2559 |
|---|---|---|---|---|---|---|---|---|---|---|---|---|---|---|---|---|
| Ser | Ser | Ala | Ala | Leu | Ala | Ala | Glu | Asp | Pro | Ile | Arg | Ala | Glu | Ser | Val | |
| | | 815 | | | | | 820 | | | | | 825 | | | | |

| AGG | AAT | CAG | ATC | CTT | GGA | TAT | TTT | GAT | ATT | GCC | TTC | ACC | TCT | GTC | TTC | 2607 |
|---|---|---|---|---|---|---|---|---|---|---|---|---|---|---|---|---|
| Arg | Asn | Gln | Ile | Leu | Gly | Tyr | Phe | Asp | Ile | Ala | Phe | Thr | Ser | Val | Phe | |
| | | 830 | | | | | 835 | | | | | 840 | | | | |

| ACT | GTG | GAG | ATT | GTC | CTC | AAG | ATG | ACA | ACC | TAC | GGC | GCC | TTC | CTG | CAC | 2655 |
|---|---|---|---|---|---|---|---|---|---|---|---|---|---|---|---|---|
| Thr | Val | Glu | Ile | Val | Leu | Lys | Met | Thr | Thr | Tyr | Gly | Ala | Phe | Leu | His | |
| 845 | | | | | 850 | | | | | 855 | | | | | | |

| AAG | GGC | TCC | TTC | TGC | CGC | AAC | TAC | TTC | AAC | ATC | CTG | GAC | CTG | CTG | GTG | 2703 |
|---|---|---|---|---|---|---|---|---|---|---|---|---|---|---|---|---|
| Lys | Gly | Ser | Phe | Cys | Arg | Asn | Tyr | Phe | Asn | Ile | Leu | Asp | Leu | Leu | Val | |
| 860 | | | | | 865 | | | | | 870 | | | | | 875 | |

| GTG | GCC | GTG | TCT | CTC | ATC | TCC | ATG | GGT | CTC | GAG | TCC | AGC | ACC | ATC | TCC | 2751 |
|---|---|---|---|---|---|---|---|---|---|---|---|---|---|---|---|---|
| Val | Ala | Val | Ser | Leu | Ile | Ser | Met | Gly | Leu | Glu | Ser | Ser | Thr | Ile | Ser | |
| | | | | 880 | | | | | 885 | | | | | 890 | | |

| GTG | GTA | AAG | ATC | CTG | AGA | GTG | CTA | AGG | GTG | CTC | CGG | CCC | CTG | CGA | GCC | 2799 |
|---|---|---|---|---|---|---|---|---|---|---|---|---|---|---|---|---|
| Val | Val | Lys | Ile | Leu | Arg | Val | Leu | Arg | Val | Leu | Arg | Pro | Leu | Arg | Ala | |
| | | | 895 | | | | | 900 | | | | | 905 | | | |

| ATC | AAC | AGA | GCC | AAA | GGG | TTG | AAG | CAC | GTG | GTC | CAG | TGC | GTG | TTC | GTG | 2847 |
|---|---|---|---|---|---|---|---|---|---|---|---|---|---|---|---|---|
| Ile | Asn | Arg | Ala | Lys | Gly | Leu | Lys | His | Val | Val | Gln | Cys | Val | Phe | Val | |
| | | 910 | | | | | 915 | | | | | 920 | | | | |

| GCC | ATC | CGC | ACC | ATC | GGG | AAC | ATC | GTC | CTG | GTC | ACC | ACG | CTC | CTG | CAG | 2895 |

-continued

```
Ala Ile Arg Thr Ile Gly Asn Ile Val Leu Val Thr Thr Leu Leu Gln
        925                 930                 935

TTC ATG TTC GCC TGC ATC GGT GTC CAG CTC TTC AAG GGC AAG TTC TTC      2943
Phe Met Phe Ala Cys Ile Gly Val Gln Leu Phe Lys Gly Lys Phe Phe
    940                 945                 950                 955

AGC TGC AAT GAC CTA TCC AAG ATG ACA GAA GAG GAG TGC AGG GGC TAC      2991
Ser Cys Asn Asp Leu Ser Lys Met Thr Glu Glu Glu Cys Arg Gly Tyr
                960                 965                 970

TAC TAT GTG TAC AAG GAC GGG GAC CCC ACG CAG ATG GAG CTG CGC CCC      3039
Tyr Tyr Val Tyr Lys Asp Gly Asp Pro Thr Gln Met Glu Leu Arg Pro
            975                 980                 985

CGC CAG TGG ATA CAC AAT GAC TTC CAC TTT GAC AAC GTG CTG TCG GCC      3087
Arg Gln Trp Ile His Asn Asp Phe His Phe Asp Asn Val Leu Ser Ala
        990                 995                 1000

ATG ATG TCG CTC TTC ACG GTG TCC ACC TTC GAG GGA TGG CCC CAG CTG      3135
Met Met Ser Leu Phe Thr Val Ser Thr Phe Glu Gly Trp Pro Gln Leu
    1005                1010                1015

CTG TAC AGG GCC ATA GAC TCC AAC GAG GAG GAC ATG GGC CCC GTT TAC      3183
Leu Tyr Arg Ala Ile Asp Ser Asn Glu Glu Asp Met Gly Pro Val Tyr
1020                1025                1030                1035

AAC AAC CGA GTG GAG ATG GCC ATC TTC TTC ATC ATC TAC ATC ATC CTC      3231
Asn Asn Arg Val Glu Met Ala Ile Phe Phe Ile Ile Tyr Ile Ile Leu
                1040                1045                1050

ATT GCC TTC TTC ATG ATG AAC ATC TTT GTG GGC TTT GTC ATC GTC ACC      3279
Ile Ala Phe Phe Met Met Asn Ile Phe Val Gly Phe Val Ile Val Thr
            1055                1060                1065

TTC CAG GAG CAG GGG GAG ACG GAG TAC AAG AAC TGC GAG CTG GAC AAG      3327
Phe Gln Glu Gln Gly Glu Thr Glu Tyr Lys Asn Cys Glu Leu Asp Lys
        1070                1075                1080

AAC CAG CGC CAG TGT GTG CAG TAT GCC CTG AAG GCC CGC CCA CTT CGG      3375
Asn Gln Arg Gln Cys Val Gln Tyr Ala Leu Lys Ala Arg Pro Leu Arg
    1085                1090                1095

TGC TAC ATC CCC AAG AAC CCA TAC CAG TAC CAG GTG TGG TAC GTC GTC      3423
Cys Tyr Ile Pro Lys Asn Pro Tyr Gln Tyr Gln Val Trp Tyr Val Val
1100                1105                1110                1115

ACC TCC TCC TAC TTT GAA TAC CTG ATG TTC GCC CTC ATC ATG CTC AAC      3471
Thr Ser Ser Tyr Phe Glu Tyr Leu Met Phe Ala Leu Ile Met Leu Asn
                1120                1125                1130

ACC ATC TGC CTG GGC ATG CAG CAC TAC CAC CAG TCG GAG GAG ATG AAC      3519
Thr Ile Cys Leu Gly Met Gln His Tyr His Gln Ser Glu Glu Met Asn
            1135                1140                1145

CAC ATC TCA GAC ATC CTC AAT GTG GCC TTC ACC ATC ATC TTC ACG CTG      3567
His Ile Ser Asp Ile Leu Asn Val Ala Phe Thr Ile Ile Phe Thr Leu
        1150                1155                1160

GAG ATG ATT CTC AAG CTC TTG GCG TTC AAG GCC AGG GGC TAT TTC GGA      3615
Glu Met Ile Leu Lys Leu Leu Ala Phe Lys Ala Arg Gly Tyr Phe Gly
    1165                1170                1175

GAC CCC TGG AAT GTG TTC GAC TTC CTG ATC GTC ATC GGC AGC ATC ATT      3663
Asp Pro Trp Asn Val Phe Asp Phe Leu Ile Val Ile Gly Ser Ile Ile
1180                1185                1190                1195

GAC GTC ATC CTC AGC GAG ATC GAC ACT TTC CTG GCC TCC AGC GGG GGA      3711
Asp Val Ile Leu Ser Glu Ile Asp Thr Phe Leu Ala Ser Ser Gly Gly
                1200                1205                1210

CTG TAT TGC CTG GGT GGC GGC TGC GGG AAC GTT GAC CCA GAC GAG AGC      3759
Leu Tyr Cys Leu Gly Gly Gly Cys Gly Asn Val Asp Pro Asp Glu Ser
            1215                1220                1225

GCC CGC ATC TCC AGT GCC TTC TTC CGC CTG TTC CGG GTT ATG AGG CTG      3807
Ala Arg Ile Ser Ser Ala Phe Phe Arg Leu Phe Arg Val Met Arg Leu
        1230                1235                1240

ATC AAG CTG CTG AGT CGG GCC GAG GGC GTG CGC ACG CTG CTG TGG ACG      3855
```

-continued

```
Ile Lys Leu Leu Ser Arg Ala Glu Gly Val Arg Thr Leu Leu Trp Thr
1245                1250                1255

TTC ATC AAG TCC TTC CAG GCC CTG CCC TAC GTG GCC CTG CTC ATC GTC    3903
Phe Ile Lys Ser Phe Gln Ala Leu Pro Tyr Val Ala Leu Leu Ile Val
    1260                1265                1270                1275

ATG CTG TTC TTC ATC TAC GCC GTC ATC GGC ATG CAG ATG TTT GGA AAG    3951
Met Leu Phe Phe Ile Tyr Ala Val Ile Gly Met Gln Met Phe Gly Lys
                1280                1285                1290

ATC GCC CTG GTG GAC GGG ACC CAG ATC AAC CGC AAC AAC AAC TTC CAG    3999
Ile Ala Leu Val Asp Gly Thr Gln Ile Asn Arg Asn Asn Asn Phe Gln
            1295                1300                1305

ACC TTC CCG CAG GCC GTG CTG CTC TTC AGG TGT GCA ACA GGG GAG        4047
Thr Phe Pro Gln Ala Val Leu Leu Phe Arg Cys Ala Thr Gly Glu
        1310                1315                1320

GCG TGG CAA GAG ATC CTG CTG GCC TGC AGC TAC GGG AAG TTG TGC GAC    4095
Ala Trp Gln Glu Ile Leu Leu Ala Cys Ser Tyr Gly Lys Leu Cys Asp
    1325                1330                1335

CCA GAG TCA GAC TAC GCC CCG GGC GAG GAG TAC ACG TGT GGC ACC AAC    4143
Pro Glu Ser Asp Tyr Ala Pro Gly Glu Glu Tyr Thr Cys Gly Thr Asn
1340                1345                1350                1355

TTC GCC TAC TAC TAC TTC ATC AGC TTC TAC ATG CTC TGC GCC TTC CTG    4191
Phe Ala Tyr Tyr Tyr Phe Ile Ser Phe Tyr Met Leu Cys Ala Phe Leu
                1360                1365                1370

ATC ATC AAC CTC TTC GTG GCT GTC ATC ATG GAC AAC TTT GAC TAC CTG    4239
Ile Ile Asn Leu Phe Val Ala Val Ile Met Asp Asn Phe Asp Tyr Leu
            1375                1380                1385

ACA CGC GAC TGG TCC ATC CTG GGC CCT CAC CAC CTG GAC GAG TTC AAG    4287
Thr Arg Asp Trp Ser Ile Leu Gly Pro His His Leu Asp Glu Phe Lys
        1390                1395                1400

GCC ATC TGG GCA GAG TAT GAC CCA GAG GCC AAG GGG CGA ATC AAG CAC    4335
Ala Ile Trp Ala Glu Tyr Asp Pro Glu Ala Lys Gly Arg Ile Lys His
    1405                1410                1415

CTG GAC GTG GTG ACC CTG CTG AGA AGG ATC CAG CCC CCT CTG GGC TTC    4383
Leu Asp Val Val Thr Leu Leu Arg Arg Ile Gln Pro Pro Leu Gly Phe
1420                1425                1430                1435

GGG AAG TTC TGT CCA CAC CGG GTG GCC TGT AAG CGC CTG GTG GGC ATG    4431
Gly Lys Phe Cys Pro His Arg Val Ala Cys Lys Arg Leu Val Gly Met
                1440                1445                1450

AAC ATG CCC CTG AAC AGT GAC GGC ACG GTC ACC TTC AAT GCC ACG CTC    4479
Asn Met Pro Leu Asn Ser Asp Gly Thr Val Thr Phe Asn Ala Thr Leu
            1455                1460                1465

TTT GCC CTG GTG CGC ACG GCC CTC AAG ATC AAG ACA GAA GGT AAC TTC    4527
Phe Ala Leu Val Arg Thr Ala Leu Lys Ile Lys Thr Glu Gly Asn Phe
        1470                1475                1480

GAG CAG GCC AAC GAG GAG CTG AGG GCC ATC ATC AAG AAG ATC TGG AAG    4575
Glu Gln Ala Asn Glu Glu Leu Arg Ala Ile Ile Lys Lys Ile Trp Lys
    1485                1490                1495

AGA ACC AGC ATG AAG CTA CTG GAC CAG GTC ATC CCT CCC ATA GGA GAT    4623
Arg Thr Ser Met Lys Leu Leu Asp Gln Val Ile Pro Pro Ile Gly Asp
1500                1505                1510                1515

GAC GAG GTG ACC GTG GGG AAG TTC TAC GCC ACA TTC CTC ATC CAG GAG    4671
Asp Glu Val Thr Val Gly Lys Phe Tyr Ala Thr Phe Leu Ile Gln Glu
                1520                1525                1530

CAC TTC CGG AAG TTC ATG AAG CGC CAG GAG GAA TAT TAT GGG TAT CGG    4719
His Phe Arg Lys Phe Met Lys Arg Gln Glu Glu Tyr Tyr Gly Tyr Arg
            1535                1540                1545

CCC AAG AAG GAC ACC GTG CAG ATC CAG GCT GGG CTG CGG ACC ATA GAG    4767
Pro Lys Lys Asp Thr Val Gln Ile Gln Ala Gly Leu Arg Thr Ile Glu
        1550                1555                1560

GAG GAG GCG GCC CCT GAG ATC CGC CGC ACC ATC TCA GGA GAC CTG ACC    4815
```

-continued

```
                Glu Glu Ala Ala Pro Glu Ile Arg Arg Thr Ile Ser Gly Asp Leu Thr
                1565                1570                1575

GCC GAG GAG GAG CTG GAG AGA GCC ATG GTG GAG GCT GCG ATG GAG GAG        4863
Ala Glu Glu Glu Leu Glu Arg Ala Met Val Glu Ala Ala Met Glu Glu
1580                1585                1590                1595

AGG ATC TTC CGG AGG ACC GGA GGC CTG TTT GGC CAG GTG GAC ACC TTC        4911
Arg Ile Phe Arg Arg Thr Gly Gly Leu Phe Gly Gln Val Asp Thr Phe
                1600                1605                1610

CTG GAA AGG ACC AAC TCC CTA CCC CCG GTG ATG GCC AAC CAA AGA CCG        4959
Leu Glu Arg Thr Asn Ser Leu Pro Pro Val Met Ala Asn Gln Arg Pro
            1615                1620                1625

CTC CAG TTT GCT GAG ATA GAA ATG GAA GAG CTT GAG TCG CCT GTC TTC        5007
Leu Gln Phe Ala Glu Ile Glu Met Glu Glu Leu Glu Ser Pro Val Phe
        1630                1635                1640

TTG GAG GAC TTC CCT CAA GAC GCA AGA ACC AAC CCT CTC GCT CGT GCC        5055
Leu Glu Asp Phe Pro Gln Asp Ala Arg Thr Asn Pro Leu Ala Arg Ala
    1645                1650                1655

AAT ACC AAC AAC GCC AAT GCC AAT GTT GCC TAT GGC AAC AGC AAC CAT        5103
Asn Thr Asn Asn Ala Asn Ala Asn Val Ala Tyr Gly Asn Ser Asn His
1660                1665                1670                1675

AGC AAC AAC CAG ATG TTT TCC AGC GTC CAC TGT GAA AGG GAG TTC CCG        5151
Ser Asn Asn Gln Met Phe Ser Ser Val His Cys Glu Arg Glu Phe Pro
                1680                1685                1690

GGA GAG GCG GAG ACA CCG GCT GCC GGA CGA GGA GCC CTC AGC CAC TCC        5199
Gly Glu Ala Glu Thr Pro Ala Ala Gly Arg Gly Ala Leu Ser His Ser
            1695                1700                1705

CAC AGG GCC CTG GGA CCT CAC AGC AAG CCC TGT GCT GGA AAA CTG AAT        5247
His Arg Ala Leu Gly Pro His Ser Lys Pro Cys Ala Gly Lys Leu Asn
        1710                1715                1720

GGG CAG CTG GTC CAG CCG GGA ATG CCC ATC AAC CAG GCA CCT CCT GCC        5295
Gly Gln Leu Val Gln Pro Gly Met Pro Ile Asn Gln Ala Pro Pro Ala
    1725                1730                1735

CCC TGC CAG CAG CCT AGC ACA GAT CCC CCA GAG CGC GGG CAG AGG AGG        5343
Pro Cys Gln Gln Pro Ser Thr Asp Pro Pro Glu Arg Gly Gln Arg Arg
1740                1745                1750                1755

ACC TCC CTG ACA GGG TCT CTG CAA GAC GAA GCA CCC CAG AGG AGG AGC        5391
Thr Ser Leu Thr Gly Ser Leu Gln Asp Glu Ala Pro Gln Arg Arg Ser
                1760                1765                1770

TCC GAG GGG AGC ACC CCC AGG CGC CCG GCT CCT GCT ACA GCT CTG CTG        5439
Ser Glu Gly Ser Thr Pro Arg Arg Pro Ala Pro Ala Thr Ala Leu Leu
            1775                1780                1785

ATC CAA GAG GCT CTG GTT CGA GGG GGC CTG GAC ACC TTG GCA GCT GAT        5487
Ile Gln Glu Ala Leu Val Arg Gly Gly Leu Asp Thr Leu Ala Ala Asp
        1790                1795                1800

GCT GGC TTC GTC ATG GCA ACA AGC CAG GCC CTG GTA GAC GCC TGT CAG        5535
Ala Gly Phe Val Met Ala Thr Ser Gln Ala Leu Val Asp Ala Cys Gln
    1805                1810                1815

ATG GAA CCG GAG GAA GTA GAG GTC GCA GCC ACA GAG CTA CTG AAA GAG        5583
Met Glu Pro Glu Glu Val Glu Val Ala Ala Thr Glu Leu Leu Lys Glu
1820                1825                1830                1835

CGA GAG TCC GTC CAG GGC ATG GCC AGT GTC CCG GGA AGC CTG AGC CGC        5631
Arg Glu Ser Val Gln Gly Met Ala Ser Val Pro Gly Ser Leu Ser Arg
                1840                1845                1850

AGG TCC TCC CTG GGC AGC CTT GAC CAG GTC CAG GGC TCC CAG GAA ACC        5679
Arg Ser Ser Leu Gly Ser Leu Asp Gln Val Gln Gly Ser Gln Glu Thr
            1855                1860                1865

CTT ATT CCT CCC AGG CCG TGA TGGCTGTGCA GTGTCCACAT GACCAAGGCG AGGGG     5735
Leu Ile Pro Pro Arg Pro  *
        1870

GACAGTGCGT GCAGAAGCTC AGCCCTGCAT GGCAGCCTCC CTCTGTCTCA GCCCTCCTGC      5795
```

-continued

```
TGAGCTGGGG CGGTCTGGAA CCGACCAGGA AGCCAGGAGC CTCCCCTGGC CAGCAAGAGG    5855

CATGATTCTA AAGCATCCAG AAAGGCCTGG TCAGTGCCAC TCCCCAGCAG GACATTAAAG    5915

TCTCTAGGTC TGTGGCAAAA AAAAAAAAAA AAAAAAAAAA AAAAAAAAAA AAAAAAAAAA    5975

(2) INFORMATION FOR SEQ ID NO:2:

(i) SEQUENCE CHARACTERISTICS:
        (A) LENGTH: 3802 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 309...3630
        (A) NAME/KEY: mat_peptide
        (B) LOCATION: 387...3626
        (D) OTHER INFORMATION:

(xi) SEQUENCE DESCRIPTION: SEQ ID NO:2:

AGAAGGGAGG GCGAGCGTGG TGTGTGCGCG CTCGGGCGCC GGCGGCACCG CCGAGGTCTG      60

TTGGCAAAAG TCGCCCTTGA TGGCGGCGGA GGCGAGGCAG CCGCGGCGCC GAACAGCCGA     120

CGCGCGCTAG CGGGGTCCGC CCGCCCCTTT CCCAGAGCCC AGCGCCGCCG TTCGCCGCCG     180

CCGCCGCCCG CCCGCGCGCC GTTCGCCGCC GCCGCCGCCC GCGGGTGGCA GCGCCGCTCG     240

GTCCCCGGCC CCGGGGCCGG CTGGGGGGCG GTCGGGGCGT GTGAGGGGCT TGCTCCCAGC     300

TCGCGAAG ATG GCT GCG GGC CGC CCG CTG GCC TGG ACG CTG ACA CTT TGG     350
         Met Ala Ala Gly Arg Pro Leu Ala Trp Thr Leu Thr Leu Trp
         -26 -25              -20                  -15

CAG GCG TGG CTG ATC CTG ATC GGG CCC TCG TCG GAG GAG CCG TTC CCT     398
Gln Ala Trp Leu Ile Leu Ile Gly Pro Ser Ser Glu Glu Pro Phe Pro
       -10                  -5                  -1   1

TCA GCC GTC ACT ATC AAG TCA TGG GTG GAT AAG ATG CAA GAA GAC CTG     446
Ser Ala Val Thr Ile Lys Ser Trp Val Asp Lys Met Gln Glu Asp Leu
 5               10                  15                  20

GTC ACA CTG GCA AAA ACA GCA AGT GGA GTC AAT CAG CTT GTT GAT ATT     494
Val Thr Leu Ala Lys Thr Ala Ser Gly Val Asn Gln Leu Val Asp Ile
             25                  30                  35

TAT GAG AAA TAT CAA GAT TTG TAT ACT GTG GAA CCA AAT AAT GCA CGT     542
Tyr Glu Lys Tyr Gln Asp Leu Tyr Thr Val Glu Pro Asn Asn Ala Arg
         40                  45                  50

CAG CTG GTG GAA ATT GCA GCC AGA GAC ATT GAG AAG CTT CTC AGC AAC     590
Gln Leu Val Glu Ile Ala Ala Arg Asp Ile Glu Lys Leu Leu Ser Asn
     55                  60                  65

AGA TCT AAA GCC CTG GTG CGC CTG GCT TTG GAA GCA GAG AAA GTT CAA     638
Arg Ser Lys Ala Leu Val Arg Leu Ala Leu Glu Ala Glu Lys Val Gln
 70                  75                  80

GCA GCC CAC CAA TGG AGG GAA GAT TTT GCA AGC AAT GAA GTT GTC TAC     686
Ala Ala His Gln Trp Arg Glu Asp Phe Ala Ser Asn Glu Val Val Tyr
85                  90                  95                 100

TAT AAC GCG AAG GAT GAT CTT GAT CCT GAA AAA AAT GAC AGT GAA CCA     734
Tyr Asn Ala Lys Asp Asp Leu Asp Pro Glu Lys Asn Asp Ser Glu Pro
                105                 110                 115

GGC AGC CAG AGG ATC AAA CCT GTT TTC ATT GAC GAT GCT AAC TTT AGA     782
Gly Ser Gln Arg Ile Lys Pro Val Phe Ile Asp Asp Ala Asn Phe Arg
            120                 125                 130

AGA CAA GTA TCC TAT CAG CAC GCA GCT GTC CAT ATC CCC ACT GAC ATC     830
Arg Gln Val Ser Tyr Gln His Ala Ala Val His Ile Pro Thr Asp Ile
        135                 140                 145
```

-continued

```
TAT GAA GGA TCG ACA ATC GTG TTA AAC GAA CTC AAC TGG ACA AGT GCC      878
Tyr Glu Gly Ser Thr Ile Val Leu Asn Glu Leu Asn Trp Thr Ser Ala
150                 155                 160

TTA GAT GAC GTT TTC AAA AAA AAT CGA GAG GAA GAC CCT TCA CTG TTG      926
Leu Asp Asp Val Phe Lys Lys Asn Arg Glu Glu Asp Pro Ser Leu Leu
165                 170                 175                 180

TGG CAG GTG TTT GGC AGT GCC ACT GGC CTG GCC CGG TAT TAC CCA GCT      974
Trp Gln Val Phe Gly Ser Ala Thr Gly Leu Ala Arg Tyr Tyr Pro Ala
                185                 190                 195

TCT CCA TGG GTT GAT AAT AGC CGA ACC CCA AAC AAG ATT GAT CTT TAT     1022
Ser Pro Trp Val Asp Asn Ser Arg Thr Pro Asn Lys Ile Asp Leu Tyr
                200                 205                 210

GAT GTA CGC AGA AGA CCA TGG TAC ATC CAA GGT GCT GCA TCC CCT AAA     1070
Asp Val Arg Arg Arg Pro Trp Tyr Ile Gln Gly Ala Ala Ser Pro Lys
            215                 220                 225

GAT ATG CTT ATT CTG GTG GAT GTG AGT GGA AGC GTT AGT GGA CTG ACA     1118
Asp Met Leu Ile Leu Val Asp Val Ser Gly Ser Val Ser Gly Leu Thr
230                 235                 240

CTC AAA CTC ATC CGG ACA TCC GTC TCC GAA ATG TTG GAA ACC CTC TCA     1166
Leu Lys Leu Ile Arg Thr Ser Val Ser Glu Met Leu Glu Thr Leu Ser
245                 250                 255                 260

GAT GAT GAT TTT GTG AAC GTG GCT TCA TTT AAC AGC AAT GCT CAG GAT     1214
Asp Asp Asp Phe Val Asn Val Ala Ser Phe Asn Ser Asn Ala Gln Asp
                265                 270                 275

GTA AGC TGC TTT CAG CAC CTT GTC CAA GCA AAT GTA AGA AAT AAG AAA     1262
Val Ser Cys Phe Gln His Leu Val Gln Ala Asn Val Arg Asn Lys Lys
                280                 285                 290

GTG TTG AAA GAT GCA GTG AAT AAT ATC ACA GCA AAA GGA ATC ACA GAT     1310
Val Leu Lys Asp Ala Val Asn Asn Ile Thr Ala Lys Gly Ile Thr Asp
            295                 300                 305

TAT AAG AAG GGC TTT AGT TTT GCT TTT GAG CAG CTG CTT AAT TAT AAT     1358
Tyr Lys Lys Gly Phe Ser Phe Ala Phe Glu Gln Leu Leu Asn Tyr Asn
310                 315                 320

GTA TCC AGA GCC AAC TGC AAT AAG ATT ATC ATG TTG TTC ACG GAC GGA     1406
Val Ser Arg Ala Asn Cys Asn Lys Ile Ile Met Leu Phe Thr Asp Gly
325                 330                 335                 340

GGA GAA GAG AGA GCC CAG GAG ATA TTT GCC AAA TAC AAT AAA GAC AAG     1454
Gly Glu Glu Arg Ala Gln Glu Ile Phe Ala Lys Tyr Asn Lys Asp Lys
                345                 350                 355

AAA GTA CGT GTA TTC ACA TTC TCA GTT GGC CAA CAT AAT TAC GAC AGA     1502
Lys Val Arg Val Phe Thr Phe Ser Val Gly Gln His Asn Tyr Asp Arg
            360                 365                 370

GGA CCT ATT CAG TGG ATG GCT TGC GAA AAT AAA GGT TAT TAT TAT GAA     1550
Gly Pro Ile Gln Trp Met Ala Cys Glu Asn Lys Gly Tyr Tyr Tyr Glu
            375                 380                 385

ATT CCA TCC ATT GGA GCC ATA AGA ATT AAT ACT CAG GAA TAC CTA GAT     1598
Ile Pro Ser Ile Gly Ala Ile Arg Ile Asn Thr Gln Glu Tyr Leu Asp
390                 395                 400

GTT CTG GGA AGA CCG ATG GTT TTA GCA GGA GAC AAA GCT AAG CAA GTC     1646
Val Leu Gly Arg Pro Met Val Leu Ala Gly Asp Lys Ala Lys Gln Val
405                 410                 415                 420

CAA TGG ACA AAT GTG TAC CTG GAT GCA CTG GAA CTG GGA CTT GTC ATT     1694
Gln Trp Thr Asn Val Tyr Leu Asp Ala Leu Glu Leu Gly Leu Val Ile
                425                 430                 435

ACT GGA ACT CTT CCG GTC TTC AAC ATA ACT GGC CAA TTT GAA AAT AAG     1742
Thr Gly Thr Leu Pro Val Phe Asn Ile Thr Gly Gln Phe Glu Asn Lys
                440                 445                 450

ACA AAC TTA AAG AAC CAG CTG ATT CTT GGA GTG ATG GGA GTT GAT GTG     1790
Thr Asn Leu Lys Asn Gln Leu Ile Leu Gly Val Met Gly Val Asp Val
            455                 460                 465
```

```
TCT TTG GAA GAT ATT AAA AGA CTG ACA CCA CGT TTT ACA CTC TGC CCC    1838
Ser Leu Glu Asp Ile Lys Arg Leu Thr Pro Arg Phe Thr Leu Cys Pro
    470                 475                 480

AAT GGC TAC TAT TTT GCA ATT GAT CCT AAT GGT TAT GTG TTA TTA CAT    1886
Asn Gly Tyr Tyr Phe Ala Ile Asp Pro Asn Gly Tyr Val Leu Leu His
485                 490                 495                 500

CCA AAT CTT CAG CCA AAG CCT ATT GGT GTA GGT ATA CCA ACA ATT AAT    1934
Pro Asn Leu Gln Pro Lys Pro Ile Gly Val Gly Ile Pro Thr Ile Asn
                505                 510                 515

TTG AGA AAA AGG AGA CCC AAT GTT CAG AAC CCC AAA TCT CAG GAG CCA    1982
Leu Arg Lys Arg Arg Pro Asn Val Gln Asn Pro Lys Ser Gln Glu Pro
        520                 525                 530

GTG ACA TTG GAT TTC CTC GAT GCA GAG TTG GAG AAT GAC ATT AAA GTG    2030
Val Thr Leu Asp Phe Leu Asp Ala Glu Leu Glu Asn Asp Ile Lys Val
            535                 540                 545

GAG ATT CGA AAT AAA ATG ATC GAT GGA GAA AGT GGA GAA AAA ACA TTC    2078
Glu Ile Arg Asn Lys Met Ile Asp Gly Glu Ser Gly Glu Lys Thr Phe
    550                 555                 560

AGA ACT CTG GTT AAA TCT CAA GAT GAG AGA TAT ATT GAC AAA GGA AAC    2126
Arg Thr Leu Val Lys Ser Gln Asp Glu Arg Tyr Ile Asp Lys Gly Asn
565                 570                 575                 580

AGG ACA TAC ACG TGG ACT CCT GTC AAC GGC ACA GAT TAT AGC AGT TTG    2174
Arg Thr Tyr Thr Trp Thr Pro Val Asn Gly Thr Asp Tyr Ser Ser Leu
                585                 590                 595

GCC TTG GTA TTA CCA ACC TAC AGT TTT TAC TAT ATA AAA GCC AAA ATA    2222
Ala Leu Val Leu Pro Thr Tyr Ser Phe Tyr Tyr Ile Lys Ala Lys Ile
        600                 605                 610

GAA GAG ACA ATA ACT CAG GCC AGA TAT TCA GAA ACA CTG AAA CCG GAT    2270
Glu Glu Thr Ile Thr Gln Ala Arg Tyr Ser Glu Thr Leu Lys Pro Asp
            615                 620                 625

AAT TTT GAA GAA TCT GGC TAC ACA TTC CTA GCA CCA AGA GAT TAC TGC    2318
Asn Phe Glu Glu Ser Gly Tyr Thr Phe Leu Ala Pro Arg Asp Tyr Cys
    630                 635                 640

AGT GAC CTT AAA CCT TCA GAT AAT AAC ACT GAA TTT CTT TTA AAT TTC    2366
Ser Asp Leu Lys Pro Ser Asp Asn Asn Thr Glu Phe Leu Leu Asn Phe
645                 650                 655                 660

AAT GAG TTT ATT GAT AGA AAA ACT CCA AAC AAC CCA TCC TGT AAT ACA    2414
Asn Glu Phe Ile Asp Arg Lys Thr Pro Asn Asn Pro Ser Cys Asn Thr
                665                 670                 675

GAC TTG ATT AAT AGA GTC TTG CTG GAT GCA GGC TTT ACA AAT GAA CTT    2462
Asp Leu Ile Asn Arg Val Leu Leu Asp Ala Gly Phe Thr Asn Glu Leu
        680                 685                 690

GTT CAA AAT TAC TGG AGT AAG CAG AAG AAT ATC AAG GGA GTG AAA GCA    2510
Val Gln Asn Tyr Trp Ser Lys Gln Lys Asn Ile Lys Gly Val Lys Ala
            695                 700                 705

CGG TTT GTT GTG ACT GAT GGT GGG ATT ACC AGA GTT TAT CCC AAA GAG    2558
Arg Phe Val Val Thr Asp Gly Gly Ile Thr Arg Val Tyr Pro Lys Glu
    710                 715                 720

GCT GGA GAA AAT TGG CAG GAA AAC CCA GAG ACA TAT GAA GAC AGC TTC    2606
Ala Gly Glu Asn Trp Gln Glu Asn Pro Glu Thr Tyr Glu Asp Ser Phe
725                 730                 735                 740

TAT AAA AGG AGC CTC GAT AAT GAT AAC TAC GTT TTC ACT GCT CCC TAC    2654
Tyr Lys Arg Ser Leu Asp Asn Asp Asn Tyr Val Phe Thr Ala Pro Tyr
                745                 750                 755

TTT AAC AAA AGT GGA CCT GGG GCC TAT GAG TCA GGC ATT ATG GTA AGC    2702
Phe Asn Lys Ser Gly Pro Gly Ala Tyr Glu Ser Gly Ile Met Val Ser
        760                 765                 770

AAA GCT GTA GAA ATA TAT ATC CAA GGA AAA CTT CTT AAA CCT GCA GTT    2750
Lys Ala Val Glu Ile Tyr Ile Gln Gly Lys Leu Leu Lys Pro Ala Val
            775                 780                 785
```

```
GTT GGA ATT AAA ATT GAT GTA AAT TCT TGG ATA GAG AAT TTC ACC AAA    2798
Val Gly Ile Lys Ile Asp Val Asn Ser Trp Ile Glu Asn Phe Thr Lys
        790                 795                 800

ACT TCA ATC AGG GAT CCG TGT GCT GGT CCA GTT TGT GAC TGC AAA CGA    2846
Thr Ser Ile Arg Asp Pro Cys Ala Gly Pro Val Cys Asp Cys Lys Arg
805                 810                 815                 820

AAC AGT GAT GTA ATG GAT TGT GTG ATT CTA GAT GAC GGT GGG TTT CTT    2894
Asn Ser Asp Val Met Asp Cys Val Ile Leu Asp Asp Gly Gly Phe Leu
                825                 830                 835

TTG ATG GCC AAC CAT GAT GAT TAT ACC AAT CAG ATT GGA AGA TTC TTT    2942
Leu Met Ala Asn His Asp Asp Tyr Thr Asn Gln Ile Gly Arg Phe Phe
            840                 845                 850

GGA GAG ATT GAT CCA AGC TTG ATG AGA CAC CTG GTC AAT ATA TCA GTT    2990
Gly Glu Ile Asp Pro Ser Leu Met Arg His Leu Val Asn Ile Ser Val
        855                 860                 865

TAT GCC TTT AAC AAA TCT TAT GAT TAT CAG TCG GTG TGT GAA CCT GGT    3038
Tyr Ala Phe Asn Lys Ser Tyr Asp Tyr Gln Ser Val Cys Glu Pro Gly
870                 875                 880

GCT GCG CCA AAG CAG GGA GCA GGG CAC CGC TCG GCT TAT GTG CCA TCA    3086
Ala Ala Pro Lys Gln Gly Ala Gly His Arg Ser Ala Tyr Val Pro Ser
                885                 890                 895                 900

ATA GCA GAC ATA CTG CAG ATT GGA TGG TGG GCC ACT GCT GCT GCC TGG    3134
Ile Ala Asp Ile Leu Gln Ile Gly Trp Trp Ala Thr Ala Ala Ala Trp
            905                 910                 915

TCT ATT CTT CAG CAG TTT CTG TTG AGT TTG ACT TTT CCA CGG CTC CTT    3182
Ser Ile Leu Gln Gln Phe Leu Leu Ser Leu Thr Phe Pro Arg Leu Leu
        920                 925                 930

GAG GCA GCT GAT ATG GAG GAT GAC GAC TTC ACT GCC TCC ATG TCA AAG    3230
Glu Ala Ala Asp Met Glu Asp Asp Asp Phe Thr Ala Ser Met Ser Lys
    935                 940                 945

CAG AGC TGC ATC ACT GAG CAA ACC CAG TAT TTC TTC GAT AAT GAC AGC    3278
Gln Ser Cys Ile Thr Glu Gln Thr Gln Tyr Phe Phe Asp Asn Asp Ser
950                 955                 960

AAA TCG TTC AGT GGG GTA TTA GAC TGT GGG AAT TGT TCC AGA ATC TTT    3326
Lys Ser Phe Ser Gly Val Leu Asp Cys Gly Asn Cys Ser Arg Ile Phe
965                 970                 975                 980

CAT GTA GAA AAG CTC ATG AAC ACC AAT TTA ATA TTC ATA ATG GTA GAG    3374
His Val Glu Lys Leu Met Asn Thr Asn Leu Ile Phe Ile Met Val Glu
            985                 990                 995

AGC AAG GGG ACA TGT CCC TGT GAC ACA CGG CTG CTC ATA CAA GCA GAG    3422
Ser Lys Gly Thr Cys Pro Cys Asp Thr Arg Leu Leu Ile Gln Ala Glu
        1000                1005                1010

CAA ACT TCT GAT GGA CCA GAT CCT TGT GAT ATG GTT AAG CAA CCC AGA    3470
Gln Thr Ser Asp Gly Pro Asp Pro Cys Asp Met Val Lys Gln Pro Arg
    1015                1020                1025

TAT CGA AAA GGG CCA GAT GTC TGC TTT GAC AAC AAT GTC CTG GAG GAT    3518
Tyr Arg Lys Gly Pro Asp Val Cys Phe Asp Asn Asn Val Leu Glu Asp
1030                1035                1040

TAT ACT GAC TGC GGT GGG GTC TCT GGA TTA AAT CCT TCC CTG TGG TCC    3566
Tyr Thr Asp Cys Gly Gly Val Ser Gly Leu Asn Pro Ser Leu Trp Ser
1045                1050                1055                1060

ATC ATC GGG ATA CAG TTT GTA CTG CTT TGG CTG GTT TCT GGC AGC AGA    3614
Ile Ile Gly Ile Gln Phe Val Leu Leu Trp Leu Val Ser Gly Ser Arg
            1065                1070                1075

CAC TGC CTG TTA TGA C CTTCTAAAAC CAAATCTCCA TAATTAAACT CCAGACCCTG    3670
His Cys Leu Leu *
            1080

CCACAACATG ATCCCTCCGT TATGTTAAAG TAGGGTCAAC TGTTAAATCA GAACATTAGC    3730

TGGGCCTCTG CCATGGCAGA GCCCTAAGGC GCAGACTCAT CAGGCACCCA CTGGCTGCAT    3790
```

-continued

```
GTCAGGGTGT CC                                                      3802
```

(2) INFORMATION FOR SEQ ID NO:3:

(i) SEQUENCE CHARACTERISTICS:
        (A) LENGTH: 1560 base pairs
        (B) TYPE: nucleic acid
        (C) STRANDEDNESS: single
        (D) TOPOLOGY: unknown (ii) MOLECULE TYPE: Genomic DNA (ix) FEATURE:
        (A) NAME/KEY: Coding Sequence
        (B) LOCATION: 35...1558

(xi) SEQUENCE DESCRIPTION: SEQ ID NO:3:

```
GGGCGGGGGA GGGGGATTGA TCTTCGATCG CAAG ATG GCT GCT GGC TGC CTG CTG      55
                                     Met Ala Ala Gly Cys Leu Leu
                                      1               5

GCC TTG ACT CTG ACA CTT TTC CAA TCT TTG CTC ATC GGC CCC TCG TCG      103
Ala Leu Thr Leu Thr Leu Phe Gln Ser Leu Leu Ile Gly Pro Ser Ser
         10                  15                  20

GAG GAG CCG TTC CCT TCG GCC GTC ACT ATC AAA TCA TGG GTG GAT AAG      151
Glu Glu Pro Phe Pro Ser Ala Val Thr Ile Lys Ser Trp Val Asp Lys
 25                  30                  35

ATG CAA GAA GAC CTT GTC ACA CTG GCA AAA ACA GCA AGT GGA GTC AAT      199
Met Gln Glu Asp Leu Val Thr Leu Ala Lys Thr Ala Ser Gly Val Asn
 40                  45                  50                  55

CAG CTT GTT GAT ATT TAT GAG AAA TAT CAA GAT TTG TAT ACT GTG GAA      247
Gln Leu Val Asp Ile Tyr Glu Lys Tyr Gln Asp Leu Tyr Thr Val Glu
                 60                  65                  70

CCA AAT AAT GCA CGC CAG CTG GTA GAA ATT GCA GCC AGG GAT ATT GAG      295
Pro Asn Asn Ala Arg Gln Leu Val Glu Ile Ala Ala Arg Asp Ile Glu
             75                  80                  85

AAA CTT CTG AGC AAC AGA TCT AAA GCC CTG GTG AGC CTG GCA TTG GAA      343
Lys Leu Leu Ser Asn Arg Ser Lys Ala Leu Val Ser Leu Ala Leu Glu
         90                  95                 100

GCG GAG AAA GTT CAA GCA GCT CAC CAG TGG AGA GAA GAT TTT GCA AGC      391
Ala Glu Lys Val Gln Ala Ala His Gln Trp Arg Glu Asp Phe Ala Ser
105                 110                 115

AAT GAA GTT GTC TAC TAC AAT GCA AAG GAT GAT CTC GAT CCT GAG AAA      439
Asn Glu Val Val Tyr Tyr Asn Ala Lys Asp Asp Leu Asp Pro Glu Lys
120                 125                 130                 135

AAT GAC AGT GAG CCA GGC AGC CAG AGG ATA AAA CCT GTT TTC ATT GAA      487
Asn Asp Ser Glu Pro Gly Ser Gln Arg Ile Lys Pro Val Phe Ile Glu
                140                 145                 150

GAT GCT AAT TTT GGA CGA CAA ATA TCT TAT CAG CAC GCA GCA GTC CAT      535
Asp Ala Asn Phe Gly Arg Gln Ile Ser Tyr Gln His Ala Ala Val His
            155                 160                 165

ATT CCT ACT GAC ATC TAT GAG GGC TCA ACA ATT GTG TTA AAT GAA CTC      583
Ile Pro Thr Asp Ile Tyr Glu Gly Ser Thr Ile Val Leu Asn Glu Leu
        170                 175                 180

AAC TGG ACA AGT GCC TTA GAT GAA GTT TTC AAA AAG AAT CGC GAG GAA      631
Asn Trp Thr Ser Ala Leu Asp Glu Val Phe Lys Lys Asn Arg Glu Glu
185                 190                 195

GAC CCT TCA TTA TTG TGG CAG GTT TTT GGC AGT GCC ACT GGC TTA GCT      679
Asp Pro Ser Leu Leu Trp Gln Val Phe Gly Ser Ala Thr Gly Leu Ala
200                 205                 210                 215

CGA TAT TAT CCA GCT TCA CCA TGG GTT GAT AAT GGT AGA ACT CCA AAT      727
Arg Tyr Tyr Pro Ala Ser Pro Trp Val Asp Asn Gly Arg Thr Pro Asn
                220                 225                 230
```

```
ATG ATT GAC CTT TAT GAT GTA CGC AGA AGA CCA TGG TAC ATC CAA GGA    775
Met Ile Asp Leu Tyr Asp Val Arg Arg Arg Pro Trp Tyr Ile Gln Gly
            235                 240                 245

GCT GCA TCT CCT AAA GAC ATG CTT ATT CTG GTG GAT GTG AGT GGA AGT    823
Ala Ala Ser Pro Lys Asp Met Leu Ile Leu Val Asp Val Ser Gly Ser
            250                 255                 260

GTT AGT GGA TTG ACA CTT AAA CTG ATC CGA ACA TCT GTC TCC GAA ATG    871
Val Ser Gly Leu Thr Leu Lys Leu Ile Arg Thr Ser Val Ser Glu Met
            265                 270                 275

TTA GAA ACC CTC TCA GAT GAT GAT TTC GTG AAT GTA GCT TCA TTT AAC    919
Leu Glu Thr Leu Ser Asp Asp Asp Phe Val Asn Val Ala Ser Phe Asn
280                 285                 290                 295

AGC AAT GCT CAG GAT GTA AGC TGT TTT CAG CAC CTT GTC CAA GCA AAT    967
Ser Asn Ala Gln Asp Val Ser Cys Phe Gln His Leu Val Gln Ala Asn
            300                 305                 310

GTA AGA AAT AAA AAA GTG TTG AAA GAC GCG GTG AAT AAT ATC ACA GCC    1015
Val Arg Asn Lys Lys Val Leu Lys Asp Ala Val Asn Asn Ile Thr Ala
            315                 320                 325

AAA GGA ATT ACA GAT TAT AAG AAG GGC TTT AGT TTT GCT TTT GAA CAG    1063
Lys Gly Ile Thr Asp Tyr Lys Lys Gly Phe Ser Phe Ala Phe Glu Gln
            330                 335                 340

CTG CTT AAT TAT AAT GTT TCC AGA GCA AAC TGC AAT AAG ATT ATT ATG    1111
Leu Leu Asn Tyr Asn Val Ser Arg Ala Asn Cys Asn Lys Ile Ile Met
            345                 350                 355

CTA TTC ACG GAT GGA GAA GAG AGA GCC CAG GAG ATA TTT AAC AAA TAC    1159
Leu Phe Thr Asp Gly Glu Glu Arg Ala Gln Glu Ile Phe Asn Lys Tyr
360                 365                 370                 375

AAT AAA GAT AAA AAA CTA CCT GTA TTC ACC TTC TCA GTT GGT CAA CAC    1207
Asn Lys Asp Lys Lys Leu Pro Val Phe Thr Phe Ser Val Gly Gln His
            380                 385                 390

AAT TAT GAC AGA GGA CCT ATT CAG TGG ATG GCC TGT GAA AAC AAA GGT    1255
Asn Tyr Asp Arg Gly Pro Ile Gln Trp Met Ala Cys Glu Asn Lys Gly
            395                 400                 405

TAT TAT TAT GAA ATT CCT TCC ATT GGT GCA ATA AGA ATC AAT ACT CAG    1303
Tyr Tyr Tyr Glu Ile Pro Ser Ile Gly Ala Ile Arg Ile Asn Thr Gln
            410                 415                 420

GAA TAT TTG GAT GTT TTG GGA AGA CCA ATG GTT TTA GCA GGA GAC AAA    1351
Glu Tyr Leu Asp Val Leu Gly Arg Pro Met Val Leu Ala Gly Asp Lys
            425                 430                 435

GCT AAG CAA GTC CAA TGG ACA AAT GTG TAC CTG GAT GCA TTG GAA CTG    1399
Ala Lys Gln Val Gln Trp Thr Asn Val Tyr Leu Asp Ala Leu Glu Leu
440                 445                 450                 455

GGA CTT GTC ATT ACT GGA ACT CTT CCG GTC TTC AAC ATA ACC GGC CAA    1447
Gly Leu Val Ile Thr Gly Thr Leu Pro Val Phe Asn Ile Thr Gly Gln
            460                 465                 470

TTT GAA AAT AAG ACA AAC TTA AAG AAC CAG CTG ATT CTT GGT GTG ATG    1495
Phe Glu Asn Lys Thr Asn Leu Lys Asn Gln Leu Ile Leu Gly Val Met
            475                 480                 485

GGA GTA GAT GTG TCT TTG GAA GAT ATT AAA AGA CTG ACA CCA CGT TTT    1543
Gly Val Asp Val Ser Leu Glu Asp Ile Lys Arg Leu Thr Pro Arg Phe
            490                 495                 500

ACA CTG TGC CCC AAT GG                                             1560
Thr Leu Cys Pro Asn
            505
```